United States Patent
Friedrich et al.

(10) Patent No.: US 10,632,195 B2
(45) Date of Patent: Apr. 28, 2020

(54) PHARMACEUTICAL DEVICE FOR ELECTRIC-FIELD ASSISTED ADMINISTRATION OF TAPENTADOL AND METHOD OF ADMINISTERING TAPENTADOL WITH SAME

(71) Applicant: Gruenenthal GmbH, Aachen (DE)

(72) Inventors: Ingo Friedrich, Aachen (DE); Martin Mikyna, Munich (DE); Sandra Gedat, Bad Aibling (DE); Richard Guy, Bath (GB)

(73) Assignee: GRUENENTHAL GMBH, Aachen (DE)

( * ) Notice: Subject to any disclaimer, the term of this patent is extended or adjusted under 35 U.S.C. 154(b) by 0 days.

(21) Appl. No.: 14/598,650

(22) Filed: Jan. 16, 2015

(65) Prior Publication Data

US 2015/0148735 A1 May 28, 2015

Related U.S. Application Data

(63) Continuation of application No. PCT/EP2013/002095, filed on Jul. 15, 2013.
(Continued)

(30) Foreign Application Priority Data

Jul. 20, 2012 (EP) .................... 12005317

(51) Int. Cl.
*A61K 41/00* (2006.01)
*A61K 31/135* (2006.01)

(52) U.S. Cl.
CPC ........ *A61K 41/0047* (2013.01); *A61K 31/135* (2013.01)

(58) Field of Classification Search
CPC .............. A61K 41/0047; A61K 9/0009; A61K 9/7084; A61K 9/703; A61K 9/06;
(Continued)

(56) References Cited

U.S. PATENT DOCUMENTS 4,416,274 A * 11/1983 Jacobsen .............. A61N 1/0448
   604/20
4,622,031 A * 11/1986 Sibalis .................. A61M 37/00
   604/20
(Continued)

FOREIGN PATENT DOCUMENTS

DE    10 2010 024 558 A1    12/2011

OTHER PUBLICATIONS

International Search Report dated Oct. 15, 2013 (four (4) pages).
(Continued)

*Primary Examiner* — Imani N Hayman
*Assistant Examiner* — Tiffany Legette
(74) *Attorney, Agent, or Firm* — Norris McLaughlin, P.A.

(57) ABSTRACT

A pharmaceutical device for electric-field assisted administration of Tapentadol and/or of a physiologically acceptable salt thereof, the device comprising at least one pair of electrodes consisting of an active electrode and a counter electrode (1*a* and 2*a* and/or 1*b* and 2*b*), optionally at least one additional electrode as an auxiliary electrode, at least one drug reservoir (3) containing at least a portion of the Tapentadol and/or a physiologically acceptable salt thereof, and means (4) for applying the device to skin (5).

16 Claims, 11 Drawing Sheets

Related U.S. Application Data

(60) Provisional application No. 61/673,948, filed on Jul. 20, 2012.

(58) Field of Classification Search
CPC .... A61K 31/135; A61K 47/38; A61N 1/0412; A61N 1/0416; A61N 1/0428; A61N 1/30; A61N 1/0448; A61N 1/303; A61N 1/325
USPC .......................................................... 604/20
See application file for complete search history.

(56) References Cited

U.S. PATENT DOCUMENTS

| | | | | |
|---|---|---|---|---|
| 4,640,689 | A | * | 2/1987 | Sibalis .................. A61M 37/00 424/449 |
| 5,533,995 | A | * | 7/1996 | Corish .................. A61N 1/303 424/449 |
| 5,540,669 | A | * | 7/1996 | Sage, Jr. ................ A61N 1/044 604/20 |
| 5,605,536 | A | | 2/1997 | Sibalis |
| 5,830,175 | A | | 11/1998 | Flower |
| 2003/0199808 | A1 | | 10/2003 | Henley et al. |
| 2007/0185541 | A1 | * | 8/2007 | Diubaldi .............. A61N 1/0512 607/41 |
| 2009/0005722 | A1 | * | 1/2009 | Jennings-Spring ......................... A61F 13/00063 604/20 |
| 2009/0062720 | A1 | | 3/2009 | Anderson et al. |
| 2010/0189793 | A1 | * | 7/2010 | Meyer .................. A61K 9/0009 424/484 |
| 2010/0247617 | A1 | | 9/2010 | Bencherif et al. |
| 2011/0244022 | A1 | * | 10/2011 | Cottrell ................ A61K 9/7061 424/449 |

OTHER PUBLICATIONS

A. K. Banga, "Transdermal and Intradermal Delivery of Therapeutic Agents", Application of Physical Technologies, CRC Press Inc; 2011.

B. Mudry et al., "Transport Number in Transdermal Iontophoresis", Biophys. J., 2006, 90, pp. 2822-2830.

B. Mudry et al., J. Control. Release, 2006, 111, pp. 362-367.

B. Mudry et al., "Electromigration of ions across the skin: Determination and Prediction of transport numbers", J. Pharm. Sci., 2006, 95, pp. 561-569.

H.A.E. Benson et al., "Topical and Transdermal Drug Delivery", Principles and Practice, John Wiley & Sons, 2011, pp. 1-12.

Riemsma et al., "Systematic Review of Tapentadol in Chronic Severe Pain", Current Medical Research and Opinion, vol. 27, No. 10, 2011, pp. 1907-1930.

Tzschentke T. M. et al., "Tapentadol Hydrochloride", Drugs of the Future, 2006, 31, pp. 1053-1061.

Yogeshvar N. Kalia et al., :Iontophoretic Drug delivery, Advanced Drug Delivery Reviews, vol. 56, No. 5, 2004, pp. 619-658.

K. H. Bauer et al., Lehrbuch der Pharmazeutischen Technologie, 2006.

Written Opinion in connection with PCT International Application No. PCT/EP2013/002095.

* cited by examiner $$t_I = \frac{(J_I \cdot F \cdot z_I)}{I} = \frac{[250\mu g/h / 221.3 g/mol] \cdot 96,500 C/mol \cdot 1}{0.25 mA} = \frac{(1.13 \times 10^{-6} mol/h) \cdot 96,500 C/mol}{[(0.25 \times 10^{-3}) \cdot 3600] C/h} = 0.12$$

PHARMACEUTICAL DEVICE FOR ELECTRIC-FIELD ASSISTED ADMINISTRATION OF TAPENTADOL AND METHOD OF ADMINISTERING TAPENTADOL WITH SAME

This application is a continuation of PCT International Application No. PCT/EP2013/002095, filed Jul. 15, 2013, which: (i) claims the benefit of U.S. Provisional Patent Application No. 61/673,948, filed Jul. 20, 2012; and (ii) claims priority of European Patent Application No. 12005317.8, filed Jul. 20, 2012.

The invention relates to a pharmaceutical device for administration of Tapentadol and/or of a physiologically acceptable salt thereof with the assistance of an electric field, which is useful for the treatment of pain. Said electric field may either locally increase the concentration of Tapentadol in the device according to the present invention at the interface to the skin (electrophoresis), or cause penetration of Tapentadol into the skin (iontophoresis), or both. The device comprises at least one pair of electrodes consisting of an active electrode and a counter electrode, optionally at least one additional electrode as an auxiliary electrode, at least one drug reservoir containing at least a portion of the Tapentadol and/or a physiologically acceptable salt thereof, and means for applying the device to skin.

Tapentadol (Palexia®, Nucynta™), the chemical name for which is (−)-(1R,2R)-3-(3-dimethyl-amino-1-ethyl-2-methyl-propyl)-phenol, is a synthetic, centrally-acting analgesic that is effective for the treatment of moderate to moderately-severe acute or chronic pain. Tapentadol is a centrally acting analgesic with a dual mode of action consisting of μ-opioid receptor (MOR) agonism and norepinephrine (NE) reuptake inhibition. The compound can be employed as the free base or its pharmaceutically acceptable salts and solvates.

The activity of Tapentadol is independent of metabolic activation and resides in a single enantiomer which readily crosses the blood-brain barrier; hence, Tapentadol displays a rapid onset of action after administration. The biotransformation of Tapentadol by metabolic enzymes results in deactivation, i.e., Tapentadol has no active metabolites, and the main metabolic pathway for elimination is phase II glucuronidation. Phase I biotransformations such as hydroxylation and N-demethylation play only a minor role in the metabolic fate of Tapentadol. Owing to the minor involvement of phase I metabolic pathways, Tapentadol has a low potential for drug-drug interactions and interindividual variability (cf. Tzschentke T. M. et al. Tapentadol Hydrochloride, Drugs of the Future 2006, 31, 1053-1061).

Commercial formulations of Tapentadol are typically adapted for oral administration. As Tapentadol has reduced bioavailability upon oral administration, however, it is desirable to administer Tapentadol by alternative routes.

It is known that e.g. transdermal administration of a pharmacologically active ingredient can be advantageous compared to its oral administration, e.g. with respect to bioavailability or patient compliance.

The working principle of such a transdermal administration relies on the release of the pharmacologically active ingredient from the dosage form used such as a patch, its penetration into and through the skin barrier, and its entry into the systemic circulation through the perfused subcutaneous tissue, where it then develops its pharmacological effect at the targeted receptors.

Conventional transdermal delivery systems known in the art are "passive" transdermal delivery systems, i.e. these systems deliver the pharmacologically active ingredient through the skin of the patient unaided, i.e. by application of a conventional transdermal delivery system such as a conventional patch to the skin of a patient.

However, it is known that the permeability of the stratum corneum of the skin to a pharmacologically active ingredient may be a limiting factor for a transdermal delivery system since a sufficient amount of the pharmacologically active ingredient must pass through the skin and into the blood stream in order to have the desired therapeutic effect. Thus, in conventional transdermal delivery system often a relatively high load of the pharmacologically active ingredient contained within the transdermal delivery system such as a patch is necessary in order to achieve a sufficient delivery rate of the active ingredient, which administration route may not be very effective since it is known that usually the major amount, e.g. an amount up to 90% of the active ingredient provided within the transdermal delivery system remains in the system after the period of administration and, thus, only a minor amount such as e.g. an amount of 10% of the active ingredient originally contained within the system prior to use passes through the skin and is actually delivered. In conventional transdermal delivery systems, often percutaneous penetration enhancers are employed to increase the delivery rate of the pharmacologically active ingredient to be administered. Further, in case the transdermal delivery system is a patch, patches having large patch areas have to be provided for this reason in order to achieve a sufficient delivery rate of the active ingredient, which in turn may lead to a higher risk of potential skin irritations caused by the patch and/or any excipients contained therein.

There is a demand for a clinically effective, skin-safe, systemically-safe and convenient systemic delivery system for Tapentadol that enables efficient delivery of a therapeutically effective amount in a relatively short time.

It is therefore an object of the invention to provide a novel pharmaceutical dosage form containing Tapentadol that has advantages compared to the pharmaceutical dosage forms of the prior art. In particular, it is an object of the invention to provide a novel pharmaceutical dosage form containing Tapentadol for transdermal administration that has advantages compared to other pharmaceutical dosage forms of the prior art.

This object has been achieved by the subject-matter of the patent claims and the subject-matter described herein.

One aspect of the present invention is a pharmaceutical device for electric-field assisted administration of Tapentadol and/or of a physiologically acceptable salt thereof, the device comprising at least one pair of electrodes consisting of an active electrode and a counter electrode (1a and 2a and/or 1b and 2b), optionally at least one additional electrode as an auxiliary electrode, at least one drug reservoir (3) containing at least a portion of the Tapentadol and/or a physiologically acceptable salt thereof, and means (4) for applying the device to skin (5).

It has been surprisingly found that electric-field assisted administration, i.e. electrophoretic or iontophoretic administration, and, in particular, combined electrophoretic and iontophoretic administration of Tapentadol and/or of a physiologically acceptable salt thereof, by the pharmaceutical device according to the present invention is advantageous over a corresponding device for "passive" administration of Tapentadol and/or of a physiologically acceptable salt thereof only, i.e. an administration without the aid of applying an electric field, for example with respect to an increase of the total amount of Tapentadol to be delivered to the skin during a certain period of time and with respect to an increase of the drug flux by means of an electric-field.

Further, due to an increase of the total amount of Tapentadol to be delivered to the skin by means of electric-field assisted administration, the inventive device such as an inventive patch may be applied for a shorter time period to the skin of a patient than corresponding devices for "passive" administration only. Thus, the risk of skin irritations caused by the device and/or any excipients contained therein may be lowered accordingly.

Moreover, it has been surprisingly found that electric-field assisted administration, in particular electrophoretic and/or iontophoretic administration, of Tapentadol and/or of a physiologically acceptable salt thereof, by the pharmaceutical device according to the present invention allows the provision of devices such as patches for transdermal delivery of Tapentadol and/or of a physiologically acceptable salt thereof, which have significantly smaller patch areas compared to corresponding patches destined for "passive" administration only, due to a much higher amount of Tapentadol and/or of a physiologically acceptable salt thereof to be delivered to the skin by the aid of an electric field. Such inventive patches having smaller patch areas, i.e. patch areas that have an appropriate size that is as inconspicuous as possible, are more feasible and, further may lower the risk of skin irritations caused by the patch and/or any excipients contained therein.

In addition, it has been surprisingly found that by using the inventive device, Tapentadol can be delivered in a sufficient amount without the aid of any percutaneous penetration enhancers contained in the device in order to increase the delivery rate.

Further, it has been surprisingly found that by using the inventive device, no significant electrically induced degradation of Tapentadol upon administration occurs.

BRIEF DESCRIPTION OF THE DRAWINGS

FIG. 5 provides a graphical representation of the results of the drug flux (given in $\mu g/cm^2$ per h) of Tapentadol across the skin according to example 2a.

FIG. 11 provides a graphical representation of the results of the cumulative combined electrophoretic and iontophoretic delivery (in $\mu g/cm^2$) of Tapentadol across the skin according to example 3a.

FIG. 12 provides a graphical representation of the results of the drug flux (given in $\mu g/cm^2$ per h) of Tapentadol across the skin according to example 3a.

Figure 1:
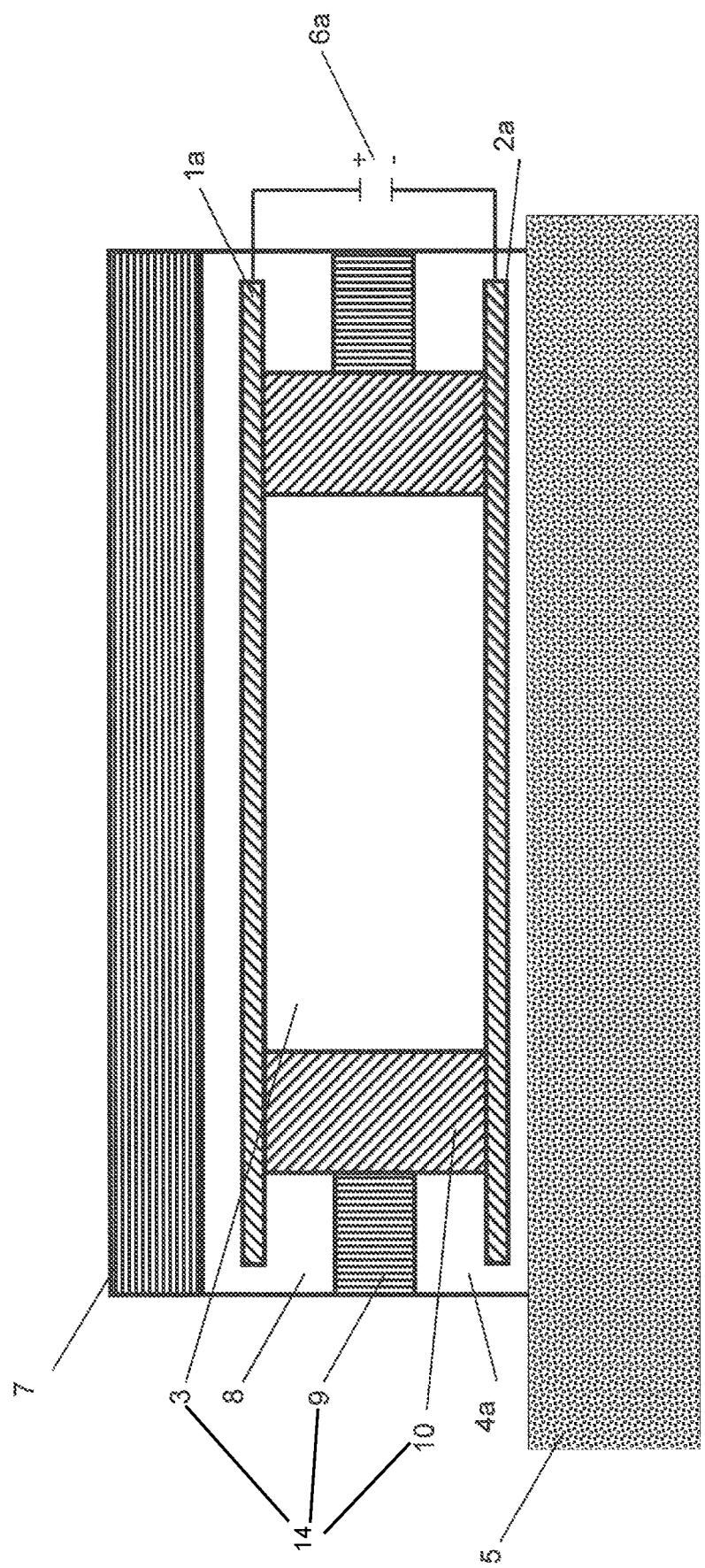
FIG. 1 is a schematic view of a pharmaceutical electrophoretic device according to the present invention.

For the purpose of the present invention, the term "electric-field assisted administration" of Tapentadol and/or of a physiologically acceptable salt thereof preferably includes any form of administration of Tapentadol and/or of a physiologically acceptable salt thereof with the assistance of an electric field. More preferably, said electric field either locally increases the concentration of Tapentadol and/or of a physiologically acceptable salt thereof in the device according to the present invention at the interface to the skin (in this case the inventive device is an electrophoretic device), or causes penetration of Tapentadol and/or of a physiologically acceptable salt thereof into the skin (in this case the inventive device is an iontophoretic device), or both (in this case the inventive device is a combined electrophoretic and iontophoretic device). Thus, the inventive pharmaceutical device preferably is an "active" transdermal delivery system, wherein Tapentadol or a physiologically acceptable salt thereof is delivered through the skin of the patient with the aid of an electric field, e.g. by using iontophoresis or electrophoresis or both.

In a preferred embodiment of the present invention, the inventive pharmaceutical device for electric-field assisted administration of Tapentadol and/or of a physiologically acceptable salt thereof is an iontophoretic device.

A person skilled in the art is aware of iontophoretic devices such as devices disclosed in U.S. Pat. No. 5,830,175, US 2010/0247617 A1 or US 2009/0062720 A1. Conventional iontophoretic devices basically contain two electrodes, which are in contact with a portion of a patient's body such as the skin. A first electrode (the active electrode), delivers the drug into the body by iontophoresis. The second electrode (the counter electrode) closes an electrical circuit that includes the first electrode and the patient's body. The circuit usually includes a source of electrical energy, i.e. a source of an electric current such as a battery. The drug to be administered into the body may be either positively charged (such as in the case of e.g. an acid addition salt of Tapentadol such as Tapentadol hydrochloride) or negatively charged. In the case of a positively charged drug, the anode of the iontophoretic device becomes the active electrode and the cathode serves as the counter electrode to complete the circuit. Alternatively, if the drug to be iontophoretically delivered is negatively charged, the cathode will be the active electrode and the anode will be the counter electrode. The pair of electrodes is usually placed in contact with the skin and with a carrier containing the drug to be administered. Direct electric current is usually applied between the two electrodes. Under the influence of the electric field present, the drug molecules migrate in and through the skin. As current flows between the two electrodes placed at different locations on the skin, which are spaced apart, the current path carries the drug with it.

In another preferred embodiment of the present invention, the inventive pharmaceutical device for electric-field assisted administration of Tapentadol or of a physiologically acceptable salt thereof is an electrophoretic device.

A person skilled in the art is aware of electrophoretic devices such as devices as disclosed in U.S. Pat. No. 5,533,995 or US 2010/189793 A1. The principle of electrophoretic transdermal administration is the migration of a charged drug molecule through a conductive medium or layer in an electric field. Conventional electrophoretic devices basically contain two electrodes, which are arranged face-to-face, and the drug reservoir containing the drug to be administered is located between the electrodes, with only one of the electrodes being in contact with the skin or being close to the skin. In contrast to iontophoretic devices, the current flow in electrophoretic devices occurs merely in the system between the electrodes and not by directly exposing the body to current flow, i.e. in that an increased concentration of the drug to be administered is provided in the proximity to the skin.

In yet another preferred embodiment of the present invention, the inventive pharmaceutical device for electric-field assisted administration of Tapentadol and/or of a physiologically acceptable salt thereof is a combined electrophoretic and iontophoretic device.

A person skilled in the art is aware of such a combined electrophoretic and iontophoretic device, which is e.g. disclosed in DE 10 2010 024 558 A1.

The inventive device for electric-field assisted administration of Tapentadol and/or of a physiologically acceptable salt thereof comprises at least one pair, preferably one pair, of electrodes consisting of an active electrode and a counter electrode (1a and 2a and/or 1b and 2b) and optionally at least one, preferably one, additional electrode as an auxiliary electrode, i.e. comprises at least two electrodes, namely one pair of electrodes consisting of an active electrode and a counter electrode (1a and 2a and/or 1b and 2b), and may additionally comprise at least a third electrode as an auxiliary electrode.

Preferably, the inventive device additionally comprises at least one additional electrode as an auxiliary electrode.

In another preferred embodiment of the present invention, the inventive device comprises at least a first pair of electrodes consisting of an active electrode and a counter electrode (1a and 2a) and, further, at least a second pair of electrodes consisting of an active electrode and a counter electrode (1b and 2b), i.e. the inventive device comprises preferably at least two pair of electrodes consisting of an active electrode and a counter electrode (1a and 2a as well as 1b and 2b). Preferably, in this embodiment, the inventive device does not comprise a further additional electrode as an auxiliary electrode.

For the purpose of the present invention, the term "active electrode" preferably means the electrode of a pair of electrodes, at which' site Tapentadol and/or a physiologically acceptable salt thereof is delivered towards or into the skin of a patient's body by electric-field assistance using an electromotive force. In case Tapentadol and/or a physiologically acceptable salt thereof as the active ingredient employed is positively charged, e.g. in the case of Tapentadol hydrochloride, the active electrode of the inventive device is the anode of the pair of electrodes bearing a positive charge. Alternatively, in case Tapentadol and/or a physiologically acceptable salt as the active ingredient employed is negatively charged, the active electrode of the inventive device is the cathode of the pair of electrodes bearing a negative charge. More preferably, however, the active electrode of the inventive device is the anode of the pair of electrodes bearing a positive charge, in particular in case the inventive pharmaceutical device is an electrophoretic or an iontophoretic device, with the charged drug molecule moving towards the counter electrode.

For the purpose of the present invention, the term "counter electrode" preferably means the electrode of a pair of electrodes, which closes an electrical circuit that includes the first active electrode and optionally also the patient's body, and at which' site negative ions, e.g. of a suitable electrolyte, are delivered away from or into the skin of a patient's body by electric-field assistance using an electromotive force. Preferably, the counter electrode of the inventive device is the cathode of the pair of electrodes bearing a negative charge, in particular in case the inventive pharmaceutical device is an electrophoretic and/or an iontophoretic device.

In another preferred embodiment of the inventive device, together with at least one pair of electrodes consisting of an active electrode and a counter electrode (1a and 2a and/or 1b and 2b) and optionally at least one additional electrode as an auxiliary electrode, the inventive device further comprises at least one reservoir of a suitable electrolyte, preferably a counter electrolyte for providing suitable counter ions for migration, e.g. any kind of a salt such as sodium chloride, which is for example provided in form of an liquid such as an aqueous medium, preferably an aqueous solution or provided in a semi-solid form such as a gel, and which electrolyte reservoir may be part of and/or be integrated in the drug reservoir (3) of the inventive device, which is e.g. the case if Tapentadol hydrochloride as Tapentadol source is used. If the counter electrode and/or the auxiliary electrode, in particular in case the auxiliary electrode functions as a counter electrode, is based on a suitable material for providing counter ions for migration such as silver chloride as material, in which case electrochemical reaction occurring at the cathode produces negatively charged chloride ions suitable for migration, the provision of an electrolyte reservoir, preferably counter electrolyte reservoir, may not be necessary.

In a preferred embodiment of the present invention, the inventive pharmaceutical device is an electrophoretic device and comprises at least one pair of electrodes (1a and 2a), which are provided to create an electric field (Fa) by applying an electrical potential difference (Va), and are arranged such that the electric field (Fa) is substantially perpendicular to the skin (5) when the device is applied thereto, preferably so that the electric field (Fa) induces electrophoretic movement of the Tapentadol and/or of the physiologically acceptable salt thereof within the device from the drug reservoir (3) towards the skin (5). An embodiment of such an inventive device is depicted in FIG. 1.

Figure 2:
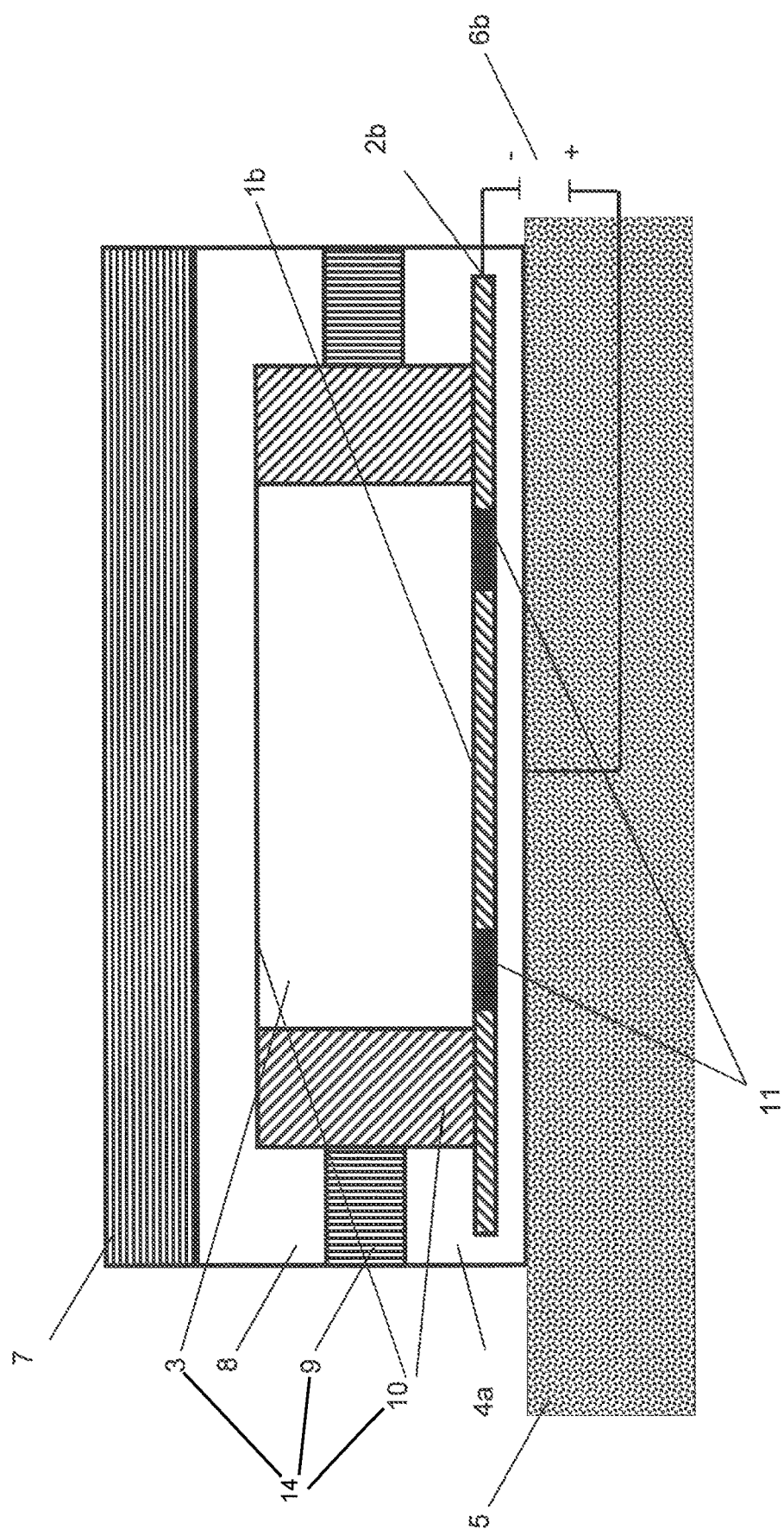
FIG. 2 is a schematic view of a pharmaceutical iontophoretic device according to the present invention.

In another preferred embodiment of the present invention, the inventive pharmaceutical device is an iontophoretic device and comprises at least one pair of electrodes (1b and 2b), which are provided to create an electric field (Fb) by applying an electrical potential (Vb) difference, and are arranged such that the electric field (Fb) is substantially parallel to the skin (5) when the device is applied thereto, preferably so that the electric field (Fb) induces iontophoretic movement of the Tapentadol and/or of the physiologically acceptable salt thereof out of the device from the drug reservoir (3) into the skin (5). Preferably, in such an embodiment of the inventive device, the active electrode (1b) and the counter electrode (2b) of this pair of electrodes (1b and 2b) are separated from each other in order to prevent any occurrence of a short circuit, preferably by means of at least one insulating material (11) as isolator. An embodiment of such an inventive device is depicted in FIG. 2.

In yet a further preferred embodiment of the present invention, the inventive device further comprises at least one additional electrode as an auxiliary electrode, in particular in case the inventive pharmaceutical device is a combined electrophoretic and iontophoretic device. Preferably, in this embodiment of the invention, the device comprises one pair of electrodes consisting of an active electrode and a counter electrode (1a and 2a or 1b and 2b) and optionally at least one additional electrode as an auxiliary electrode.

For the purpose of the present invention, the term "auxiliary electrode" preferably means an optional additional electrode of the inventive device, which may either function as an active electrode or as a counter electrode within the inventive device. Preferably, the optional additional electrode as auxiliary electrode functions as a counter electrode (2b) for iontophoretic administration of Tapentadol and/or a physiologically acceptable salt thereof in a combined electrophoretic and iontophoretic device comprising at least one pair of electrodes consisting of an active electrode and a counter electrode (1a and 2a), said pair being used for electrophoretic administration of Tapentadol and/or a physiologically acceptable salt thereof. Preferably, the auxiliary electrode is a ring electrode, which is preferably arranged within the device around the counter electrode 2a of the at least one pair of electrodes consisting of an active electrode and a counter electrode (1a and 2a), which counter electrode 2a in turn preferably functions as an active electrode (1b) for applying an electric field in order to additionally or alternatively induce iontophoretic movement of the Tapentadol and/or of the physiologically acceptable salt thereof.

Figure 3:
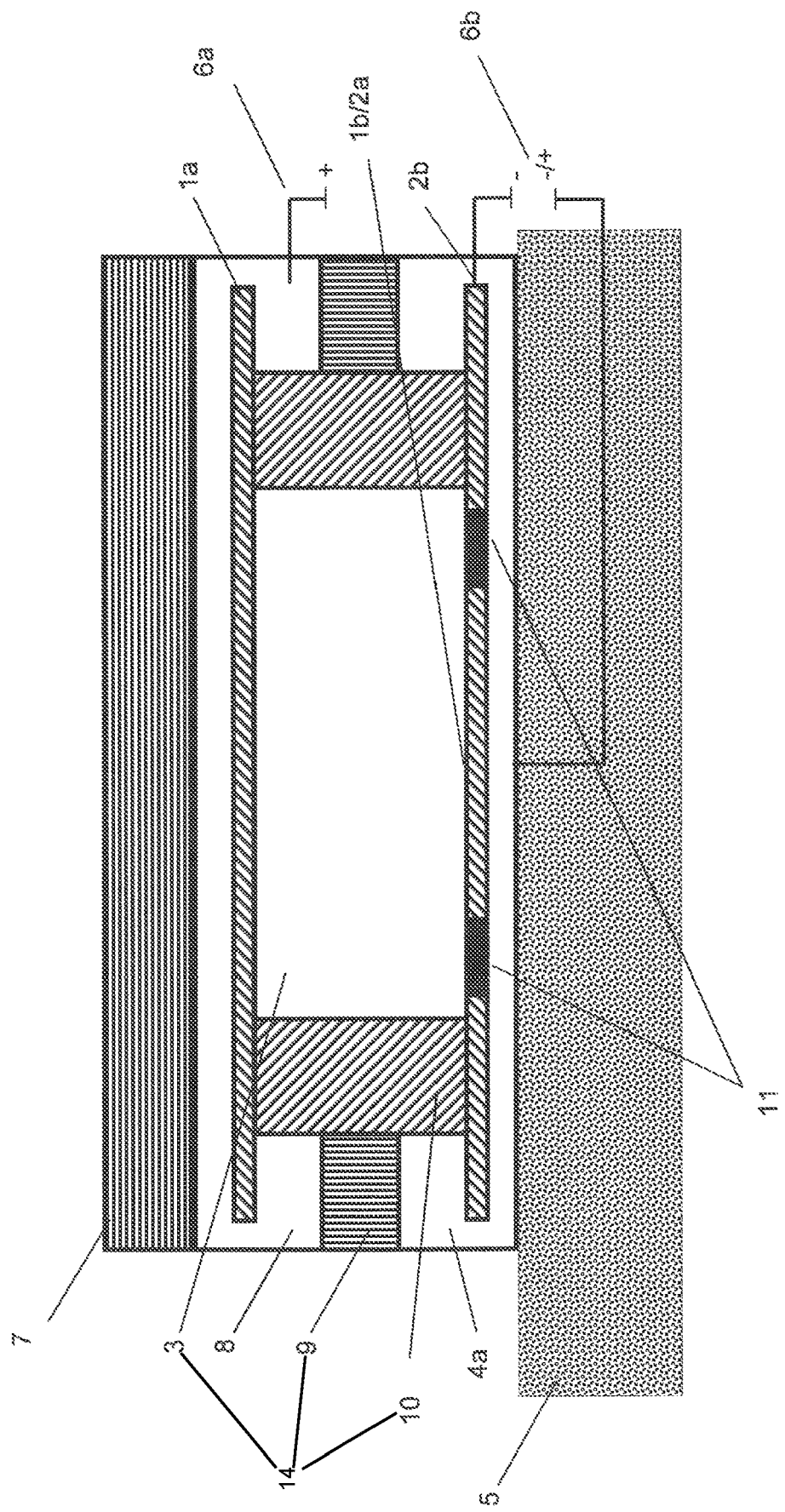
FIG. 3 is a schematic view of a pharmaceutical combined electrophoretic and iontophoretic device according to the present invention.

In case the inventive pharmaceutical device comprises at least one pair of electrodes (1a and 2a), which are arranged in such a way that the electric field (Fa) is substantially perpendicular to the skin (5) when the device is applied thereto, so that the electric field (Fa) induces electrophoretic movement of the Tapentadol and/or of the physiologically acceptable salt thereof within the device from the drug reservoir (3) towards the skin (5), an additional electrode incorporated within the device as an auxiliary electrode preferably functions as a counter electrode (2b) in such a way that the counter electrode (2a) of the pair of electrodes (1a and 2a) is used as an active electrode (1b) for applying an electric field in order to additionally or alternatively induce iontophoretic movement of the Tapentadol and/or of the physiologically acceptable salt thereof out of the device from the drug reservoir (3) into the skin (5). Thus, preferably, the polarity of counter electrode (2a) used for electrophoretic movement is reversed which allows said electrode to function as active electrode (1b) in order to allow iontophoretic movement. Preferably, in such an embodiment of the inventive device, the active electrode (1b) of this pair of electrodes (1b and 2b), which may also function as a counter electrode (2a) with respect to the active electrode (1a) is separated from the additional auxiliary electrode as counter electrode (2b) in order to prevent any occurrence of a short circuit, preferably by means of at least one insulating material (11) as isolator. An embodiment of such an inventive device is depicted in FIG. 3.

In case the inventive pharmaceutical device comprises at least one pair of electrodes (1b and 2b), which are arranged in such a way that the electric field (Fb) is substantially parallel to the skin (5) when the device is applied thereto, so that the electric field (Fb) induces iontophoretic movement of the Tapentadol and/or of the physiologically acceptable salt thereof out of the device from the drug reservoir (3) into the skin (5), an additional electrode incorporated within the device as an auxiliary electrode preferably functions as an active electrode (1a) for applying an electric field using the active electrode (1b) of the pair of electrodes (1b and 2b) as a counter electrode (2a) in order to additionally or alternatively induce electrophoretic movement of the Tapentadol and/or of the physiologically acceptable salt thereof within the device from the drug reservoir (3) towards the skin (5). Thus, preferably, the polarity of active electrode (1b) used for iontophoretic movement is reversed which allows said electrode to function as counter electrode (2a) in order to allow electrophoretic movement. Preferably, in such an embodiment of the inventive device, the active electrode (1b) of the pair of electrodes (1b and 2b), which may also function as a counter electrode (2a) with respect to the additional auxiliary electrode as an active electrode (1a) is separated from counter electrode (2b) in order to prevent any occurrence of a short circuit, preferably by means of an insulating material (11) as isolator. An embodiment of such an inventive device is depicted in FIG. 3.

Thus, preferably, the inventive device comprises at least one pair of electrodes consisting of an active electrode and a counter electrode (1a and 2a) for electrophoretic administration of Tapentadol and/or of the physiologically acceptable salt thereof, and at least one additional electrode as an auxiliary electrode, which functions as a counter electrode (2b) in such a way that the counter electrode (2a) of the pair of electrodes (1a and 2a) is used as an active electrode (1b), for additional or alternative iontophoretic administration of Tapentadol and/or of the physiologically acceptable salt thereof, or at least one pair of electrodes consisting of an active electrode and a counter electrode (1b and 2b) for iontophoretic administration of Tapentadol and/or of the physiologically acceptable salt thereof, and at least one additional electrode as an auxiliary electrode, which functions as an active electrode (1a) such that the active electrode (1b) of the pair of electrodes (1b and 2b) is used as a counter electrode (2a). for additional or alternative electrophoretic administration of Tapentadol and/or of the physiologically acceptable salt thereof, i.e. the inventive device preferably comprises a total of at least three electrodes.

In a preferred embodiment of the present invention, the inventive device comprises at least one first pair of electrodes consisting of an active electrode and a counter electrode (1a and 2a), which are provided to create an electric field (Fa) by applying an electrical potential difference (Va), and are arranged such that the electric field (Fa)

is substantially perpendicular to the skin (5) when the device is applied thereto, preferably for electrophoretic administration of Tapentadol and/or of a physiologically acceptable salt thereof, and at least one additional electrode as an auxiliary electrode, which functions as a counter electrode (2b) in such a way that the counter electrode (2a) of the first pair of electrodes (1a and 2a) is used as an active electrode (1b) for creating an electric field (Fb) by applying an electrical potential difference (Vb), these two electrodes forming a second pair of electrodes consisting of an active electrode and a counter electrode (1b and 2b) and are arranged such that the electric field (Fb) is substantially parallel to the skin (5) when the device is applied thereto, preferably for additional and/or alternative iontophoretic administration of Tapentadol and/or of a physiologically acceptable salt thereof, or at least one first pair of electrodes consisting of an active electrode and a counter electrode (1b and 2b), which are provided to create an electric field (Fb) by applying an electrical potential difference (Vb), and are arranged such that the electric field (Fb) is substantially parallel to the skin (5) when the device is applied thereto, preferably for iontophoretic administration of Tapentadol and/or of a physiologically acceptable salt thereof, and at least one additional electrode as an auxiliary electrode, which functions as an active electrode (1a) for creating an electric field (Fa) by applying an electrical potential difference (Va) using the active electrode (1b) of the first pair of electrodes (1b and 2b) as a counter electrode (2a), these two electrodes forming a second pair of electrodes consisting of an active electrode and a counter electrode (1a and 2a) and are arranged such that the electric field (Fa) is substantially perpendicular to the skin (5) when the device is applied thereto, preferably for additional and/or alternative electrophoretic administration of Tapentadol and/or of a physiologically acceptable salt thereof. An embodiment of such an inventive device is depicted in FIG. 3.

Preferably, in such an inventive device the electric field (Fa) created by the first pair of electrodes consisting of an active electrode and a counter electrode (1a and 2a) induces electrophoretic movement of the Tapentadol and/or of the physiologically acceptable salt thereof within the device from the drug reservoir (3) towards the skin (5) and the electric field (Fb) created by the second pair of electrodes consisting of an active electrode and a counter electrode (1b and 2b) induces iontophoretic movement of the Tapentadol and/or of the physiologically acceptable salt thereof out of the device from the drug reservoir (3) into the skin (5), or the electric field (Fb) created by the first pair of electrodes consisting of an active electrode and a counter electrode (1b and 2b) induces iontophoretic movement of the Tapentadol and/or of the physiologically acceptable salt thereof out of the device from the drug reservoir (3) into the skin (5) and the electric field (Fa) created by the second pair of electrodes consisting of an active electrode and a counter electrode (1a and 2a) induces electrophoretic movement of the Tapentadol and/or of the physiologically acceptable salt thereof within the device from the drug reservoir (3) towards the skin (5).

The electrical potential difference (Va and/or Vb) applied to the at least one pair of electrodes consisting of an active electrode and a counter electrode (1a and 2a and/or 1b and 2b), and/or the optionally present at least one additional electrode as an auxiliary electrode, in order to create an electric field (Fa and/or Fb) should be sufficiently high for the electrolysis to take place. Any threshold values for the electrical potential difference (Va and/or Vb) applied may depend on e.g. the electrode material employed, the nature of the drug reservoir (3) and the electrolyte employed. A person skilled in the art can determine the appropriate electrical potential difference (Va and/or Vb) to be applied in each case e.g. based on any developing gas formation, the measurable current flow or any indicators for determination of a change of the pH value, among others.

In a preferred embodiment of the present invention, the electrical potential difference (Va and/or Vb) applied to the at least one pair of electrodes consisting of an active electrode and a counter electrode (1a and 2a and/or 1b and 2b), and/or the optionally present at least one additional electrode as an auxiliary electrode is within the range of from 0.50 to 12.50 V, more preferably within the range of from 0.75 to 12.25 V, even more preferably within the range of from 1.00 to 12.00 V, still more preferably within the range of from 1.25 to 11.75 V, even still more preferably within the range of from 1.50 to 11.50 V, yet more preferably within the range of from 1.75 to 11.25 V, in particular within the range of from 2.00 to 11.00 V, most preferred within the range of from 2.50 to 10.50 V. In another preferred embodiment of the present invention, the electrical potential difference (Va and/or Vb) applied to the at least one pair of electrodes consisting of an active electrode and a counter electrode (1a and 2a and/or 1b and 2b), and the optionally present at least one additional electrode as an auxiliary electrode is within the range of from 2.75 to 11.00 V, more preferably within the range of from 3.00 to 10.75 V, even more preferably within the range of from 3.25 to 10.50 V, still more preferably within the range of from 3.50 to 10.25 V. In yet another preferred embodiment of the present invention, the electrical potential difference (Va and/or Vb) applied to the at least one pair of electrodes consisting of an active electrode and a counter electrode (1a and 2a and/or 1b and 2b), and/or the optionally present at least one additional electrode as an auxiliary electrode is within the range of from 0.50±0.25 to 11.50±0.25 V, more preferably within the range of from 0.75±0.25 to 11.25±0.25 V, even more preferably within the range of from 1.00±0.25 to 11.00±0.25 V, still more preferably within the range of from 1.25±0.25 to 10.75±0.25 V, even still more preferably within the range of from 1.50±0.25 to 10.50±0.25 V, yet more preferably within the range of from 1.75±0.25 to 10.25±0.25 V, in particular within the range of from 2.00±0.25 to 10.00±0.25 V, most preferred within the range of from 2.50±0.25 to 9.50±0.25 V.

In a preferred embodiment of the present invention, the electrical potential difference (Va and/or Vb) applied to the at least one pair of electrodes consisting of an active electrode and a counter electrode (1a and 2a and/or 1b and 2b), and/or the optionally present at least one additional electrode as an auxiliary electrode is within the range of from 0.50 to 7.50 V, more preferably within the range of from 0.75 to 7.25 V, even more preferably within the range of from 1.00 to 7.00 V, still more preferably within the range of from 1.25 to 6.75 V, even still more preferably within the range of from 1.50 to 6.50 V, yet more preferably within the range of from 1.75 to 6.25 V, in particular within the range of from 2.00 to 6.00 V, most preferred within the range of from 2.50 to 6.50 V. In another preferred embodiment of the present invention, the electrical potential difference (Va and/or Vb) applied to the at least one pair of electrodes consisting of an active electrode and a counter electrode (1a and 2a and/or 1b and 2b), and/or the optionally present at least one additional electrode as an auxiliary electrode is within the range of from 2.75 to 6.25 V, more preferably within the range of from 3.00 to 6.00 V, even more preferably within the range of from 3.25 to 5.75 V, still more preferably within the range of from 3.50 to 5.50 V. In yet another preferred embodiment of the present invention, the electrical potential difference (Va and/or Vb) applied to the at least one pair of electrodes consisting of an active electrode and a counter electrode (1a and 2a and/or 1b and 2b), and/or the optionally present at least one additional electrode as an auxiliary electrode is within the range of from 0.50±0.25 to 7.50±0.25 V, more preferably within the range of from 0.75±0.25 to 7.25±0.25 V, even more preferably within the range of from 1.00±0.25 to 7.00±0.25 V, still more preferably within the range of from 1.25±0.25 to 6.75±0.25 V, even still more preferably within the range of from 1.50±0.25 to 6.50±0.25 V, yet more preferably within the range of from 1.75±0.25 to 6.25±0.25 V, in particular within the range of from 2.00±0.25 to 6.00±0.25 V, most preferred within the range of from 2.50±0.25 to 6.50±0.25 V.

In yet another preferred embodiment of the present invention, the electrical potential difference (Va and/or Vb) applied to the at least one pair of electrodes consisting of an active electrode and a counter electrode (1a and 2a and/or 1b and 2b), and/or the optionally present at least one additional electrode as an auxiliary electrode is within the range of from 2.75±0.25 to 6.25±0.25 V, more preferably within the range of from 3.00±0.25 to 6.00±0.25 V, even more preferably within the range of from 3.25±0.25 to 5.75±0.25 V, still more preferably within the range of from 3.50±0.25 to 5.50±0.25 V.

In another preferred embodiment of the present invention, the electrical potential difference (Va and/or Vb) applied to the at least one pair of electrodes consisting of an active electrode and a counter electrode (1a and 2a and/or 1b and 2b), and/or the optionally present at least one additional electrode as an auxiliary electrode is at least 0.50±0.25 V, more preferably at least 0.75±0.25 V, even more preferably at least 1.00±0.25 V, still more preferably at least 1.25±0.25 V, even still more preferably at least 1.50±0.25 V, yet even more preferably at least 1.75±0.25 V, in particular at least 2.00±0.25 V, most preferred at least 2.50±0.25 V.

In another preferred embodiment of the present invention, the electrical potential difference (Va and/or Vb) is repeatedly applied to the at least one pair of electrodes consisting of an active electrode and a counter electrode (1a and 2a and/or 1b and 2b), and/or the optionally present at least one additional electrode as an auxiliary electrode, in predetermined repetition intervals (given in h, i.e. in hours) in each case for a predetermined period of time (given in s, i.e. in seconds or in h, i.e. hours), within the total period of time, during which the inventive device is applied to the skin (5).

For the purpose of the present invention, the term "repeatedly" preferably comprises the repetition of an application of an electrical potential difference (Va and/or Vb) to the at least one pair of electrodes consisting of an active electrode and a counter electrode (1a and 2a and/or 1b and 2b), and/or the optionally present at least one additional electrode as an auxiliary electrode within the total period of time, during which the inventive device is applied to the skin (5), at least once, preferably at least twice more preferably at least three times, but may alternatively comprise said repetition between 1 and 500, preferably 1 and 300, more preferably between 1 and 250, even more preferably between 1 and 200, yet more preferably between 1 and 100, in particular between 1 and 50, most preferred between 1 and 20 times.

Preferably, the electrical potential difference (Va and/or Vb) repeatedly applied is within the range of from 0.50 to 12.50 V, more preferably within the range of from 0.75 to 12.25 V, even more preferably within the range of from 1.00 to 12.00 V, still more preferably within the range of from 1.25 to 11.75 V, even still more preferably within the range of from 1.50 to 11.50 V, yet more preferably within the range of from 1.75 to 11.25 V, in particular within the range of from 2.00 to 11.00 V, most preferred within the range of from 2.50 to 10.50 V, or within the range of from 0.50 to 7.50 V, more preferably within the range of from 0.75 to 7.25 V, even more preferably within the range of from 1.00 to 7.00 V, still more preferably within the range of from 1.25 to 6.75 V, even still more preferably within the range of from 1.50 to 6.50 V, yet more preferably within the range of from 1.75 to 6.25 V, in particular within the range of from 2.00 to 6.00 V, most preferred within the range of from 2.50 to 6.50 V, or said electrical potential difference (Va and/or Vb) repeatedly applied is within the range of from 0.50±0.25 to 12.50±0.25 V, preferably within the range of from 0.75±0.25 to 12.25±0.25 V, even more preferably within the range of from 1.00±0.25 to 12.00±0.25 V, still more preferably within the range of from 1.25±0.25 to 11.75±0.25 V, even still more preferably within the range of from 1.50±0.25 to 11.50±0.25 V, yet more preferably within the range of from 1.75±0.25 to 11.25±0.25 V, in particular within the range of from 2.00±0.25 to 11.00±0.25 V, most preferred within the range of from 2.50±0.25 to 10.50±0.25 V or said electrical potential difference (Va and/or Vb) repeatedly applied is within the range of from 0.50±0.25 to 7.50±0.25 V, preferably within the range of from 0.75±0.25 to 7.25±0.25 V, even more preferably within the range of from 1.00±0.25 to 7.00±0.25 V, still more preferably within the range of from 1.25±0.25 to 6.75±0.25 V, even still more preferably within the range of from 1.50±0.25 to 6.50±0.25 V, yet more preferably within the range of from 1.75±0.25 to 6.25±0.25 V, in particular within the range of from 2.00±0.25 to 6.00±0.25 V, most preferred within the range of from 2.50±0.25 to 6.50±0.25 V, or said electrical potential difference (Va and/or Vb) repeatedly applied is within the range of from 3.00±0.25 to 6.00±0.25 V, even more preferably within the range of from 3.25±0.25 to 5.75±0.25 V, still more preferably within the range of from 3.50±0.25 to 5.50±0.25 V, preferably wherein the predetermined period of time is in each case independently of one another within the range of from 0.5 s to 120 s, preferably within the range of from 0.75 s to 110 s, more preferably within the range of from 1.00 s to 100 s, even more preferably within the range of from 1.25 s to 90 s, still more preferably within the range of from 1.50 s to 80 s, yet more preferably within the range of from 1.75 s to 70 s, in particular within the range of from 2.00 s to 60 s, or wherein the predetermined period of time is each case independently of one another within the range of from 0.5±0.25 s to 120±10 s, preferably within the range of from 0.75±0.25 s to 100±10 s, more preferably within the range of from 1.00±0.25 s to 80±10 s, even more preferably within the range of from 1.25±0.25 s to 60±10 s, still more preferably within the range of from 1.50±0.25 s to 55±10 s, yet more preferably within the range of from 1.75±0.25 s to 50±10 s, in particular within the range of from 2.00±0.25 s to 45±10 s, especially, when electrical potential difference (Va) is applied to the at least one pair of electrodes consisting of an active electrode and a counter electrode (1a and 2a) and/or the optionally present at least one additional electrode as an auxiliary electrode for electrophoretic administration, and/or preferably wherein the predetermined period of time is in each case independently of one another within the range of from 0.5 s to 10 h, preferably within the range of from 0.75 s to 9.5 h, more preferably within the range of from 1.00 s to 9 h, even more preferably within the range of from 1.25 s to 8.5 h, still more preferably within the range of from 1.50 s to 8 h, yet more preferably within the range of from 1.75 s to 7.5 h, in particular within the range of from 2.00 s to 7 h, or wherein the predetermined period of time is each case independently of one another within the range of from 0.5±0.25 s to 10±1 h, preferably within the range of from 0.75±0.25 s to 9±1 h, more preferably within the range of from 1.00±0.25 s to 8±1 h, even more preferably within the range of from 1.25±0.25 s to 6±1 h, still more preferably within the range of from 1.50±0.25 s to 5±1 h, yet more preferably within the range of from 1.75±0.25 s to 3±1 h, in particular within the range of from 2.00±0.25 s to 2±1 h, especially, when electrical potential difference (Vb) is applied to the at least one pair of electrodes consisting of an active electrode and a counter electrode (1b and 2b) and/or the optionally present at least one additional electrode as an auxiliary electrode for iontophoretic administration, and/or when electrical potential difference (Va and/or Vb) is applied to the at least one pair of electrodes consisting of an active electrode and a counter electrode (1a and 2a and/or 1b and 2b) and/or the optionally present at least one additional electrode as an auxiliary electrode for combined electrophoretic and iontophoretic administration, and/or wherein the predetermined repetition intervals (e.g. given in h, i.e. in hours) within the total time of administration of the inventive device are in each case independently of one another within the range of from 0.5 h to 24 h, preferably within the range of from 1.5 h to 23 h, more preferably within the range of from 2.5 h to 22 h, even more preferably within the range of from 3.5 h to 21 h, still more preferably within the range of from 4.5 h to 20 h, yet more preferably within the range of from 5.5 h to 19 h, in particular within the range of from 6.5 h to 18 h, most preferred within the range of from 7.5 h to 17 h, or wherein the predetermined repetition intervals (given in h, i.e. in hours) within the total time of administration of the inventive device are in each case independently of one another within the range of from 1.0±0.5 h to 24±2 h, preferably within the range of from 1.5±0.5 h to 23±2 h, more preferably within the range of from 2.5±0.5 h to 22±2 h, even more preferably within the range of from 3.5±0.5 h to 21±2 h, still more preferably within the range of from 4.5±0.5 h to 20±2 h, yet more preferably within the range of from 5.5±0.5 h to 19±2 h, in particular within the range of from 6.5±0.5 h to 18±2 h, most preferred within the range of from 7.5±0.5 h to 17±2 h.

It has been found that the delivered amount of Tapentadol can be increased and/or adjusted and/or controlled by repeatedly applying the electrical potential difference (Va and/or Vb) in predetermined repetition intervals for a predetermined period of time within the total period of time, during which the inventive device is applied to the skin (5).

In a preferred embodiment of the present invention the predetermined period of time is in each case independently of one another within the range of from 0.5 s to 120 s, preferably within the range of from 0.75 s to 110 s, more preferably within the range of from 1.00 s to 100 s, even more preferably within the range of from 1.25 s to 90 s, still more preferably within the range of from 1.50 s to 80 s, yet more preferably within the range of from 1.75 s to 70 s, in particular within the range of from 2.00 s to 60 s, or wherein the predetermined period of time is each case independently of one another within the range of from 0.5±0.25 s to 120±10 s, preferably within the range of from 0.75±0.25 s to 100±10 s, more preferably within the range of from 1.00±0.25 s to 80±10 s, even more preferably within the range of from 1.25±0.25 s to 60±10 s, still more preferably within the range of from 1.50±0.25 s to 55±10 s, yet more preferably within the range of from 1.75±0.25 s to 50±10 s, in particular within the range of from 2.00±0.25 s to 45±10 s, especially, when electrical potential difference (Va) is applied to the at least one pair of electrodes consisting of an active electrode and a counter electrode (1a and 2a) and/or the optionally present at least one additional electrode as an auxiliary electrode for electrophoretic administration.

In another preferred embodiment of the present invention the predetermined period of time is in each case independently of one another within the range of from 0.5 s to 10 h, preferably within the range of from 0.75 s to 9.5 h, more preferably within the range of from 1.00 s to 9 h, even more preferably within the range of from 1.25 s to 8.5 h, still more preferably within the range of from 1.50 s to 8 h, yet more preferably within the range of from 1.75 s to 7.5 h, in particular within the range of from 2.00 s to 7 h, or wherein the predetermined period of time is each case independently of one another within the range of from 0.5±0.25 s to 10±1 h, preferably within the range of from 0.75±0.25 s to 9±1 h, more preferably within the range of from 1.00±0.25 s to 8±1 h, even more preferably within the range of from 1.25±0.25 s to 6±1 h, still more preferably within the range of from 1.50±0.25 s to 5±1 h, yet more preferably within the range of from 1.75±0.25 s to 3±1 h, in particular within the range of from 2.00±0.25 s to 2±1 h, especially, when electrical potential difference (Vb) is applied to the at least one pair of electrodes consisting of an active electrode and a counter electrode (1b and 2b) and/or the optionally present at least one additional electrode as an auxiliary electrode for iontophoretic administration, and/or when electrical potential difference (Va and/or Vb) is applied to the at least one pair of electrodes consisting of an active electrode and a counter electrode (1a and 2a and/or 1b and 2b) and/or the optionally present at least one additional electrode as an auxiliary electrode, preferably consecutively, for combined electrophoretic and iontophoretic administration.

In another preferred embodiment of the present invention the predetermined repetition intervals (e.g. given in h, i.e. in hours) within the total time of administration of the inventive device are in each case independently of one another within the range of from 0.5 h to 24 h, preferably within the range of from 1.5 h to 23 h, more preferably within the range of from 2.5 h to 22 h, even more preferably within the range of from 3.5 h to 21 h, still more preferably within the range of from 4.5 h to 20 h, yet more preferably within the range of from 5.5 h to 19 h, in particular within the range of from 6.5 h to 18 h, most preferred within the range of from 7.5 h to 17 h, or wherein the predetermined repetition intervals (given in h, i.e. in hours) within the total time of administration of the inventive device are in each case independently of one another within the range of from 1.0±0.5 h to 24±2 h, preferably within the range of from 1.5±0.5 h to 23±2 h, more preferably within the range of from 2.5±0.5 h to 22±2 h, even more preferably within the range of from 3.5±0.5 h to 21±2 h, still more preferably within the range of from 4.5±0.5 h to 20±2 h, yet more preferably within the range of from 5.5±0.5 h to 19±2 h, in particular within the range of from 6.5±0.5 h to 18±2 h, most preferred within the range of from 7.5±0.5 h to 17±2 h.

Preferably, the total period of time during which an electrical potential difference (Va and/or Vb) is applied to the at least one pair of electrodes consisting of an active electrode and a counter electrode (1a and 2a and/or 1b and 2b), and/or the optionally present at least one additional electrode as an auxiliary electrode is at most 20%, preferably at most 18%, more preferably at most 16%, even more preferably at most 14%, still more preferably at most 12%, even more preferably at most 10% of the total period of time during which the device is applied to the skin (5). In another preferred embodiment of the present invention, said total time period is at most 9%, preferably at most 8%, more preferably at most 7%, even more preferably at most 6%, still more preferably at most 5%, even further more preferably at most 4% of the total period of time during which the device is applied to the skin (5). In another preferred embodiment of the present invention, said total time period is at most 12±2%, preferably at most 11±2%, more preferably at most 10±2%, even more preferably at most 9±2%, still more preferably at most 8±2%, even still more preferably at most 7±2%, yet more preferably at most 6±2%, in particular at most 5±2% of the total period of time during which the device is applied to the skin (5).

In another preferred embodiment, the total period of time during which an electrical potential difference (Va and/or Vb) is applied to the at least one pair of electrodes consisting of an active electrode and a counter electrode (1*a* and 2*a* and/or 1*b* and 2*b*), and/or the optionally present at least one additional electrode as an auxiliary electrode is at most 75%, preferably at most 65%, more preferably at most 55%, even more preferably at most 50%, still more preferably at most 45%, even more preferably at most 40% of the total period of time during which the device is applied to the skin (5). In another preferred embodiment of the present invention, said total time period is at most 35%, preferably at most 30%, more preferably at most 25%, even more preferably at most 20%, still more preferably at most 15%, even further more preferably at most 10% of the total period of time during which the device is applied to the skin (5). In another preferred embodiment of the present invention, said total time period is at most 75±10%, preferably at most 65±10%, more preferably at most 55±10%, even more preferably at most 45±10%, still more preferably at most 35±10%, even still more preferably at most 25±10%, yet more preferably at most 15±10%, in particular at most 10±5% of the total period of time during which the device is applied to the skin (5).

Preferably, the total period of time during which an electrical potential difference (Va and/or Vb) is applied to the at least one pair of electrodes consisting of an active electrode and a counter electrode (1*a* and 2*a* and/or 1*b* and 2*b*), and/or the optionally present at least one additional electrode as an auxiliary electrode is at most 4.0 hours, preferably at most 3.5 hours, more preferably at most 3.0 hours, even preferably at most 2.5 hours, yet more preferably at most 2.0 hours, further more preferably at most 1.5 hours, in particular at most 1.0 hours, most preferred at most 0.5 hours. In another preferred embodiment of the present invention, said total time period during which an electrical potential difference (Va and/or Vb) is applied to the at least one pair of electrodes consisting of an active electrode and a counter electrode (1*a* and 2*a* and/or 1*b* and 2*b*), and the optionally present at least one additional electrode as an auxiliary electrode, is at most 4.0±0.5 hours, preferably at most 3.5±0.5 hours, more preferably at most 3.0±0.5 hours, even preferably at most 2.5±0.5 hours, yet more preferably at most 2.0±0.5 hours, further more preferably at most 1.5±0.5 hours, in particular at most 1.0±0.5 hours, most preferred at most 0.5±0.25 hours.

In another preferred embodiment, the total period of time during which an electrical potential difference (Va and/or Vb) is applied to the at least one pair of electrodes consisting of an active electrode and a counter electrode (1*a* and 2*a* and/or 1*b* and 2*b*), and/or the optionally present at least one additional electrode as an auxiliary electrode is at most 24 hours, preferably at most 22 hours, more preferably at most 20 hours, even preferably at most 15 hours, yet more preferably at most 12 hours, further more preferably at most 10 hours, in particular at most 8 hours, most preferred at most 5 hours. In another preferred embodiment of the present invention, said total time period during which an electrical potential difference (Va and/or Vb) is applied to the at least one pair of electrodes consisting of an active electrode and a counter electrode (1*a* and 2*a* and/or 1*b* and 2*b*), and the optionally present at least one additional electrode as an auxiliary electrode, is at most 10±5 hours, preferably at most 9±5 hours, more preferably at most 8±5 hours, even preferably at most 7±5 hours, yet more preferably at most 6±5 hours, further more preferably at most 5±4 hours, in particular at most 5±3 hours, most preferred at most 5±4 hours.

In another preferred embodiment of the present invention the total period of time, during which the inventive device is applied to the skin (5) is at least 1 hour, preferably at least 2 hours, more preferably at least 3 hours, even more preferably at least 4 hours, yet more preferably at least 5 hours, further more preferably at least 6 hours, in particular at least 7 hours, most preferred at least 8 hours. In another preferred embodiment of the present invention the total period of time, during which the inventive device is applied to the skin (5), is within the range of from 1 hour to 72 h, preferably within the range of from 3 hours to 66 hours, more preferably within the range of from 6 hours to 60 hours, even more preferably within the range of from 9 hours to 54 hours, still more preferably within the range of from 12 hours to 48 hours, yet more preferably within the range of from 15 hours to 42 hours, in particular within the range of from 18 hours to 36 hours, most preferred within the range of from 21 hours to 30 hours.

Preferably, by using a combined electrophoretic and iontophoretic inventive device, Tapentadol and/or a physiologically acceptable salt thereof, is administered in a first period of electric-field assisted administration, preferably electrophoretically induced administration, followed by a second period of electric-field assisted administration, preferably iontophoretically induced administration, optionally followed by a third period of non-electric-field assisted administration, wherein the duration of each period is independently of one another. In a preferred embodiment of the present invention, the first cycle comprising the first, second and the optional third period, is repeated at least once, more preferably at least twice, even more preferably at least three times.

In a preferred embodiment, the inventive device comprises a plurality of the following components of the inventive device:
one pair of electrodes consisting of an active electrode and a counter electrode (1*a* and 2*a* or 1*b* and 2*b*) as component (1) optionally one additional electrode as an auxiliary electrode as component (2), and one drug reservoir (3) containing at least a portion of the Tapentadol and/or a physiologically acceptable salt thereof as component (3).

Preferably, in such an embodiment of the inventive device, a component (1) and component (3) may be surrounded by optional components (2), e.g. in a honeycomb, circular or strip-shaped structure with repeating arrangements, which in turn may be surrounded by components (1) and (3).

Any suitable electrically conductive materials may be employed for the construction of the inventively used pair(s) of electrodes consisting of an active electrode and a counter electrode as well as for the auxiliary electrodes, which may function as active electrode or counter electrode. A person skilled in the art is aware that the active electrode should in each case be compatible with its corresponding counter electrode. Preferably, each of the active electrode, the counter electrode and/or the auxiliary electrode is gas-permeable. Preferably, the active electrode, the counter electrode and/or the auxiliary electrode are based on a material selected from the group consisting of electrically conductive metals such as copper, aluminum, titanium or a noble metal such as silver, gold, platinum or palladium, electrically conductive alloys, carbon-based material such as graphitic material, stainless steel, textile fabrics such as any kind of suitable fiber material, which may be at least partially coated with an electrically conductive material or equipped at least in part with such a material, and any kind of suitable electrically conductive polymeric material such as a respective mixture of hydrophilic and hydrophobic polymers. In particular, any of the active electrode, the counter electrode and/or the auxiliary electrode is independently of one another based on silver or silver chloride, wherein silver chloride may be optionally printed on silver, especially when the inventive device is an iontophoretic device. Silver as an electrode material for any of the active electrode, the counter electrode and/or the auxiliary electrode is especially preferred. In another preferred embodiment any of the active electrode, the counter electrode and/or the auxiliary electrode is independently of one another based on a carbon-based material such as graphitic material, or on suitable electrically conductive polymeric material, especially when the inventive device is an electrophoretic device. Any of the materials employed for the constructions of the electrodes may optionally be coated or plated, e.g. silver-, zinc- or copper-plated or coated material may be employed. The electrodes can be construed in any suitable form such as in the form of a fabric, preferably a grid-like fabric, in the form of perforated or porous foils, or in the form of foil printed or pattern printed with an electrically conductive material.

In case the counter electrode and/or the auxiliary electrode, in particular in case the auxiliary electrode functions as a counter electrode, is based on silver chloride or contains silver chloride, an electrochemical reaction occurring at the cathode in this case produces negatively charged chloride ions suitable for migration. Therefore, the provision of an additional electrolyte reservoir, e.g. a counter electrolyte reservoir, is not necessary in such an embodiment. In this embodiment, the active electrode is preferably based on silver.

In case the inventive device is a iontophoretic device comprising at least one pair of electrodes consisting of an active electrode (1b) and a counter electrode (2b), these two electrodes are preferably separated from each other by means of an insulating material (11) as isolator. Any suitable conventional material may be employed as insulating material.

In case the inventive device is a combined electrophoretic and iontophoretic device comprising at least one pair of electrodes consisting of an active electrode and a counter electrode (1a and 2a and/or 1b and 2b) and at least one optionally present additional electrode as an auxiliary electrode, active electrode (1b) and counter electrode (2b) are preferably separated from each other by means of an insulating material (11) as isolator. Any suitable conventional material may be employed as insulating material.

In a preferred embodiment of the present invention, the inventive device further comprises a control unit for regulating an electrical potential difference (Va and/or Vb) applied to the pair(s) of electrodes (1a and 2a and/or 1b and 2b) and the optionally present auxiliary electrode(s), e.g. for controlling the voltage or current applied as a function of time and/or for generating complex current wave forms such as pulses or sinusoidal waves.

In case the inventive device is a combined electrophoretic and iontophoretic device, the control unit can be preferably used to both apply an electrical potential difference (Va) in order induce electrophoretic administration of Tapentadol and/or of a physiologically acceptable salt thereof and to apply an electrical potential difference (Vb) in order induce iontophoretic administration of Tapentadol and/or of a physiologically acceptable salt thereof.

Any suitable control unit may be employed, such as e.g. a microprocessor controlled electrical instrument, for example in the form of a control circuit. Preferably, the control unit may also include a galvanostatic unit for regulation of the current and/or voltage and/or may further comprise a sensor unit, e.g. for monitoring the concentration of the (remaining) amount of Tapentadol and/or of a physiologically acceptable salt thereof within the inventive device. The electronics of the control unit may be partially or in total be implemented as electronic printing into the device, for example in a surface layer (7) of the inventive device, in particular if the device is a patch.

Preferably, the electrodes employed in the inventive device, i.e. the inventively used pair(s) of electrodes consisting of an active electrode and a counter electrode (1a and 2a and/or 1b and 2b) as well as any auxiliary electrode(s), are connected, e.g. via at least one wire, to the control unit, for regulating an electrical potential difference (Va and/or Vb) applied to the pair(s) of electrodes (1a and 2a and/or 1b and 2b) and the optionally present auxiliary electrode(s).

The electric field (Fa and/or Fb) created by applying said electrical potential difference (Va and/or Vb), and, thus, the inventive device itself, may be voltage or current regulated. The voltage or current may be constant, variable or pulsed. By voltage regulation, the time required to deliver a specific dose may vary significantly from patient to patient, because differences in skin resistance may cause differences in delivery current and, thus, the inventive device may have to applied to the patient's' skin for a longer time in order to compensate the possibility of high skin resistance. However, patients having relatively low skin resistance may experience higher than desirable currents that in turn may cause skin irritation and/or allow the delivery of higher than desirable dosage rates of Tapentadol and/or of the physiologically acceptable salt thereof to the systemic circulation of a patient. Current regulation, however, may provide a more consistent delivery rate that is less affected by variability in skin resistance. Thus, the inventive device is preferably current regulated.

The control unit of the inventive device may be further used—besides regulating an electrical potential difference (Va and/or Vb) applied to the pair(s) of electrodes (1a and 2a and/or 1b and 2b) and the optionally present auxiliary electrode(s), in particular for controlling the voltage or current applied as a function of time and/or for generating complex current wave forms such as pulses or sinusoidal waves—, for controlling and/or monitoring the delivery rate, e.g. the delivered amount, of Tapentadol and/or of a physiologically acceptable salt thereof, to the patient, for example in order to achieve a desired delivery rate, for example such that the delivery rate is constant or occurs according to a predetermined profile, for example in predetermined intervals, in particular for controlling and/or monitoring the strength and pulse lengths of the electric field(s) (Fa and/or Fb) created by applying an electrical potential difference (Va and/or Vb) in order to achieve a desired delivery rate, for example such that the delivery rate is constant or occurs according to a predetermined profile, and for controlling and/or monitoring the concentration of the (remaining)

amount of Tapentadol and/or of a physiologically acceptable salt thereof within the inventive device.

In a preferred embodiment of the present invention, the inventive device additionally comprises at least one electric power source (6a and/or 6b).

Any suitable electric power source may be employed such as any kind of batteries, such as conventional miniature or light-weight batteries, for example conventional sheet or button cell batteries and/or micro-batteries, that allows application of a voltage to the electrode pairs in order to create a regulated current flow, and that may be connected in series or in parallel. Preferably, the electric power source (6a and/or 6b) is positioned between the active electrode and the counter electrode of a pair of electrodes such that one electrode is connected to one pole of the electric power source (6a and/or 6b) and the other electrode is connected to the opposite pole.

In another preferred embodiment of the present invention, the inventively used pair(s) of electrodes consisting of an active electrode and a counter electrode (1a and 2a and/or 1b and 2b) as well as any auxiliary electrodes, employed in the inventive device may serve as electric power source (6a and/or 6b) or are at least integral portions of such an electric power source, if the respective electrode pair is a "galvanic couple" such as a zinc based active electrode and a silver chloride based counter electrode, which is able to generate its own electric power by electrochemical reaction.

Preferably, the control unit and/or the electrodes employed in the inventive device, i.e. the inventively used pair(s) of electrodes consisting of an active electrode and a counter electrode (1a and 2a and/or 1b and 2b) as well as any auxiliary electrodes, are connected, e.g. via a wire, to the electric power source (6a and/or 6b). The electronics of the electric power source (6a and/or 6b) may be partially or in total be implemented as electronic printing into the device, for example in a surface layer (7) of the inventive device, in particular the device is a patch.

Preferably, the inventive pharmaceutical device is an integrated pharmaceutical device.

For the purpose of the present invention, the term "integrated" preferably means that the inventive device is completely self-contained and defines inventive devices which contain Tapentadol and/or a physiolo-gi-cally acceptable salt thereof, optionally a power source (6a and/or 6b), optionally a control unit, and optionally further components to deliver Tapentadol or of the physiologically acceptable salt thereof by electric-field assistance, i.e. iontophoretically and/or electrophoretically in a single device, preferably a single patch. The term "integrated", denotes in particular devices which do not require a separate power source and/or control unit, and thus, do not require the presence of any external wires, such that such an integrated inventive device is preferably wearable.

In a preferred embodiment of the present invention, the inventive pharmaceutical device for electric-field assisted administration of Tapentadol or of a physiologically acceptable salt thereof is an integrated, preferably wearable, iontophoretic device.

In another preferred embodiment of the present invention, the inventive pharmaceutical device for electric-field assisted administration of Tapentadol or of a physiologically acceptable salt thereof is an integrated, preferably wearable, electrophoretic device.

In yet another preferred embodiment of the present invention, the inventive pharmaceutical device for electric-field assisted administration of Tapentadol or of a physiologically acceptable salt thereof is an integrated, preferably wearable, combined electrophoretic and iontophoretic electrophoretic device.

Optionally, the inventive pharmaceutical device, especially when provided as an integrated pharmaceutical device in a single device, may also preferably include a display unit such as an LCD (liquid crystal display), which may display current, voltage and timing readings as well as dosing information, as required. Said display unit may further include an ammeter and/or a voltage adjuster.

Optionally, the inventive pharmaceutical device, especially when provided as an integrated pharmaceutical device in a single device, may also include a timing unit such as a timing circuit, which will activate the device at selected intervals or give a signal in the form of a bleep which will prompt the user to activate the device at selected intervals of time. However, the inventive device can also be used for continuous administration of Tapentadol or of the physiolo-gi-cally acceptable salt thereof.

In a preferred embodiment of the present invention, the inventive device is specifically designed and intended for delivery of Tapentadol or of the physiologically acceptable salt thereof and is co-packaged or co-promoted with the Tapentadol or of the physiolo-gi-cally acceptable salt thereof and sold as a system intended only for delivery of that drug. Importantly, delivery parameters such as current level, drug selection, drug concentration, etc., which may affect the safety or efficacy of the device, are fixed and cannot be altered by the user. Such devices only need to be removed from packaging and applied to the skin where localized treatment is needed.

In a preferred embodiment of the present invention, the inventive pharmaceutical device is for dermal, preferably transdermal, administration of Tapentadol or of a physiolo-gi-cally acceptable salt thereof.

In a particularly preferred embodiment of the present invention the inventive pharmaceutical device is a transdermal delivery system, in particular a patch.

The pharmacologically active ingredient contained in the pharmaceutical device according to the invention is Tapentadol and/or a physiologically acceptable salt thereof.

The free base of Tapentadol has the following structural formula (I):

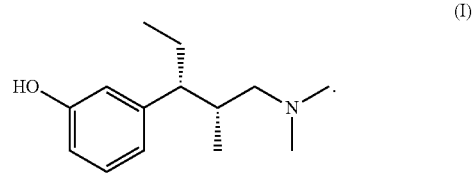 [SMILES: CC[C@@H](c1cccc(O)c1)[C@@H](C)CN(C)C]

(I)

For the purpose of specification, the term "Tapentadol" is intended to include (−)-[(1R,2R)-3-(3-dimethylamino-1-ethyl-2-methyl-propyl)]phenol in form of the free base, i.e. the compound according to formula (I) in any possible form including solvates, co-crystals and polymorphs, and its physiologically acceptable salts, in particular acid addition salts and corresponding solvates, co-crystals and polymorphs.

For the purpose of specification, doses of Tapentadol relate to the free base. Thus, when a physiologically acceptable salt is used instead, its dose has to be adapted to the equivalent dose of the free base. For example, a dose of "200 mg" means an amount of 200 mg of the free base or any equivalent amount of a physiologically acceptable salt or solvate corresponding to 200 mg of the free base (e.g. about 233 mg of the hydrochloride).

The pharmacologically active ingredient can be present in the pharmaceutical device according to the invention in form of the free base or as derivative thereof in any possible form, thereby particularly including solvates and polymorphs, salts, in particular acid addition salts and corresponding solvates and polymorphs.

The pharmacologically active ingredient can be present in the pharmaceutical device according to the invention in form of an acid addition salt, whereby any suitable acid capable of forming such an addition salt may be used. The conversion of the pharmacologically active ingredient into a corresponding addition salt, for example, via reaction with a suitable acid may be effected in a manner well known to those skilled in the art. Suitable physiologically acceptable salts include salts of inorganic acids, such as hydrochloric acid (Tapentadol HCl), hydrobromic acid and sulfuric acid, and salts of organic acids, such as methane sulfonic acid, fumaric acid, maleic acid, acetic acid, oxalic acid, succinic acid, malic acid, tartaric acid, mandelic acid, lactic acid, citric acid, glutamic acid, acetylsalicylic acid, nicotinic acid, aminobenzoic acid, α-liponic acid, hippuric acid and asparaginic acid. The preferred salt is the hydrochloride salt of Tapentadol.

The pharmacologically active ingredient can also be present in the pharmaceutical device according to the invention in form of the free base. However, preferably, in this case the drug reservoir (3) comprising the free base of Tapentadol additionally comprises a proton donating compound such as acid in order to adjust the pH value of the drug reservoir in that Tapentadol is provided in charged form.

In the following, unless expressly stated otherwise, all weight percentages relate to the total weight of the pharmaceutical device or to the total weight of a specific layer or reservoir thereof.

The inventive device comprises at least one drug reservoir (3) containing at least a portion of the Tapentadol or a physiologically acceptable salt thereof. Thus, the inventive device may comprise a single drug reservoir (3) or a plurality of single drug reservoirs (3), e.g. arranged in an array such as a honeycomb array. Preferably, the inventive device contains a single drug reservoir (3).

In case the inventive device is an electrophoretic device, the at least one pair of electrodes consisting of an active electrode (1a) and a counter electrode (2a) are preferably in contact with or integrated within the drug reservoir (3), preferably in order to provide a closed electric circuit within the device.

In case the inventive device is an iontophoretic device, of the at least one pair of electrodes consisting of an active electrode (1b) and a counter electrode (2b), the active electrode (1b) is preferably in contact with or integrated within the drug reservoir (3), and the counter electrode (2b) is preferably in contact with or integrated within an additional reservoir (15), preferably in each case in order to provide a closed electric circuit. Said additional reservoir (15) preferably comprises a conductive medium, more preferably comprises an aqueous medium, such as a gel, preferably a hydrogel. The same materials such as gel or hydrogels, which can be used for providing the drug reservoir (3) can also be used to provide the additional reservoir (15). Preferably, the additional reservoir (15) further comprises a suitable ion source, e.g. for chloride ions, such as sodium chloride.

In case the inventive device is a combined electrophoretic and iontophoretic device, of the at least one pair of electrodes consisting of an active electrode and a counter electrode (1a and 2a and/or 1b and 2b), and the optionally at least one additional electrode as auxiliary electrode, the active electrode (1b) is preferably in contact with or integrated within the drug reservoir (3), and the counter electrode (2b) is preferably in contact with or integrated within an additional reservoir (15), preferably in each case in order to provide a closed electric circuit. Said additional reservoir (15) preferably comprises a conductive medium, more preferably comprises an aqueous medium, such as a gel, preferably a hydrogel. The same materials such as gel or hydrogels, which can be used for providing the drug reservoir (3) can also be used to provide the additional reservoir (15). Preferably, the additional reservoir (15) further comprises a suitable ion source, e.g. for chloride ions, such as sodium chloride.

The drug reservoir (3) of the inventive device comprises at least a portion of the total amount of Tapentadol or of a physiologically acceptable salt thereof that is contained in the pharmaceutical device.

Preferably, the drug reservoir (3) comprises at least 10 wt.-%, more preferably at least 25 wt.-%, still more preferably at least 50 wt.-%, yet more preferably at least 75 wt.-%, even more preferably at least 85 wt.-%, most preferably at least 90 wt.-%, and in particular at least 95 wt.-% of the total amount of Tapentadol or of a physiologically acceptable salt thereof, that is contained in the pharmaceutical device.

Preferably, the majority of Tapentadol or of a physiologically acceptable salt thereof is contained in the drug reservoir (3), while a certain portion of Tapentadol or of a physiologically acceptable salt thereof may be contained in any optional further optionally adjacent layers of the inventive device such as an adhesive layer (4a) and/or (8), e.g. due to migration and/or diffusion processes.

In particular, however, the drug reservoir (3) comprises the total amount of Tapentadol or of a physiologically acceptable salt thereof that is contained in the pharmaceutical device.

Preferably, the drug reservoir (3) of the inventive device contains Tapentadol in form of a physiologically acceptable salt thereof, more preferably it contains Tapentadol in form of one of its acid addition salts, in particular in form of its hydrochloride salt.

The drug reservoir (3) of the inventive device, which comprises at least a portion of the total amount of Tapentadol or of a physiologically acceptable salt thereof, can be any material adapted to absorb and hold a sufficient quantity of a liquid and/or a semisolid and/or a solid polymer matrix, therein in order to permit transport of Tapentadol or of a physiologically acceptable salt thereof there through.

Preferably, the drug reservoir (3) comprises a conductive medium, more preferably comprises an aqueous medium, such as a gel, preferably a hydrogel.

Preferably, the drug reservoir (3) of the inventive device comprises a liquid, e.g. a medium such as a solution or a suspension, preferably an aqueous medium such as an aqueous solution or suspension, a semisolid such as a gel, or a solid polymer matrix, or any mixtures thereof, for example a gel containing a preferably aqueous solution or suspension.

In case the drug reservoir (3) comprises an aqueous medium, such as a hydrogel, partial electrolysis of water takes place upon electric-field assisted administration, e.g. in case a positively charged Tapentadol molecule such as Tapentadol hydrochloride is used, a reduction of water takes place at the counter electrode ($2H_2O+2e-$ to $H2+2OH-$) and an oxidation of water takes place at the active electrode ($2H_2O$ to $4H++O2+4e-$). In case silver electrodes are used as at least one pair of electrodes consisting of an active electrode and a counter electrode (1a and 2a and/or 1b and 2b), the oxidation of water at the active electrode is preferably suppressed as long as enough silver chloride can be deposited at the active electrode ($Ag+Cl-$ to $AgCl+e-$).

Preferably, the drug reservoir (3) comprises also an electrolyte reservoir, preferably a counter electrolyte reservoir, more preferably a counter electrolyte reservoir comprising chloride ions, i.e. such an electrolyte reservoir may be integrated within the drug reservoir (3). For example, if Tapentadol hydrochloride is used, chloride ions are provided as counter ions within the drug reservoir. Alternatively, the electrolyte reservoir may be separated from the drug reservoir (3). The electrolyte reservoir may be present in form of a liquid, e.g. a medium such as a solution or a suspension, preferably an aqueous medium such as an aqueous solution or suspension, or in any mixture thereof, for example in form of a gel containing preferably aqueous solution or suspension.

In case the drug reservoir (3) and/or the electrolyte reservoir comprise(s) a liquid, e.g. an aqueous medium, said liquid may contain at least in part, one or more hydrophilic polymers. Hydrophilic polymers are typically preferred since water is the preferred ion transport medium and hydrophilic polymers have been demonstrated to have a sufficient equilibrium water content.

In case the drug reservoir (3) and/or the electrolyte reservoir comprises a semisolid, e.g. a gel, or a mixture of a liquid such an aqueous medium and a semisolid such as gel, said gel is preferably based on a hydrophilic polymer which is insoluble or soluble, preferably insoluble, in water. The hydrophilic polymers employed can be linear or cross-linked. Suitable hydrophilic polymers are selected from the group consisting of co-polyesters, polyvinylpyrrolidones, polyvinyl alcohols, polyalkylene oxides such as polyethylene oxides and polypropylene oxides, blends of polyoxyethylene or polyethylene glycols with poly(meth)acrylic acid, polyethylene glycols, polypropylene glycols, copolymers of polyethylene glycol and polypropylene glycol (e.g. poloxamers), polyacrylamides, cross-linked dextran, cellulose derivatives such as hydroxyethyl cellulose, hydroxypropylmethylcellulose, hydroxypropylcellulose, and cross-linked Na-carboxymethylcellulose, hydrogels such as polyhydroxyethyl methacrylate, natural gums, chitosan, pectin, starch, guar gum, locust bean gum, and the like, along with blends thereof. Optionally, hydrophobic polymer may be present, to improve structural integrity of the gels or hydrogels. Suitable hydrophobic polymers are selected from the group consisting of polyisobutylenes, polyethylenes, polypropylenes, polyisoprenes and polyalkenes, rubbers, polyvinylacetate, ethylene vinyl acetate copolymers, polyamides such as nylons, polyurethanes, polyvinylchloride, acrylic or methacrylic resins such as polymers of esters of acrylic or methacrylic acid with alcohols such as n-butanol, 1-methyl pentanol, 2-methyl pentanol, 3-methyl pentanol, 2-ethyl butanol isooctanol, n-decanol, alone or copolymerized with ethylenically unsaturated monomers such as acrylic acid, methacrylic acid, acrylamide, methacrylamide, N-alkoxymethyl acrylamides, N-alkoxymethyl methacrylamides, N-tert-butylacrylamide, itaconic acid, N-branched alkyl maleamic acids, wherein the alkyl group has 10-24 carbon atoms, glycol diacrylates, and blends thereof.

In case the drug reservoir (3) comprises a solid polymer matrix, said matrix can be composed at least in part, of at least one hydrophilic polymer. Matrices derived from insoluble hydrophilic polymers are preferred over soluble hydrophilic polymers. The solid polymer matrix may also be present in a liquid such an aqueous medium. The same hydrophilic polymers may be employed which can be used for the preparation of gels as listed hereinbefore. Further, the matrices may comprise at least one hydrophobic polymer. The same hydrophobic polymers may be employed which can be used for the preparation of gels as listed hereinbefore.

In a particular preferred embodiment, the drug reservoir (3) comprises a liquid, e.g. a medium such as a solution or a suspension, preferably an aqueous medium such as an aqueous solution or suspension, in particular an aqueous solution containing Tapentadol and/or a physiologically acceptable salt thereof.

In another particular preferred embodiment, the drug reservoir (3) of the inventive device comprises a semisolid, more preferably a gel, in particular in a hydrogel, i.e. the drug reservoir (3) comprises a hydrogel. In particular, the drug reservoir (3) comprises a gel or hydrogel and/or an aqueous medium.

Preferably, the liquid and/or semisolid, e.g. the gel or hydrogel and/or an aqueous medium of the drug reservoir (3) has an initial pH value, i.e. a pH value before any electrical potential (Va and/or Vb) is applied, within the range of from 1 to 10, more preferably within the range of from 2 to 9, even more preferably within the range of from 3 to 8, in particular in of from 4 to 7.5, most preferred within the range of from 5 to 7.5. Lowering the pH value may be achieved by addition of any conventional acid such as acetic acid, hydrochloric acid, citric acid, sorbic acid or phosphoric acid. Adjusting the pH value may be achieved by using any conventional buffer such as an acetic acid/acetate buffer, a phosphoric acid/phosphate buffer, a citric acid/citrate buffer or a sulfuric acid/sulfate buffer or a hydrochloric acid/chloride buffer. Preferably, the drug reservoir (3) comprises at least one buffer system, preferably at least one buffer system selected from the group consisting of an acetic acid/acetate buffer, a phosphoric acid/phosphate buffer, a citric acid/citrate buffer, a sulfuric acid/sulfate buffer and a hydrochloric acid/chloride buffer.

Preferably, the drug reservoir (3) of the inventive device is integrated into a drug layer (14), i.e. preferably the inventive device comprises a drug layer (14) comprising the drug reservoir (3).

Preferably, the inventive device further comprises at least one barrier material (10), which is preferably integrated in drug layer (14), which in turn comprises the drug reservoir (3). Preferably, the drug reservoir (3) is bordered on at least two of its sides by a barrier material (10), preferably on the two sides which are substantially perpendicular to the adhesive layer (4a) and/or surface layer (7). Alternatively, the drug reservoir (3), preferably within a drug layer (14), can be surrounded by a barrier material (10) in form of a ring. Preferably, the barrier material (10) provides a barrier for the Tapentadol and/or a physiologically acceptable salt thereof containing drug reservoir (3) in order to prevent its/their migration out of the drug reservoir (3) into other parts of the inventive device with the exception of the means (4), e.g. with the exception of adhesive layer (4a).

Thus, the inventive device preferably comprises a drug layer (14), which in turn preferably comprises at least one drug reservoir (3) and at least one barrier material (10).

In a preferred embodiment, the barrier material (10) comprises one or more polymers selected from the group consisting of polyurethanes, polyester elastomers, polyether block amides, polyacrylates, ethylene vinyl acetates, ethylene acrylate copolymers, ionomer resins, polyvinyl chloride, polyvinylidene chloride, polyesters such as polyterephthalates, and polyolefins, such as polyethylene; polyolefins, in particular polyethylene, polyesters, ethylene vinylacetate copolymers and polyurethanes are particularly preferred. The barrier material may also be based on or comprise polytetrafluoroethylene (teflon).

The barrier material (10) may be a layer, a plurality of layers or a laminate, preferably comprising a polymer film, such as a polyester film, or may be in the form of a ring The inventive device may further comprise a foam ring (9), preferably as part of drug layer (14), in which the drug reservoir (3), preferably including the barrier material (10) is at least partly recessed. The foam ring (9) is preferably provided in order to facilitate the preparation of the inventive device.

Any suitable material may be employed for the preparation of the foam ring (9) such as any foamed polymers selected from the group consisting of polyurethanes, polyester elastomers, polyether block amides, polyacrylates, ethylene vinyl acetates, ethylene acrylate copolymers, ionomer resins, polyvinyl chloride, polyvinylidene chloride, polyesters such as polyterephthalates, and polyolefins, such as polyethylene; and mixtures thereof; polyolefins, in particular polyethylene, polyesters, ethylene vinylacetate copolymers and polyurethanes are particularly preferred.

The thickness of the foam ring (9) is not particularly limited and may depend upon a number of factors such as content of Tapentadol or a physiologically acceptable salt thereof and excipients within the device, prescribed duration of application of pharmaceutical device on the skin, and the like.

Preferably, the foam ring (9) has a thickness within the range of from 1.0 to 1500 µm, more preferably within the range of from 5.0 to 1000 µm.

In a preferred embodiment, the foam ring (9) has a thickness within the range of from 50±35 µm (i.e. from 15 µm to 85 µm), more preferably 50±30 µm, still more preferably 50±25 µm, yet more preferably 50±20 µm, even more preferably 50±15 µm, most preferably 50±10 µm, and in particular 50±5 µm. In another preferred embodiment, the foam ring (9) has a thickness within the range of from 75±70 µm, more preferably 75±60 µm, still more preferably 75±50 µm, yet more preferably 75±40 µm, even more preferably 75±30 µm, most preferably 75±20 µm, and in particular 75±10 µm. In still another preferred embodiment, the foam ring (9) has a thickness within the range of from 100±70 µm, more preferably 100±60 µm, still more preferably 100±50 µm, yet more preferably 100±40 µm, even more preferably 100±30 µm, most preferably 100±20 µm, and in particular 100±10 µm. In yet another preferred embodiment, the foam ring (9) has a thickness within the range of from 200±175 µm, more preferably 200±150 µm, still more preferably 200±125 µm, yet more preferably 200±100 µm, even more preferably 200±75 µm, most preferably 200±50 µm, and in particular 200±25 µm. In a further preferred embodiment, the foam ring (9) has a thickness within the range of from 300±175 µm, more preferably 300±150 µm, still more preferably 300±125 µm, yet more preferably 300±100 µm, even more preferably 300±75 µm, most preferably 300±50 µm, and in particular 300±25 µm. In still a further preferred embodiment, the foam ring (9) has a thickness within the range of from 400±175 µm, more preferably 400±150 µm, still more preferably 400±125 µm, yet more preferably 400±100 µm, even more preferably 400±75 µm, most preferably 400±50 µm, and in particular 400±25 µm. In yet a further preferred embodiment, the foam ring (9) has a thickness within the range of from 500±175 µm, more preferably 500±150 µm, still more preferably 500±125 µm, yet more preferably 500±100 µm, even more preferably 500±75 µm, most preferably 500±50 µm, and in particular 500±25 µm. In yet another further preferred embodiment, the foam ring (9) has a thickness within the range of from 700±200 µm, more preferably 700±150 µm, still more preferably 700±125 µm, yet more preferably 700±100 µm, even more preferably 700±75 µm, most preferably 700±50 µm, and in particular 700±25 µm. In yet another further preferred embodiment, the foam ring (9) has a thickness within the range of from 900±200 µm, more preferably 900±150 µm, still more preferably 900±125 µm, yet more preferably 900±100 µm, even more preferably 900±75 µm, most preferably 900±50 µm, and in particular 900±25 µm.

The foam ring (9) is preferably integrated within drug layer (14) of the inventive device. Thus, the inventive device preferably comprises a drug layer (14), which in turn preferably comprises at least one drug reservoir (3) and at least one barrier material (10) and at least one foam ring (9).

Optionally, the drug reservoir (3), an additional reservoir (15), and/or an electrolyte reservoir such as a counter electrolyte reservoir as well as an adhesive layer (4a) and an optionally present drug layer (14) comprising the drug reservoir (3) may contain at last one further additive selected from the group consisting of fillers, percutaneous penetration enhancers, crystallization inhibitors, antioxidants, and the like, although the presence of percutaneous penetration enhancers, which further enhances percutaneous penetration and permeation of the pharmacologically active ingredient through human skin, is not necessary due to the electric-field assisted administration. Thus, in a preferred embodiment the inventive device does not contain any penetration enhancers such as percutaneous penetration enhancers.

The total dose of the pharmacologically active ingredient that is contained in the pharmaceutical device is not particularly limited and may depend upon various factors such as body weight of the subject to be treated and duration of application on the skin. The pharmacologically active ingredient is contained in the pharmaceutical device in a therapeutically effective amount. The amount that constitutes a therapeutically effective amount varies according to the form of the pharmacologically active ingredient being present, the condition being treated, the severity of said condition, the patient being treated, and the prescribed duration of application of the pharmaceutical device to the skin.

Preferably, the concentration of Tapentadol and/or of a physiologically acceptable salt thereof as the pharmacologically active ingredient in the drug reservoir (3) is in the range of from at least 0.5 to 20.0 wt.-%, more preferably in the range of from at least 0.6 to 17.0 wt.-%, still more preferably in the range of from at least 0.7 to 12.0 wt.-%, most preferably in the range of from at least 0.8 to 10.0 wt.-%, and in particular in the range of from at least 1.0 to 8.0 wt.-%, based on the total weight of the drug reservoir (3).

In a preferred embodiment, the concentration of the pharmacologically active ingredient in the drug reservoir (3) is at least 0.5 wt.-%, more preferably at least 0.6 wt.-%, still more preferably at least 0.7 wt.-%, yet more preferably at least 0.8 wt.-%, most preferably at least 0.9 wt.-% and in particular at least 1.0 wt.-%, relative to the total weight of the drug reservoir (3). In another preferred embodiment, the concentration of the pharmacologically active ingredient in the drug reservoir (3) is at least 1.0 wt.-%, more preferably at least 1.2 wt.-%, still more preferably at least 1.4 wt.-%, yet more preferably at least 1.6 wt.-%, even more preferably at least 1.8 wt.-%, and in particular at least 2.0 wt.-%, relative to the total weight of the drug reservoir (3). In still another preferred embodiment, the concentration of the pharmacologically active ingredient in the drug reservoir (3) is at least 2.0 wt.-%, more preferably at least 2.2 wt.-%, still more preferably at least 2.4 wt.-%, yet more preferably at least 2.6 wt.-%, even more preferably at least 2.8 wt.-%, and in particular at least 3.0 wt.-%, relative to the total weight of the drug reservoir (3). In yet another preferred embodiment, the concentration of the pharmacologically active ingredient in the drug reservoir (3) is at least 3.0 wt.-%, more preferably at least 3.1 wt.-%, still more preferably at least 3.2 wt.-%, yet more preferably at least 3.3 wt.-%, even more preferably at least 3.4 wt.-%, and in particular at least 3.5 wt.-%, relative to the total weight of the drug reservoir (3). In a further preferred embodiment, the concentration of the pharmacologically active ingredient in the drug reservoir (3) is at least 3.5 wt.-%, more preferably at least 3.7 wt.-%, still more preferably at least 3.9 wt.-%, yet more preferably at least 4.1 wt.-%, even more preferably at least 4.3 wt.-%, and in particular at least 4.5 wt.-%, relative to the total weight of the drug reservoir (3). In still a further preferred embodiment, the concentration of the pharmacologically active ingredient in the drug reservoir (3) is at least 4.5 wt.-%, more preferably at least 5.0 wt.-%, relative to the total weight of the drug reservoir (3).

For the purpose of the present invention, the term "delivered" preferably represents the total amount of the pharmacologically active ingredient released from the inventive device to the skin during the application period such as the wear period, and preferably is an amount greater than the total amount of the pharmacologically active ingredient that reaches the systemic blood circulation. The amount delivered is conventionally measured by comparison of the amount of the pharmacologically active ingredient initially loaded into the device to the final contents of the device following removal of the device.

Preferably, by administration of Tapentadol and/or a physiologically acceptable salt thereof by using the inventive device, a transport number (tT) of Tapentadol and/or a physiologically acceptable salt thereof within in the range of from 0.01 to 1.00, more preferably within in the range of from 0.03 to 0.80, even more preferably within in the range of from 0.05 to 0.60, still more preferably within in the range of from 0.07 to 0.40, yet more preferably within in the range of from 0.09 to 0.20, in particular within in the range of from 0.10 to 0.15 can be achieved, in particular in case the inventive device is a iontophoretic device.

Figure 10:
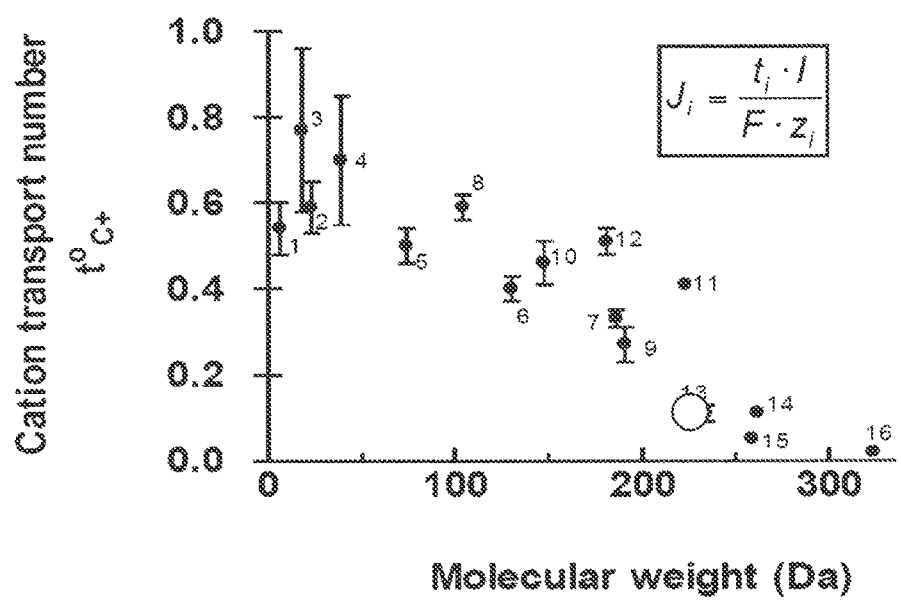
FIG. 10 is a graphical representation of the determination of the transport number of Tapentadol by iontophoretic delivery.

A person skilled in the art is aware of the term "transport number" (tT), e.g. from B. Mudry, R. H. Guy, M. B. Delgado-Charro, Biophys. J., 2006, 90, pages 2822-2830, B. Mudry, R. H. Guy, M. B. Delgado-Charro J. Control. Release 2006, 111, pages 362-367 and B. Mudry, R. H. Guy, M. B. Delgado-Charro, J. Pharm. Sci. 2006, 95, pages 561-569, which preferably means the fraction (IT) of the total current (I) carried by Tapentadol and/or a physiologically acceptable salt thereof (tT=IT/I). Said transport number can be calculated from the drug flux (JT), i.e. the permeation performance, of Tapentadol or a physiologically acceptable salt thereof, which can be determined by the total current passed (tT=JT·F·z/I, with JT=drug flux, tT=transport number, I=total current, F=Faraday constant, zT=charge number) as indicated in FIG. 10.

In a preferred embodiment, the inventive pharmaceutical device contains the pharmacologically active ingredient in a quantity so that during 24 hours of consecutive application of an electric field (Fa and/or Fb), and application to the skin, an amount of 20±18 mg (i.e. from 2 mg to 38 mg), more preferably 20±17 mg, still more preferably 20±16 mg, most preferably 20±15 mg, and in particular 20±14 mg is delivered to the skin per cm2 device area, preferably per cm2 patch area, in particular in case the inventive device is a iontophoretic and/or a combined electrophoretic and iontophoretic device.

In another preferred embodiment, the inventive pharmaceutical device contains the pharmacologically active ingredient in a quantity so that during 24 hours of consecutive application of an electric field (Fa and/or Fb), and application to the skin, an amount of 10.0±9.9 mg (i.e. from 0.1 mg to 19.8 mg), more preferably 10.0±9.7 mg, still more preferably 10.0±9.5 mg, most preferably 10.0±9.3 mg, and in particular 10.0±9.1 mg is delivered to the skin per cm2 device area, preferably per cm2 patch area, in particular in case the inventive device is a iontophoretic and/or a combined electrophoretic and iontophoretic device.

In another preferred embodiment, the inventive pharmaceutical device contains the pharmacologically active ingredient in a quantity so that during 24 hours of consecutive application of an electric field (Fa and/or Fb), and application to the skin, an amount of at least 2.0 mg, more preferably at least 3.0 mg, still more preferably at least 4.0 mg, even more preferably at least 5.0 mg, yet even more preferably at least 6.0 mg and in particular at least 7.0 mg, and most preferred at least 8.0 mg is delivered to the skin per cm2 device area, preferably per cm2 patch area, in particular in case the inventive device is a iontophoretic and/or a combined electrophoretic and iontophoretic device.

In a preferred embodiment, the pharmaceutical device contains the pharmacologically active ingredient in a quantity so that during 12 hours or during 24 hours or during 48 hours or during 72 hours or during 96 hours or even during 168 hours of application of a single inventive device or of consecutive application of a series of inventive devices to the skin (5), i.e. under steady state conditions taking into account the depot effect of the skin, an amount of 20±15 mg (i.e. from 5 mg to 35 mg), more preferably 20±12.5 mg, still more preferably 20±10 mg, most preferably 20±7.5 mg, and in particular 20±5 mg is systemically administered per day. In still another preferred embodiment, the pharmaceutical device contains the pharmacologically active ingredient in a quantity so that during 12 hours or during 24 hours or during 48 hours or during 72 hours or during 96 hours or even during 168 hours of application of a single inventive device or of consecutive application of a series of inventive devices to the skin (5), i.e. under steady state conditions taking into account the depot effect of the skin, an amount of 50±40 mg, more preferably 50±35 mg, still more preferably 50±30 mg, yet more preferably 50±25 mg, even more preferably 50±20 mg, most preferably 50±15 mg, and in particular 50±10 mg is systemically administered per day. In yet another preferred embodiment, the pharmaceutical device contains the pharmacologically active ingredient in a quantity so that during 12 hours or during 24 hours or during 48 hours or during 72 hours or during 96 hours or even during 168 hours of application of a single inventive device or of consecutive application of a series of inventive devices to the skin (5), i.e. under steady state conditions taking into account the depot effect of the skin, an amount of 75±65 mg, more preferably 75±55 mg, still more preferably 75±45 mg, yet more preferably 75±35 mg, even more preferably 75±25 mg, most preferably 75±20 mg, and in particular 75±10 mg is systemically administered per day. In a further preferred embodiment, the pharmaceutical device contains the pharmacologically active ingredient in a quantity so that during 12 hours or during 24 hours or during 48 hours or during 72 hours or during 96 hours or even during 168 hours of application of a single inventive device or of consecutive application of a series of inventive devices to the skin (5), i.e. under steady state conditions taking into account the depot effect of the skin, an amount of 100±90 mg, more preferably 100±80 mg, still more preferably 100±60 mg, yet more preferably 100±50 mg, even more preferably 100±40 mg, most preferably 100±30 mg, and in particular 100±20 mg is systemically administered per day. In still a further preferred embodiment, the pharmaceutical device contains the pharmacologically active ingredient in a quantity so that during 12 hours or during 24 hours or during 48 hours or during 72 hours or during 96 hours or even during 168 hours of application of a single inventive device or of consecutive application of a series of inventive devices to the skin (5), i.e. under steady state conditions taking into account the depot effect of the skin, an amount of 150±140 mg, more preferably 150±120 mg, still more preferably 150±100 mg, yet more preferably 150±80 mg, even more preferably 150±60 mg, most preferably 150±40 mg, and in particular 150±20 mg is systemically administered per day. In yet a further preferred embodiment, the pharmaceutical device contains the pharmacologically active ingredient in a quantity so that during 12 hours or during 24 hours or during 48 hours or during 72 hours or during 96 hours or even during 168 hours of application of a single inventive device or of consecutive application of a series of inventive devices to the skin (5), i.e. under steady state conditions taking into account the depot effect of the skin, an amount of 200±180 mg, more preferably 200±150 mg, still more preferably 200±120 mg, yet more preferably 200±90 mg, even more preferably 200±70 mg, most preferably 200±40 mg, and in particular 200±20 mg is systemically administered per day. In another preferred embodiment, the pharmaceutical device contains the pharmacologically active ingredient in a quantity so that during 12 hours or during 24 hours or during 48 hours or during 72 hours or during 96 hours or even during 168 hours of application of a single inventive device or of consecutive application of a series of inventive devices to the skin (5), i.e. under steady state conditions taking into account the depot effect of the skin, an amount of 300±270 mg, more preferably 300±220 mg, still more preferably 300±170 mg, yet more preferably 300±120 mg, even more preferably 300±80 mg, most preferably 300±50 mg, and in particular 300±20 mg is systemically administered per day. In still another preferred embodiment, the pharmaceutical device contains the pharmacologically active ingredient in a quantity so that during 12 hours or during 24 hours or during 48 hours or during 72 hours or during 96 hours or even during 168 hours of application of a single inventive device or of consecutive application of a series of inventive devices to the skin (5), i.e. under steady state conditions taking into account the depot effect of the skin, an amount of 400±350 mg, more preferably 400±300 mg, still more preferably 400±250 mg, yet more preferably 400±200 mg, even more preferably 400±150 mg, most preferably 400±100 mg, and in particular 400±50 mg is systemically administered per day. In yet another preferred embodiment, the pharmaceutical device contains the pharmacologically active ingredient in a quantity so that during 12 hours or during 24 hours or during 48 hours or during 72 hours or during 96 hours or even during 168 hours of application of a single inventive device or of consecutive application of a series of inventive devices to the skin (5), i.e. under steady state conditions taking into account the depot effect of the skin, an amount of 500±450 mg, more preferably 500±350 mg, still more preferably 500±250 mg, yet more preferably 500±150 mg, even more preferably 500±100 mg, most preferably 500±75 mg, and in particular 500±50 mg is systemically administered per day. In a further preferred embodiment, the pharmaceutical device contains the pharmacologically active ingredient in a quantity so that during 12 hours or during 24 hours or during 48 hours or during 72 hours or during 96 hours or even during 168 hours of application of a single inventive device or of consecutive application of a series of inventive devices to the skin (5), i.e. under steady state conditions taking into account the depot effect of the skin, an amount of 600±400 mg, more preferably 600±300 mg, still more preferably 600±200 mg, yet more preferably 600±150 mg, even more preferably 600±100 mg, most preferably 600±75 mg, and in particular 600±50 mg is systemically administered per day.

Preferably, the total dose of the pharmacologically active ingredient that is contained in the pharmaceutical device satisfies the following requirement:

$$\text{dose contained in patch [mg]} = \frac{\text{intended duration of application [days]} \cdot \text{desired systemic daily dose [mg]}}{\text{bioavailability [\%]}} \cdot 100$$

In a preferred embodiment, the desired systemic daily dose amounts to 20±15 mg (i.e. from 5 mg to 35 mg), more preferably 20±10 mg; or 50±20 mg, more preferably 50±10 mg; or 75±40 mg, more preferably 75±20 mg; or 100±80 mg, more preferably 100±40 mg; or 150±100 mg, more preferably 150±50 mg; or 200±150 mg, more preferably 200±75 mg; or 300±180 mg, more preferably 300±80 mg; or 400±200 mg, more preferably 400±100 mg; or 500±300 mg, more preferably 500±150 mg; or 600±350 mg, more preferably 600±100 mg. The intended duration of application is preferably 1, 2, 3, 4, 5, 6, or 7 days. The bioavailability is preferably as high as possible and can be determined for a given pharmaceutical device by routine experimentation.

Preferably, the transdermal bioavailability is within the range of from 1 to 100%.

In a preferred embodiment, the transdermal bioavailability is within the range of 5.0±4.5% (i.e. from 0.5% to 9.5%), more preferably 5.0±4.0%, still more preferably 5.0±3.5%, yet more preferably 5.0±3.0%, even more preferably 5.0±2.5%, most preferably 5.0±2.0%, and in particular 5.0±1.5%. In another preferred embodiment, the transdermal bioavailability is within the range of 10±8%, more preferably 10±7%, still more preferably 10±6%, yet more preferably 10±5%, even more preferably 10±4%, most preferably 10±3%, and in particular 10±2%. In still another preferred embodiment, the transdermal bioavailability is within the range of 30±28%, more preferably 30±25%, still more preferably 30±22%, yet more preferably 30±18%, even more preferably 30±12%, most preferably 30±8%, and in particular 30±5%. In yet another preferred embodiment, the transdermal bioavailability is within the range of 50±45%, more preferably 50±35%, still more preferably 50±25%, yet more preferably 50±15%, even more preferably 50±10%, most preferably 50±8%, and in particular 50±5%. In a further preferred embodiment, the transdermal bioavailability is within the range of 70±65%, more preferably 70±55%, still more preferably 70±45%, yet more preferably 70±35%, even more preferably 70±25%, most preferably 70±15%, and in particular 70±5%. In still a further preferred embodiment, the transdermal bioavailability is within the range of 95±75%, more preferably 95±60%, still more preferably 95±45%, yet more preferably 95±35%, even more preferably 95±25%, most preferably 95±15%, and in particular 95±5%.

Preferably, the pharmaceutical device upon application to the human skin provides over a period of at least 6 hours, more preferably at least 12 hours, even more preferably of at least 24 hours, release of the pharmacologically active ingredient at a rate in the range of from at least 1.0 to 100,000 µg·cm−2·h−1.

In a preferred embodiment, the pharmaceutical device upon application to the human skin provides over a period of at least 6 hours, more preferably at least 12 hours, even more preferably of at least 24 hours, release of the pharmacologically active ingredient at a rate of at least 1.0 µg·cm−2·h−1 or at least 5.0 µg·cm−2·h−1 or at least 10 µg·cm−2·h−1; more preferably at least 20 µg·cm−2·h−1 or at least 40 µg·cm−2·h−1 or at least 60 µg·cm−2·h−1; still more preferably at least 80 µg·cm−2·h−1 or at least 100 µg·cm−2·h−1 or at least 120 µg·cm−2·h−1; yet more preferably at least 150 µg·cm−2·h−1 or at least 250 µg·cm−2·h−1 or at least 350 µg·cm−2·h−1; and in particular at least 500 µg·cm−2·h−1 or at least 1,000 µg·cm−2·h−1 or at least 10,000 µg·cm−2·h−1, or at least 100,000 µg·cm−2·h−1

In a preferred embodiment, the pharmaceutical device upon application to the human skin provides over a period of at least 6 hours, more preferably at least 12 hours, even more preferably of at least 24 hours, release of the pharmacologically active ingredient at a rate of 10±8 µg·cm−2·h−1 (i.e. from 2 µg·cm−2·h−1 to 18 µg·cm−2·h−1), more preferably 10±7 µg·cm−2·h−1, still more preferably 10±6 µg·cm−2·h−1, yet more preferably 10±5 µg·cm−2·h−1, even more preferably 10±4 µg·cm−2·h−1, most preferably 10±3 µg·cm−2·h−1 and in particular 10±2 µg·cm−2·h−1. In another preferred embodiment, the pharmaceutical device upon application to the human skin provides over a period of at least 6 hours, more preferably at least 12 hours, even more preferably of at least 24 hours, release of the pharmacologically active ingredient at a rate of 50±45 µg·cm−2·h−1, more preferably 50±35 µg·cm−2·h−1, still more preferably 50±30 µg·cm−2·h−1, yet more preferably 50±25 µg·cm−2·h−1, even more preferably 50±20 µg·cm−2·h−1, most preferably 50±15 µg·cm−2·h−1 and in particular 50±10 µg·cm−2·h−1. In still another preferred embodiment, the pharmaceutical device upon application to the human skin provides over a period of at least 6 hours, more preferably at least 12 hours, even more preferably of at least 24 hours, release of the pharmacologically active ingredient at a rate of 100±80 µg·cm−2·h−1, more preferably 100±70 µg·cm−2·h−1, still more preferably 100±60 µg·cm−2·h−1, yet more preferably 100±50 µg·cm−2·h−1, even more preferably 100±40 µg·cm−2·h−1, most preferably 100±30 µg·cm−2·h−1 and in particular 100±20 µg·cm−2·h−1. In yet another preferred embodiment, the pharmaceutical device upon application to the human skin provides over a period of at least 6 hours, more preferably at least 12 hours, even more preferably of at least 24 hours, release of the pharmacologically active ingredient at a rate of 150±100 µg·cm−2·h−1, more preferably 150±80 µg·cm−2·h−1, still more preferably 150±60 µg·cm−2·h−1, yet more preferably 150±50 µg·cm−2·h−1, even more preferably 150±40 µg·cm−2·h−1, most preferably 150±30 µg·cm−2·h−1 and in particular 150±20 µg·cm−2·h−1. In a further preferred embodiment, the pharmaceutical device upon application to the human skin provides over a period of at least 6 hours, more preferably at least 12 hours, even more preferably of at least 24 hours, release of the pharmacologically active ingredient at a rate of 300±250 µg·cm−2·h−1, more preferably 300±200 µg·cm−2·h−1, still more preferably 300±160 µg·cm−2·h−1, yet more preferably 300±120 µg·cm−2·h−1, even more preferably 300±100 µg·cm−2·h−1, most preferably 300±80 µg·cm−2·h−1 and in particular 300±50 µg·cm−2·h−1. In still a further preferred embodiment, the pharmaceutical device upon application to the human skin provides over a period of at least 6 hours, more preferably at least 12 hours, even more preferably of at least 24 hours, release of the pharmacologically active ingredient at a rate of 500±450 µg·cm−2·h−1, more preferably 500±350 µg·cm−2·h−1, still more preferably 500±300 µg·cm−2·h−1, yet more preferably 500±250 µg·cm−2·h−1, even more preferably 500±200 µg·cm−2·h−1, most preferably 500±150 µg·cm−2·h−1 and in particular 500±100 µg·cm−2·h−1. In yet a further preferred embodiment, the pharmaceutical device upon application to the human skin provides over a period of at least 6 hours, more preferably at least 12 hours, even more preferably of at least 24 hours, release of the pharmacologically active ingredient at a rate of 1,000±800 µg·cm−2·h−1, more preferably 1,000±700 µg·cm−2·h−1, still more preferably 1,000±600 µg·cm−2·h−1, yet more preferably 1,000±500 µg·cm−2·h−1, even more preferably 1,000±400 µg·cm−2·h−1, most preferably 1,000±300 µg·cm−2·h−1 and in particular 1,000±200 µg·cm−2·h−1. In another preferred embodiment, the pharmaceutical device upon application to the human skin provides over a period of at least 6 hours, more preferably at least 12 hours, even more preferably of at least 24 hours, release of the pharmacologically active ingredient at a rate of 10,000±8,000 µg·cm−2·h−1, more preferably 10,000±7,000 µg·cm−2·h−1, still more preferably 10,000±6,000 µg·cm−2·h−1, yet more preferably 10,000±5,000 µg·cm−2·h−1, even more preferably 10,000±4,000 µg·cm−2·h−1, most preferably 10,000±3,000 µg·cm−2·h−1 and in particular 10,000±2,000 µg·cm−2·h−1. In still another preferred embodiment, the pharmaceutical device upon application to the human skin provides over a period of at least 6 hours, more preferably at least 12 hours, even more preferably of at least 24 hours, release of the pharmacologically active ingredient at a rate of 100,000±80,000 µg·cm−2·h−1, more preferably 100,000±70,000 µg·cm−2·h−1, still more preferably 100,000±60,000 µg·cm−2·h−1, yet more preferably 100,000±50,000 µg·cm−2·h−1, even more preferably 100,000±40,000 µg·cm−2·h−1, most preferably 100,000±30,000 µg·cm−2·h−1 and in particular 100,000±20,000 µg·cm−2·h−1.

Low serum concentrations of Tapentadol suffice to show an effect in individuals that are relatively sensitive and higher serum concentrations of Tapentadol are needed to show an effect in persons that are relatively unsensitive. Preliminary clinical trials revealed that a significant pain treating effect is seen at serum concentrations in the range of from about 5 ng·ml-1 (approximately −2 mm visual analog scale (VAS) in a population mean) to about 300 ng·ml-1 (approximately −15 mm visual analog scale (VAS) in a population mean).

In a preferred embodiment, the pharmaceutical device according to the invention provides serum concentrations of the pharmacologically active ingredient over a period of at least 6 hours, more preferably at least 12 hours, even more preferably of at least 24 hours, upon repeated application to the human skin, i.e. under steady state conditions taking into account the depot effect of the skin, within the range of from 0.1 to 10,000 ng·ml-1, more preferably 1.0 to 9,000 ng·ml-1, still more preferably 2.0 to 8,000 ng·ml-1, yet more preferably 3.0 to 5,000 ng·ml-1, most preferably 4.0 to 500 ng·ml-1 and in particular 5.0 to 300 ng·ml-1.

In a preferred embodiment, the pharmaceutical device according to the invention provides serum concentrations of the pharmacologically active ingredient over a period of at least 6 hours, more preferably at least 12 hours, even more preferably of at least 24 hours, upon repeated application to the human skin, i.e. under steady state conditions taking into account the depot effect of the skin, of 10±8 ng·ml-1, more preferably 10±7 ng·ml-1, still more preferably 10±6 ng·ml-1, yet more preferably 10±5 ng·ml-1, even more preferably 10±4 ng·ml-1, most preferably 10±3 ng·ml-1, and in particular 10±2 ng·ml-1. In another preferred embodiment, the pharmaceutical device according to the invention provides serum concentrations of the pharmacologically active ingredient over a period of at least 6 hours, more preferably at least 12 hours, even more preferably of at least 24 hours, upon repeated application to the human skin, i.e. under steady state conditions taking into account the depot effect of the skin, of 20±16 ng·ml-1, more preferably 20±14 ng·ml-1, still more preferably 20±12 ng·ml-1, yet more preferably 20±10 ng·ml-1, even more preferably 20±8.0 ng·ml-1, most preferably 20±6.0 ng·ml-1, and in particular 20±4.0 ng·ml-1. In still another preferred embodiment, the pharmaceutical device according to the invention provides serum concentrations of the pharmacologically active ingredient over a period of at least 6 hours, more preferably at least 12 hours, even more preferably of at least 24 hours, upon repeated application to the human skin, i.e. under steady state conditions taking into account the depot effect of the skin, of 30±16 ng·ml-1, more preferably 30±14 ng·ml-1, still more preferably 30±12 ng·ml-1, yet more preferably 30±10 ng·ml-1, even more preferably 30±8.0 ng·ml-1, most preferably 30±7.0 ng·ml-1, and in particular 30±6.0 ng·ml-1. In yet another preferred embodiment, the pharmaceutical device according to the invention provides serum concentrations of the pharmacologically active ingredient over a period of at least 6 hours, more preferably at least 12 hours, even more preferably of at least 24 hours, upon repeated application to the human skin, i.e. under steady state conditions taking into account the depot effect of the skin, of 40±32 ng·ml-1, more preferably 40±28 ng·ml-1, still more preferably 40±24 ng·ml-1, yet more preferably 40±20 ng·ml-1, even more preferably 40±16 ng·ml-1, most preferably 40±12 ng·ml-1, and in particular 40±8.0 ng·ml-1. In a further preferred embodiment, the pharmaceutical device according to the invention provides serum concentrations of the pharmacologically active ingredient over a period of at least 6 hours, more preferably at least 12 hours, even more preferably of at least 24 hours, upon repeated application to the human skin, i.e. under steady state conditions taking into account the depot effect of the skin, of 50±35 ng·ml-1, more preferably 50±30 ng·ml-1, still more preferably 50±25 ng·ml-1, yet more preferably 50±20 ng·ml-1, most preferably 50±15 ng·ml-1, and in particular 50±10 ng·ml-1. In still a further preferred embodiment, the pharmaceutical device according to the invention provides serum concentrations of the pharmacologically active ingredient over a period of at least 6 hours, more preferably at least 12 hours, even more preferably of at least 24 hours, upon repeated application to the human skin, i.e. under steady state conditions taking into account the depot effect of the skin, of 60±45 ng·ml-1, more preferably 60±35 ng·ml-1, still more preferably 60±30 ng·ml-1, yet more preferably 60±25 ng·ml-1, even more preferably 60±20 ng·ml-1, most preferably 60±15 ng·ml-1, and in particular 60±10 ng·ml-1. In yet a further preferred embodiment, the pharmaceutical device according to the invention provides serum concentrations of the pharmacologically active ingredient over a period of at least 6 hours, more preferably at least 12 hours, even more preferably of at least 24 hours, upon repeated application to the human skin, i.e. under steady state conditions taking into account the depot effect of the skin, of 75±64 ng·ml-1, more preferably 75±56 ng·ml-1, still more preferably 75±48 ng·ml-1, yet more preferably 75±40 ng·ml-1, even more preferably 75±32 ng·ml-1, most preferably 75±24 ng·ml-1, and in particular 75±16 ng·ml-1. In another preferred embodiment, the pharmaceutical device according to the invention provides serum concentrations of the pharmacologically active ingredient over a period of at least 6 hours, more preferably at least 12 hours, even more preferably of at least 24 hours, upon repeated application to the human skin, i.e. under steady state conditions taking into account the depot effect of the skin, of 90±60 ng·ml-1, more preferably 90±50 ng·ml-1, still more preferably 90±40 ng·ml-1, yet more preferably 90±35 ng·ml-1, even more preferably 90±30 ng·ml-1, most preferably 90±25 ng·ml-1, and in particular 90±20 ng·ml-1. In still another preferred embodiment, the pharmaceutical device according to the invention provides serum concentrations of the pharmacologically active ingredient over a period of at least 6 hours, more preferably at least 12 hours, even more preferably of at least 24 hours, upon repeated application to the human skin, i.e. under steady state conditions taking into account the depot effect of the skin, of 150±128 ng·ml-1, more preferably 150±112 ng·ml-1, still more preferably 150±96 ng·ml-1, yet more preferably 150±80 ng·ml-1, even more preferably 150±64 ng·ml-1, most preferably 150±48 ng·ml-1, and in particular 150±32 ng·ml-1. In yet another preferred embodiment, the pharmaceutical device according to the invention provides serum concentrations of the pharmacologically active ingredient over a period of at least 6 hours, more preferably at least 12 hours, even more preferably of at least 24 hours, upon repeated application to the human skin, i.e. under steady state conditions taking into account the depot effect of the skin, of 300±256 ng·ml-1, more preferably 300±224 ng·ml-1, still more preferably 300±192 ng·ml-1, yet more preferably 300±160 ng·ml-1, even more preferably 300±128 ng·ml-1, most preferably 300±96 ng·ml-1, and in particular 300±64 ng·ml-1. In a further preferred embodiment, the pharmaceutical device according to the invention provides serum concentrations of the pharmacologically active ingredient over a period of at least 6 hours, more preferably at least 12 hours, even more preferably of at least 24 hours, upon repeated application to the human skin, i.e. under steady state conditions taking into account the depot effect of the skin, of 600±512 ng·ml-1, more preferably 600±448 ng·ml-1, still more preferably 600±384 ng·ml-1, yet more preferably 600±320 ng·ml-1, even more preferably 600±256 ng·ml-1, most preferably 600±192 ng·ml-1, and in particular 600±128 ng·ml-1. In still a further preferred embodiment, the pharmaceutical device according to the invention provides serum concentrations of the pharmacologically active ingredient over a period of at least 6 hours, more preferably at least 12 hours, even more preferably of at least 24 hours, upon repeated application to the human skin, i.e. under steady state conditions taking into account the depot effect of the skin, of 1,000±800 ng·ml-1, more preferably 1,000±700 ng·ml-1, still more preferably 1,000±600 ng·ml-1, yet more preferably 1,000±500 ng·ml-1, even more preferably 1,000±400 ng·ml-1, most preferably 1,000±300 ng·ml-1, and in particular 1,000±200 ng·ml-1. In yet a further preferred embodiment, the pharmaceutical device according to the invention provides serum concentrations of the pharmacologically active ingredient over a period of at least 6 hours, more preferably at least 12 hours, even more preferably of at least 24 hours, upon repeated application to the human skin, i.e. under steady state conditions taking into account the depot effect of the skin, of 10,000±8,000 ng·ml-1, more preferably 10,000±7,000 ng·ml-1, still more preferably 10,000±6,000 ng·ml-1, yet more preferably 10,000±5,000 ng·ml-1, even more preferably 10,000±4,000 ng·ml-1, most preferably 10,000±3,000 ng·ml-1, and in particular 10,000±2,000 ng·ml-1.

Preferably, the pharmaceutical patch has an area of at least 5 cm$^2$, more preferably at least 7.5 cm$^2$, still more preferably at least 10 cm$^2$, and most preferably at least 15 cm$^2$.

In a preferred embodiment, the pharmaceutical patch has an area, i.e. total surface area when being applied to the skin, within the range of 200±150 cm$^2$ (i.e. from 50 cm2 to 350 cm2), more preferably 200±125 cm$^2$, still more preferably 200±100 cm$^2$, yet more preferably 200±75 cm$^2$, even more preferably 150±50 cm$^2$, most preferably 150±25 cm$^2$, and in particular 150±10 cm$^2$. In another preferred embodiment, the pharmaceutical patch has an area within the range of 300±150 cm$^2$, more preferably 300±125 cm$^2$, still more preferably 300±100 cm$^2$, yet more preferably 300±75 cm$^2$, even more preferably 300±50 cm$^2$, most preferably 300±25 cm$^2$, and in particular 300±10 cm$^2$. In still another preferred embodiment, the pharmaceutical patch has an area within the range of 400±150 cm$^2$, more preferably 400±125 cm$^2$, still more preferably 400±100 cm$^2$, yet more preferably 400±75 cm$^2$, even more preferably 400±50 cm$^2$, most preferably 400±25 cm$^2$, and in particular 400±10 cm$^2$.

In a preferred embodiment, the pharmaceutical patch has an area, i.e. total surface area when being applied to the skin, within the range of 25±20 cm$^2$, more preferably 25±15 cm$^2$, still more preferably 25±10 cm$^2$. In another preferred embodiment, the pharmaceutical patch has an area, i.e. total surface area when being applied to the skin, within the range of 50±40 cm$^2$, more preferably 50±35 cm$^2$, still more preferably 50±30 cm$^2$, yet more preferably 50±25 cm$^2$, even more preferably 50±20 cm$^2$, most preferably 50±15 cm$^2$, and in particular 50±10 cm$^2$. In still another preferred embodiment, the pharmaceutical patch has an area within the range of 75±40 cm$^2$, more preferably 75±35 cm$^2$, still more preferably 75±30 cm$^2$, yet more preferably 75±25 cm$^2$, even more preferably 75±20 cm$^2$, most preferably 75±15 cm$^2$, and in particular 75±10 cm$^2$. In yet another preferred embodiment, the pharmaceutical patch has an area within the range of 100±80 cm$^2$, more preferably 100±60 cm$^2$, still more preferably 100±50 cm$^2$, yet more preferably 100±40 cm$^2$, even more preferably 100±30 cm$^2$, most preferably 100±20 cm$^2$, and in particular 100±10 cm$^2$. In a further preferred embodiment, the pharmaceutical patch has an area within the range of 150±80 cm$^2$, more preferably 150±60 cm$^2$, still more preferably 150±50 cm$^2$, yet more preferably 150±40 cm$^2$, even more preferably 150±30 cm$^2$, most preferably 150±20 cm$^2$, and in particular 150±10 cm$^2$. In still a further preferred embodiment, the pharmaceutical patch has an area within the range of 200±80 cm$^2$, more preferably 200±60 cm$^2$, still more preferably 200±50 cm$^2$, yet more preferably 200±40 cm$^2$, even more preferably 200±30 cm$^2$, most preferably 200±20 cm$^2$, and in particular 200±10 cm$^2$. In yet a further preferred embodiment, the pharmaceutical patch has an area within the range of 250±80 cm$^2$, more preferably 250±60 cm$^2$, still more preferably 250±50 cm$^2$, yet more preferably 250±40 cm$^2$, even more preferably 250±30 cm$^2$, most preferably 250±20 cm$^2$, and in particular 250±10 cm$^2$.

Preferably, the pharmaceutical device upon application to the skin provides over a period of at least 6 hours, more preferably at least 12 hours, even more preferably at least 24 hours, release of the pharmacologically active ingredient at a rate in the range of from at least 1.0 to 100,000 μg·cm-2·h-1.

Preferably, the pharmaceutical device has an area, i.e. total surface area when being applied to the skin of at least 5 cm$^2$, more preferably at least 7.5 cm$^2$, still more preferably at least 10 cm$^2$, and most preferably at least 15 cm$^2$.

In another preferred embodiment of the present invention, the pharmaceutical device has an area, i.e. total surface area when being applied to the skin of at most 30 cm$^2$, more preferably at most 25 cm$^2$, still more preferably at most 20 cm$^2$.

In another preferred embodiment of the present invention, the pharmaceutical device has an area, i.e. total surface area when being applied to the skin within the range of from 1 to 30 cm$^2$, more preferably within the range of from 2 to 25 cm$^3$, still more preferably within the range of from 3 to 22 cm$^2$, most preferably within the range of from 5 to 20 cm$^2$.

In a preferred embodiment, the pharmaceutical device has an area, i.e. total surface area when being applied to the skin, within the range of 200±150 cm$^2$ (i.e. from 50 cm2 to 350 cm2), more preferably 200±125 cm$^2$, still more preferably 200±100 cm$^2$, yet more preferably 200±75 cm$^2$, even more preferably 150±50 cm$^2$, most preferably 150±25 cm$^2$, and in particular 150±10 cm$^2$. In another preferred embodiment, the pharmaceutical device has an area within the range of 300±150 cm$^2$, more preferably 300±125 cm$^2$, still more preferably 300±100 cm$^2$, yet more preferably 300±75 cm$^2$, even more preferably 300±50 cm$^2$, most preferably 300±25 cm$^2$, and in particular 300±10 cm$^2$. In still another preferred embodiment, the pharmaceutical device has an area within the range of 400±150 cm$^2$, more preferably 400±125 cm$^2$, still more preferably 400±100 cm$^2$, yet more preferably 400±75 cm$^2$, even more preferably 400±50 cm$^2$, most preferably 400±25 cm$^2$, and in particular 400±10 cm$^2$.

In a preferred embodiment, the pharmaceutical device has an area, i.e. total surface area when being applied to the skin, within the range of 25±20 cm$^2$, more preferably 25±15 cm$^2$, still more preferably 25±10 cm$^2$. In another preferred embodiment, the pharmaceutical device has an area, i.e. total surface area when being applied to the skin, within the range of 50±40 cm$^2$, more preferably 50±35 cm$^2$, still more preferably 50±30 cm$^2$, yet more preferably 50±25 cm$^2$, even more preferably 50±20 cm$^2$, most preferably 50±15 cm$^2$, and in particular 50±10 cm$^2$. In still another preferred embodiment, the pharmaceutical device has an area within the range of 75±40 cm$^2$, more preferably 75±35 cm$^2$, still more preferably 75±30 cm$^2$, yet more preferably 75±25 cm$^2$, even more preferably 75±20 cm$^2$, most preferably 75±15 cm$^2$, and in particular 75±10 cm$^2$. In yet another preferred embodiment, the pharmaceutical device has an area within the range of 100±80 cm$^2$, more preferably 100±60 cm$^2$, still more preferably 100±50 cm$^2$, yet more preferably 100±40 cm$^2$, even more preferably 100±30 cm$^2$, most preferably 100±20 cm$^2$, and in particular 100±10 cm$^2$. In a further preferred embodiment, the pharmaceutical device has an area within the range of 150±80 cm$^2$, more preferably 150±60 cm$^2$, still more preferably 150±50 cm$^2$, yet more preferably 150±40 cm$^2$, even more preferably 150±30 cm$^2$, most preferably 150±20 cm$^2$, and in particular 150±10 cm$^2$. In still a further preferred embodiment, the pharmaceutical device has an area within the range of 200±80 cm$^2$, more preferably 200±60 cm$^2$, still more preferably 200±50 cm$^2$, yet more preferably 200±40 cm$^2$, even more preferably 200±30 cm$^2$, most preferably 200±20 cm$^2$, and in particular 200±10 cm$^2$. In yet a further preferred embodiment, the pharmaceutical device has an area within the range of 250±80 cm², more preferably 250±60 cm², still more preferably 250±50 cm², yet more preferably 250±40 cm², even more preferably 250±30 cm², most preferably 250±20 cm², and in particular 250±10 cm².

The inventive device further comprises means (4) for applying the device to skin (5). Any suitable means for applying the device to the skin may be used such as a strap or a bracelet or an adhesive or any combination thereof. Preferably, the inventive device is applied to the skin by means of an adhesive such as a pressure sensitive adhesive. In particular, the inventive device is applied to the skin by means of an adhesive layer, preferably an adhesive layer (4a) which is part of the inventive device, in particular in case the device is a patch.

The drug reservoir (3) is preferably located within a drug layer (14).

However, alternatively, the drug reservoir (3) may be located at least partly within the adhesive layer (4a), i.e. may be fully integrated in the adhesive layer (4a). Alternatively, it may be partly integrated in the adhesive layer (4a), in particular, in case the drug reservoir (3) is integrated in both the adhesive layer (4a) and a further adhesive layer (8).

Alternatively, the drug reservoir (3) is located between a surface layer (7) and an adhesive layer (4a), preferably as a part of a drug layer (14). In such an embodiment, the adhesive layer (4a) may also comprise at least a portion of Tapentadol or a physiologically acceptable salt thereof, e.g. due to migration and/or diffusion of Tapentadol or a physiologically acceptable salt thereof form the drug reservoir (3) into the adhesive layer (4a).

Preferably, the adhesive layer (4a) comprises a polymer that forms a matrix in which the pharmacologically active ingredient may be dispersed at least partly upon migration to the skin (5) (drug-in-adhesive).

In case the inventive device is an electrophoretic device, of the at least one pair of electrodes consisting of an active electrode and a counter electrode (1a and 2a), the active electrode (1a) is preferably located within adhesive layer (8) or within drug layer (14), and the counter electrode (2a) is preferably located within adhesive layer (4a) or within drug layer (14).

In case the inventive device is an iontophoretic device, of the at least one pair of electrodes consisting of an active electrode and a counter electrode (1b and 2b), the active electrode (1b) is preferably located within adhesive layer (4a) or within drug layer (14), and the counter electrode (2b) is preferably located within adhesive layer (4a) or within drug layer (14). Preferably, the counter electrode (2b) is in contact with or is integrated within an additional reservoir (15).

In case the inventive device is a combined electrophoretic and iontophoretic device, of the at least one pair of electrodes consisting of an active electrode and a counter electrode (1a and 2a and/or 1b and 2b) and the optionally at least one additional electrode as an auxiliary electrode, the active electrode (1a) is preferably located within adhesive layer (8) or within drug layer (14), and the counter electrode (2a) is preferably located within adhesive layer (4a) or within drug layer (14), and the active electrode (1b) is preferably located within adhesive layer (4a) or within drug layer (14), and the counter electrode (2b) is preferably located within adhesive layer (4a) or within drug layer (14). Preferably, the counter electrode (2b) is in contact with or is integrated within an additional reservoir (15).

Preferably, the adhesive layer (4a) comprises a pressure sensitive adhesive selected from the group consisting of silicone-based pressure sensitive adhesives, acrylate-based pressure sensitive adhesives, polyisobutylene-based pressure sensitive adhesives, styrene block copolymer-based pressure sensitive adhesives, ethylene vinyl acetate-based pressure sensitive adhesives, polyurethane-based pressure sensitive adhesives and rubber-based pressure sensitive adhesives. Preferably, in each case said adhesive preferably forms a matrix in which the pharmacologically active ingredient is ingredient is at least partly embedded in form of a drug reservoir (3) (drug-in-adhesive).

In yet another preferred embodiment, the pressure sensitive adhesive contained in the adhesive layer (4a) comprises a mixture of two or more different pressure sensitive adhesives, e.g. a combination of two different acrylate-based pressure sensitive adhesives, or a combination of an acrylate-based pressure sensitive adhesive with a silicone-based pressure sensitive adhesive or a combination of an acrylate-based pressure sensitive adhesive with a styrene block copolymer-based pressure sensitive adhesive or a combination of two different silicone-based pressure sensitive adhesives.

In particular, the adhesive layer (4a) comprises at least one silicone-based pressure sensitive adhesive.

In case at least one silicone-based pressure sensitive adhesive is employed for the production of adhesive layer (4a), especially preferred silicone-based pressure sensitive adhesives are commercially available, e.g. under the trademarks BIO-PSA 7-4301, BIO-PSA 7-4302, BIO-PSA 7-4201, BIO-PSA 7-4202, BIO-PSA 7-4101, BIO-PSA 7-4102, BIO-PSA 7-4601, BIO-PSA 7-4602, BIO-PSA 7-4501, BIO-PSA 7-4502, BIO-PSA 7-4401 and BIO-PSA 7-4402 by Dow Corning Corporation. The silicone-based pressure sensitive adhesive preferably contains a solvent such as ethyl acetate or heptane and has a solids content of approx. 55-65 wt.-% solids before being dried during the preparation of the plaster. The solvents are typically removed during the manufacture of the pharmaceutical device, though residual traces of solvent may be analytically detectable. Especially preferred silicone based adhesives are commercially available by Dow Corning Corporation under the trademarks BIO PSA 7-4501 (solvent:heptane); BIO PSA 7-4502 (solvent:ethyl acetate); and BIO PSA 7-4503 (solvent:toluene). In a preferred embodiment, the pressure sensitive adhesive is a silicone-based pressure sensitive adhesive which is supplied in heptane or ethyl acetate. Preferably, the silicone polymers contained in the silicone-based pressure sensitive adhesives for construction of the adhesive layer (4a) of the inventive device are produced through a condensation reaction of a silanol endblocked polydimethylsiloxane (PDMS) with a silicate resin.

In case at least one styrene block copolymer-based pressure sensitive adhesive is employed for the production of adhesive layer (4a), this preferably contains a solvent such as toluene or n-heptane. These solvents are typically removed during the manufacture of the pharmaceutical device, though residual traces of solvent may be analytically detectable. Examples for styrene block copolymer-based pressure sensitive adhesives include, but are not limited to styrene-butadiene-styrene block copolymers, styrene-ethylene/butylene-styrene block copolymers, styrene-ethylene/propylene block copolymers and styrene-isoprene-styrene block copolymers. Especially preferred styrene block copolymer-based pressure sensitive adhesives are commercially available, e.g. under the trademark DuroTAK®, Duro-Tak® 87-6911 (solvent:toluene, n-heptane), Duro-Tak® 34-4230, Duro-Tak® 9866, Duro-Tak® 4206 and Duro-Tak® 9684.

In case at least one acrylate-based pressure sensitive adhesive is employed for the production of adhesive layer (4a), this preferably contains a solvent such as ethylacetate, n-heptane and n-hexane. These solvents are typically removed during the manufacture of the pharmaceutical patch, though residual traces of solvent may be analytically detectable. Especially preferred acrylate-based pressure sensitive adhesives are commercially available, e.g. under the trademark DuroTAK®, e.g. Duro-Tak® 387-2052 and especially the 87 series, e.g. Duro-Tak® 87-2287; Duro-Tak® 87-4098; Duro-Tak® 87-4287 (solvent:ethylacetate); Duro-Tak® 87-502A (solvent:ethylacetate, n-heptane and n-hexane); Duro-Tak® 87-900A and Duro-Tak® 87-9301. The acrylate-based pressure sensitive adhesive may contain one or more acrylate homopolymers or one or more acrylate copolymers or graft acrylate copolymers or mixtures thereof. For the purpose of specification, "(meth)acryl" shall refer to both, methacryl as well as acryl. In a preferred embodiment, the adhesive layer (4a) comprises an acrylate copolymer comprising monomer units originating from monomers A which are selected from C1-18-alkyl(meth)acrylates and monomers B which are copolymerizable with monomers A. Thus, the acrylate copolymer is derived from at least one monomer of the type of monomers A and at least one monomer of the type of monomers B.

In a preferred embodiment, the acrylate copolymer is derived from two different monomers (bipolymer), three different monomers (terpolymer) or four different monomers (quaterpolymer). Terpolymers are particularly preferred. Preferred monomers A are selected from the group consisting of methyl(meth)acrylate, ethyl(meth)acrylate, propyl(meth)acrylate, butyl(meth)acrylate, pentyl(meth)acrylate, hexyl(meth)acrylate, cyclohexyl(meth)-acrylate, octyl(meth)acrylate, isobornyl(meth)acrylate, and mixtures thereof. 2-Ethylhexyl(meth)acrylate is a preferred representative of an octyl(meth)acrylate. Preferred monomers B are selected from the group consisting of 2-hydroxyethyl(meth)-acrylate, glyceryl mono(meth)acrylate, glycidyl(meth)acrylate, acrylamide, N,N-diethyl-(meth)acrylamide, 2-ethoxyethyl(meth)acrylate, 2-ethoxyethoxyethyl(meth)acrylate, tetra-hydro-furyl(meth)-acrylate, vinyl acetate, N-vinyl pyrrolidone and mixtures thereof. In a preferred embodiment, the acrylate copolymer is derived from a monomer composition comprising monomer units having at least one hydroxyl functional group, preferably selected from 2-hydroxyethyl(meth)-acrylate and glyceryl mono(meth)acrylate. In a particularly preferred embodiment, the acrylate copolymer is derived from a monomer composition comprising vinyl acetate, 2-ethylhexyl acrylate and 2-hydroxyethyl acrylate (terpolymer), optionally also comprising glycidyl methacrylate (quaterpolymer). In a preferred embodiment, the acrylate-based pressure sensitive adhesive comprises a polyacrylate vinylacetate copolymer having at least one hydroxyl functional group. In another preferred embodiment, the acrylate-based pressure sensitive adhesive comprises a graft copolymer, preferably a polyacrylate graft copolymer having at least one hydroxyl functional group, wherein the grafted side chains are preferably hydrocarbon based.

The thickness of the adhesive layer (4a) is not particularly limited and may depend upon a number of factors such as content of Tapentadol or a physiologically acceptable salt thereof and excipients, prescribed duration of application of pharmaceutical device on the skin, and the like.

Preferably, the adhesive layer (4a) has a thickness within the range of from 1.0 to 1000 µm.

In a preferred embodiment, the adhesive layer (4a) has a thickness within the range of from 50±35 µm (i.e. from 15 µm to 85 µm), more preferably 50±30 µm, still more preferably 50±25 µm, yet more preferably 50±20 µm, even more preferably 50±15 µm, most preferably 50±10 µm, and in particular 50±5 µm. In another preferred embodiment, the adhesive layer (4a) has a thickness within the range of from 75±70 µm, more preferably 75±60 µm, still more preferably 75±50 µm, yet more preferably 75±40 µm, even more preferably 75±30 µm, most preferably 75±20 µm, and in particular 75±10 µm. In still another preferred embodiment, the adhesive layer (4a) has a thickness within the range of from 100±70 µm, more preferably 100±60 µm, still more preferably 100±50 µm, yet more preferably 100±40 µm, even more preferably 100±30 µm, most preferably 100±20 µm, and in particular 100±10 µm. In yet another preferred embodiment, the adhesive layer (4a) has a thickness within the range of from 200±175 µm, more preferably 200±150 µm, still more preferably 200±125 µm, yet more preferably 200±100 µm, even more preferably 200±75 µm, most preferably 200±50 µm, and in particular 200±25 µm. In a further preferred embodiment, the adhesive layer (4a) has a thickness within the range of from 300±175 µm, more preferably 300±150 µm, still more preferably 300±125 µm, yet more preferably 300±100 µm, even more preferably 300±75 µm, most preferably 300±50 µm, and in particular 300±25 µm. In still a further preferred embodiment, the adhesive layer (4a) has a thickness within the range of from 400±175 µm, more preferably 400±150 µm, still more preferably 400±125 µm, yet more preferably 400±100 µm, even more preferably 400±75 µm, most preferably 400±50 µm, and in particular 400±25 µm. In yet a further preferred embodiment, the adhesive layer (4a) has a thickness within the range of from 500±175 µm, more preferably 500±150 µm, still more preferably 500±125 µm, yet more preferably 500±100 µm, even more preferably 500±75 µm, most preferably 500±50 µm, and in particular 500±25 µm.

Preferably, the area weight of the adhesive layer (4a) is within the range of from 1 to 150,000 g·m−2, more preferably 10 to 130,000 g·m−2 or 3 to 100,000 g·m−2, still more preferably 20 to 110,000 g·m−2 or 5 to 50,000 g·m−2, yet more preferably 40 to 90,000 g·m−2 or 7 to 10,000 g·m−2, even more preferably 60 to 70,000 g·m−2 or 8 to 1,000 g·m−2, most preferably 80 to 60,000 g·m−2 or 9 to 750 g·m−2, and in particular 100 to 50,000 g·m−2 or 10 to 500 g·m−2.

Preferably, the pharmaceutical device according to the present invention additionally comprises a removable protective layer (release liner). Preferably, the removable protective layer comprises a polymer film and a silicone coating or fluoropolymer coating. Preferably, the polymer film is a polyolefin, in particular polyethylene or polypropylene film or polyester, in particular polyethylene terephthalate film. Preferably, the removable protective layer is coated on only one side. In a preferred embodiment, the removable protective layer is a silicone coated polyester film, such as a silicone coated polyethylene terephthalate film.

In another preferred embodiment, the removable protective layer is a fluoropolymer coated polyester film, such as a fluoropolymer coated polyethylene terephthalate film.

The thickness of the removable protective layer is not particularly limited. Preferably, the removable protective layer has a thickness within the range of from 0.1 to 500 µm. In a preferred embodiment, the removable protective layer has a thickness within the range of from 0.5 to 400 µm, more preferably from 1 to 300 µm, still more preferably from 5 to 250 µm, most preferably from 10 to 200 µm, and in particular from 20 to 150 µm or from 40 to 100 µm.

In a preferred embodiment, the removable protective layer has a thickness within the range of 75±70 µm (i.e. from 5 µm to 145 µm), more preferably 75±60 µm, still more preferably 75±50 µm, yet more preferably 75±40 µm, even more preferably 75±30 µm, most preferably 75±20 µm, and in particular 75±10 µm. In another preferred embodiment, the removable protective layer has a thickness within the range of 100±70 µm, more preferably 100±60 µm, still more preferably 100±50 µm, yet more preferably 100±40 µm, even more preferably 100±30 µm, most preferably 100±20 µm, and in particular 100±10 µm.

Preferably, the adhesive layer (4a) is located between the outer surface, which preferably is formed by a surface layer (7) of the inventive pharmaceutical device and the removable protective layer.

Thus, preferably, the pharmaceutical device according to the present invention additionally comprises a surface layer (7). The surface layer (7) is preferably impermeable to the pharmacologically active ingredient that is contained in the pharmaceutical device. Preferably, the surface layer (7) forms the outer surface of the inventive pharmaceutical device, i.e. when the pharmaceutical device is applied to the skin the surface layer (7) is the visible layer of the pharmaceutical device.

The term "surface layer" as used herein preferably refers to any layer that represents the surface layer after the application of the pharmaceutical device. This definition includes permanent backing layers commonly used for pharmaceutical devices such as patches as well as thin non-removable films that are typically used in thin flexible patches.

In a preferred embodiment, the surface layer (7) comprises one or more polymers selected from the group consisting of polyurethanes, polyester elastomers, polyether block amides, polyacrylates, ethylene vinyl acetates, ethylene acrylate copolymers, ionomer resins, polyvinyl chloride, polyvinylidene chloride, polyesters such as polyterephthalates, and polyolefins, such as polyethylene; polyolefins, in particular polyethylene, polyesters, ethylene vinylacetate copolymers and polyurethanes are particularly preferred.

The surface layer (7) may be a laminate, preferably comprising a polymer film, such as a polyester film, and aluminum foil and/or heat seal layer. In a preferred embodiment, the surface layer consists of a polyester film. Preferably, the surface layer is not coated. The surface layer (7) may contain an optionally present control unit and/or an optionally present electric power source (6a and/or 6b). The thickness of the surface layer (7) is not particularly limited. Preferably, the surface layer has a thickness within the range of from 0.1 to 5,000 µm. In a preferred embodiment, the surface layer has a thickness within the range of from 0.5 to 1,000 µm, more preferably from 1 to 750 µm, still more preferably from 5 to 500 µm, most preferably from 10 to 250 µm, and in particular from 20 to 150 µm or from 40 to 100 µm.

In a preferred embodiment, the surface layer has a thickness within the range of 75±30 µm (i.e. of from 45 µm to 105 µm), more preferably 75±15 µm, still more preferably 75±10 µm, and yet more preferably 75±5 µm.

In one preferred embodiment, one of the two opposing surfaces of the adhesive layer (4a) is in intimate contact with, i.e. adjacent to the removable protective layer. Thus, by removing the removable protective layer from one surface of the adhesive layer (4a), the adhesive layer (4a) is unprotected and the inventive device may be applied to the skin (5) by means of the adhesive layer (4a). Preferably, the other of the two opposing surfaces of the adhesive layer (4a) is in intimate contact with the drug reservoir (3) or, in case the drug reservoir (3) is integrated in a drug layer (14), is in intimate contact with said drug layer (14).

In a preferred embodiment, the other of the two opposing surfaces of the adhesive layer (4a), which is not in intimate contact with, i.e. adjacent to, the removable protective layer is in intimate contact with a drug layer (14), in which the drug reservoir (3), an optionally present electrolyte reservoir, a barrier material (10) and, further, a foam ring (9) is integrated. The inventive device according to this embodiment may further comprise an additional adhesive layer (8) between the drug layer (14) and the surface layer (7). According to this embodiment of the invention, the pharmaceutical device preferably comprises a surface layer (7), an adhesive layer (8), a drug layer (14), an adhesive layer (4a) and optionally a removable protective layer, preferably wherein the drug layer (14) contains the drug reservoir (3) and, thus, contains essentially the total amount of the pharmacologically active ingredient that is contained in the pharmaceutical device. Preferably, the adhesive layer (8) comprises a pressure sensitive adhesive that prevents or at least reduces migration and/or diffusion of Tapentadol and/or a physiologically acceptable salt thereof into the adhesive layer (8), so that said migration and/or diffusion may only occur into the adhesive layer (4a) of the inventive device which is applied to the skin. Preferably, the active electrode (1a) is located within adhesive layer (8) and the counter electrode (2a), the active electrode (1b) and counter electrode (2b) are preferably located within adhesive layer (4a). An insulating material (11) is preferably provided between active electrode (1b) and counter electrode (2b), or, respectively, between counter electrode (2a) and counter electrode (2b).

In another preferred embodiment, the other of the two opposing surfaces of the adhesive layer (4a), which is not in intimate contact with, i.e. adjacent to the removable protective layer, is in intimate contact with the surface layer (7), which in turn preferably forms on its outer surface the outer surface of the pharmaceutical device. In such an embodiment of the inventive device, the drug reservoir (3), an optionally present electrolyte reservoir, a foam material (9) and a barrier material (10), is fully integrated in the adhesive layer (4a). According to this embodiment of the invention, the pharmaceutical device preferably comprises a surface layer (7), an adhesive layer (4a) and a removable protective layer, so that the adhesive layer (4a) contains the drug reservoir (3) and, thus, contains essentially the total amount of the pharmacologically active ingredient that is contained in the pharmaceutical device (drug-in-adhesive) by integration of the drug reservoir (3) into the adhesive layer (4a). In such a preferred embodiment, the adhesive layer (4a) is adjacent to the removable protective layer and/or to the surface layer (7). Preferably, the adhesive layer (4a) is adjacent to the removable protective layer and to the surface layer (7). Preferably, the active electrode (1a), the counter electrode (2a), the active electrode (1b) and counter electrode (2b) are located within adhesive layer (4a). An insulating material (11) is preferably provided between active electrode (1b) and counter electrode (2b), or, respectively, between counter electrode (2a) and counter electrode (2b).

In yet another preferred embodiment, the other of the two opposing surfaces of the adhesive layer (4a), which is not in intimate contact with, i.e. adjacent to the removable protective layer, is not in intimate contact with the surface layer (7), which in turn preferably forms on its outer surface the outer surface of the pharmaceutical device. Thus, in such an embodiment, the inventive device may contain at least one additional layer which is located between the adhesive layer (4a) and the surface layer (7). Preferably, in such an embodiment, the inventive device comprises an additional adhesive layer (8). In such an embodiment of the inventive device, the drug reservoir (3), an optionally present electrolyte reservoir, a foam material (9) and a barrier material (10), is at least partially integrated in the adhesive layer (4a) and at least partially integrated in the adhesive layer (8). According to this embodiment of the invention, the pharmaceutical device preferably comprises a surface layer (7), an adhesive layer (8), an adhesive layer (4a) and a removable protective layer, so that the adhesive layer (4a) and optionally the adhesive layer (8) contain the drug reservoir (3) and, thus, contain essentially the total amount of the pharmacologically active ingredient that is contained in the pharmaceutical device by integration of the drug reservoir (3) into the adhesive layers (4a) and (8). Preferably, the adhesive layer (8) comprises a pressure sensitive adhesive that prevents or at least reduces migration and/or diffusion of Tapentadol or a physiologically acceptable salt thereof into the adhesive layer (8), so that said migration and/or diffusion may only occur into the adhesive layer (4a) of the inventive device which is applied to the skin. Preferably, the active electrode (1a) is located within adhesive layer (8) and the counter electrode (2a), the active electrode (1b) and counter electrode (2b) are preferably located within adhesive layer (4a). An insulating material (11) is preferably provided between active electrode (1b) and counter electrode (2b), or, respectively, between counter electrode (2a) and counter electrode (2b).

Preferably, the adhesive layer (8) comprises a pressure sensitive adhesive that prevents or at least reduces migration and/or diffusion of Tapentadol or a physiologically acceptable salt thereof into the adhesive layer (8).

Preferably, the adhesive layer (8) comprises a pressure sensitive adhesive selected from the group consisting of silicone-based pressure sensitive adhesives, acrylate-based pressure sensitive adhesives, polyisobutylene-based pressure sensitive adhesives, styrene block copolymer-based pressure sensitive adhesives, ethylene vinyl acetate-based pressure sensitive adhesives, polyurethane-based pressure sensitive adhesives and rubber-based pressure sensitive adhesives. Preferably, in each case said adhesive preferably forms a matrix. The identical pressure sensitive adhesives may be employed for the production of an adhesive layer (8), which may be employed for the production of adhesive layer (4a).

In particular, the adhesive layer (8) comprises at least one acrylate-based pressure sensitive adhesive. More preferably, the adhesive layer (8) comprises at least one acrylate-based pressure sensitive adhesive which is selected from the group of acrylate-based pressure sensitive adhesive which may also be used for the manufacture of adhesive layer (4) such as commercially available acrylate-based pressure sensitive adhesives, e.g. under the trademark DuroTAK®, e.g. Duro-Tak® 387-2052 and especially the 87 series, e.g. Duro-Tak® 87-2287; Duro-Tak® 87-4098; Duro-Tak® 87-4287 (solvent:ethylacetate); Duro-Tak® 87-502A (solvent:ethylacetate, n-heptane and n-hexane); Duro-Tak® 87-900A and Duro-Tak® 87-9301.

The adhesive layers (4a) and (8) may comprise identical or different pressure sensitive adhesives. Preferably, the adhesive layer (8) comprises at least one acrylate-based pressure sensitive adhesive and the adhesive layer (4a) comprises at least one silicone-based pressure sensitive adhesive. However, adhesive layer (8) preferably comprises a pressure sensitive adhesive that prevents or at least reduces migration and/or diffusion of Tapentadol or a physiologically acceptable salt thereof into the adhesive layer (8).

The thickness of the adhesive layer (8) is not particularly limited and may depend upon a number of factors such as content of Tapentadol or a physiologically acceptable salt thereof and excipients within the device, prescribed duration of application of pharmaceutical device on the skin, and the like. Preferably, the adhesive layer (8) has a thickness within the range of from 1.0 to 1000 µm.

In a preferred embodiment, the adhesive layer (8) has a thickness within the range of from 50±35 µm (i.e. from 15 µm to 85 µm), more preferably 50±30 µm, still more preferably 50±25 µm, yet more preferably 50±20 µm, even more preferably 50±15 µm, most preferably 50±10 µm, and in particular 50±5 µm. In another preferred embodiment, the adhesive layer (8) has a thickness within the range of from 75±70 µm, more preferably 75±60 µm, still more preferably 75±50 µm, yet more preferably 75±40 µm, even more preferably 75±30 µm, most preferably 75±20 µm, and in particular 75±10 µm. In still another preferred embodiment, the adhesive layer (8) has a thickness within the range of from 100±70 µm, more preferably 100±60 µm, still more preferably 100±50 µm, yet more preferably 100±40 µm, even more preferably 100±30 µm, most preferably 100±20 µm, and in particular 100±10 µm. In yet another preferred embodiment, the adhesive layer (8) has a thickness within the range of from 200±175 µm, more preferably 200±150 µm, still more preferably 200±125 µm, yet more preferably 200±100 µm, even more preferably 200±75 µm, most preferably 200±50 µm, and in particular 200±25 µm. In a further preferred embodiment, the adhesive layer (8) has a thickness within the range of from 300±175 µm, more preferably 300±150 µm, still more preferably 300±125 µm, yet more preferably 300±100 µm, even more preferably 300±75 µm, most preferably 300±50 µm, and in particular 300±25 µm. In still a further preferred embodiment, the adhesive layer (8) has a thickness within the range of from 400±175 µm, more preferably 400±150 µm, still more preferably 400±125 µm, yet more preferably 400±100 µm, even more preferably 400±75 µm, most preferably 400±50 µm, and in particular 400±25 µm. In yet a further preferred embodiment, the adhesive layer (8) has a thickness within the range of from 500±175 µm, more preferably 500±150 µm, still more preferably 500±125 µm, yet more preferably 500±100 µm, even more preferably 500±75 µm, most preferably 500±50 µm, and in particular 500±25 µm.

Preferably, the area weight of the adhesive layer (8) is within the range of from 1 to 150,000 g·m−2, more preferably 10 to 130,000 g·m−2 or 3 to 100,000 g·m−2, still more preferably 20 to 110,000 g·m−2 or 5 to 50,000 g·m−2, yet more preferably 40 to 90,000 g·m−2 or 7 to 10,000 g·m−2, even more preferably 60 to 70,000 g·m−2 or 8 to 1,000 g·m−2, most preferably 80 to 60,000 g·m−2 or 9 to 750 g·m−2, and in particular 100 to 50,000 g·m−2 or 10 to 500 g·m−2.

The total thickness of the pharmaceutical device is not particularly limited. Preferably, the total thickness of the pharmaceutical device is within the range of from 20 to 5000 µm, more preferably 40 to 4500 µm, still more preferably 60 to 4000 µm, yet more preferably 80 to 3500 µm, most preferably 100 to 3000 µm, and in particular 150 to 2500 µm. In a preferred embodiment, the total thickness of the pharmaceutical device is within the range of 100±75 µm (i.e. from 25 µm to 175 µm), preferably 100±50 µm. In another preferred embodiment, the total thickness of the pharmaceutical device is within the range of 150±100 µm, preferably 150±75 µm, more preferably 150±50 µm. In still another preferred embodiment, the total thickness of the pharmaceutical device is within the range of 200±150 µm, preferably 200±100 µm, more preferably 200±50 µm. In yet another preferred embodiment, the total thickness of the pharmaceutical device is within the range of 300±250 µm, preferably 300±200 µm, more preferably 300±150 µm, still more preferably 300±100 µm, and yet more preferably 300±50 µm. In a further preferred embodiment, the total thickness of the pharmaceutical device is within the range of 400±350 µm, preferably 400±300 µm, more preferably 400±250 µm, still more preferably 400±200 µm, yet more preferably 400±150 µm, even more preferably 400±100 µm, and most preferably 400±50 µm. In still a further preferred embodiment, the total thickness of the pharmaceutical device is within the range of 500±400 µm, preferably 500±350 µm, more preferably 500±300 µm, still more preferably 500±250 µm, yet more preferably 500±200 µm, even more preferably 500±150 µm, most preferably 500±100 µm, and in particular 500±50 µm. In still a further preferred embodiment, the total thickness of the pharmaceutical device is within the range of 1000±400 µm, preferably 1000±350 µm, more preferably 1000±300 µm, still more preferably 1000±250 µm, yet more preferably 1000±200 µm, even more preferably 1000±150 µm, most preferably 1000±100 µm, and in particular 1000±50 µm. In still a further preferred embodiment, the total thickness of the pharmaceutical device is within the range of 1500±400 µm, preferably 1500±350 µm, more preferably 1500±300 µm, still more preferably 1500±250 µm, yet more preferably 1500±200 µm, even more preferably 1500±150 µm, most preferably 1500±100 µm, and in particular 1500±50 µm. In still a further preferred embodiment, the total thickness of the pharmaceutical device is within the range of 2000±400 µm, preferably 2000±350 µm, more preferably 2000±300 µm, still more preferably 2000±250 µm, yet more preferably 2000±200 µm, even more preferably 2000±150 µm, most preferably 2000±100 µm, and in particular 2000±50 µm. In preferred embodiments, the aforementioned values include the removable protective layer. In another preferred embodiment, the aforementioned values exclude the removable protective layer.

The pharmaceutical device according to the invention may be prepared by standard techniques for the manufacture of pharmaceutical devices. Such standard techniques are known to the skilled person (cf., e.g., H. A. E. Benson et al., Topical and Transdermal Drug Delivery: Principles and Practice, John Wiley & Sons; 2011; A. K. Banga, Transdermal and Intradermal Delivery of Therapeutic Agents: Application of Physical Technologies, CRC Press Inc; 2011). Further, the preparation of electrophoretic, iontophoretic or combined electrophoretic and iontophoretic devices is e.g. known from DE 10 2010 024 558 A1, U.S. Pat. No. 5,830,175, US 2010/0247617 A1, US 2009/0062720 A1, U.S. Pat. No. 5,533,995 and US 2010/189793 A1.

For example, an inventive device may be prepared in that a foam layer is provided through which an inner opening, for example in the form of a ring opening, is punched out to form a foam ring (9). In said opening a drug reservoir (3) containing Tapentadol or a physiologically acceptable salt thereof, and further, a barrier material (10) is inserted to form a drug layer (14) together with the foam ring (9). The drug reservoir (3) can be prepared separately by methods known to a person skilled in the art such as in K. H. Bauer et al., Lehrbuch der Pharmazeutischen Technologie, 2006. An active electrode (1a) is provided on the first side of the opening and a counter electrode (2a) is provided on the other second side of the opening in case the inventive device is an electrophoretic device. An active electrode (1b) and a counter electrode (2b) are provided on the second side of the opening in case the inventive device is an iontophoretic device, which are separated from each other through a suitable insulating material (11) as isolator. An active electrode (1a) is provided on the first side of the opening and a counter electrode (2a) as well as an auxiliary electrode are provided on the other side of the opening, wherein the auxiliary electrode may function as a counter electrode (2b) in such a way that the counter electrode (2a) of the pair of electrodes (1a and 2a) is used as an active electrode (1b) in case the inventive device is a combined electrophoretic and iontophoretic device, and wherein active electrode (1b) and counter electrode (2b) are separated from each other through a suitable insulating material (11) as isolator. A pressure-sensitive adhesive layer (4a) is applied to second opening. A pressure-sensitive adhesive layer (8) is applied to the first opening. A surface layer (7) is applied to the adhesive layer (8) and a removable release layer is applied to adhesive layer (4a). The removable release layer has to be removed before applying the inventive device to the skin.

A control unit as well as an electric power supply (6a and/or 6b) are electronically printed on the surface layer (7) or have been printed on the adhesive layer (8) prior to coating of adhesive layer (8) with surface layer (7). The electrodes may be incorporated into any of the adhesive layers (4a) or (8), i.e. active electrode (1a) can be incorporated into adhesive layer (8) and the counter electrode (2a), active electrode (1b) and counter electrode (2b) is preferably located within adhesive layer (4a).

The pharmaceutical device according to the invention is preferably suitable for use in the treatment of pain, preferably moderate to severe acute and chronic pain.

The pharmaceutical device according to the invention is preferably suitable for use in the treatment of chronic joint pain (osteoarthritis of the hip or knee), low back pain, chronic cancer pain, chronic painful diabetic peripheral neuropathy (DPN), acute dental pain, acute pain after bunionectomy, acute pain after abdominal surgery, acute pain after hip replacement, acute pain after abdominal hysterectomy (visceral pain) and acute pain in patients waiting for joint replacement.

The treatment of pain can either be effected in a systemic therapy or a local therapy. In case of highly localized pain (e.g. bruises or joint pain) a local treatment, i.e. placing the pharmaceutical device directly on the hurting body part, may be favored providing rapid relief at lower doses of the pharmacologically active ingredient compared to a systemic approach.

In a preferred embodiment, the pharmaceutical device according to the invention is suitable for use in a systemic treatment of pain.

In another preferred embodiment, the pharmaceutical device according to the invention is suitable for use in a local treatment of pain. Preferably, the pain is moderate, severe, or moderate to severe. In a preferred embodiment, the pain to be treated is neuropathic pain, preferably chronic neuropathic pain such as painful diabetic neuropathy.

For the purpose of specification, neuropathic pain is pain that originates from nerve damage or nerve malfunction. Preferably, the neuropathic pain is selected from acute neuropathic pain and chronic neuropathic pain. Neuropathic pain may be caused by damage or disease affecting the central or peripheral portions of the nervous system involved in bodily feelings (the somatosensory system). Preferably, the pharmaceutical patch according to the invention is for use in the treatment of chronic neuropathic pain or acute neuropathic pain, peripheral neuropathic pain or central neuropathic pain, mononeuropathic pain or polyneuropathic pain. When the neuropathic pain is chronic, it may be chronic peripheral neuropathic pain or chronic central neuropathic pain, in a preferred embodiment chronic peripheral mononeuropathic pain or chronic central mononeuropathic pain, in another preferred embodiment chronic peripheral polyneuropathic pain or chronic central polyneuropathic pain. When the neuropathic pain is acute, it may be acute peripheral neuropathic pain or acute central neuropathic pain, in a preferred embodiment acute peripheral mononeuropathic pain or acute central mononeuropathic pain, in another preferred embodiment acute peripheral polyneuropathic pain or acute central polyneuro-pathic pain. The invention also relates to the pharmacologically active ingredient according to the invention a physiologically acceptable salt thereof for use in the treatment of neuropathic pain as described above.

Central neuropathic pain is found in spinal cord injury, multiple sclerosis, and some strokes. Fibromyalgia is potentially a central pain disorder and is responsive to medications that are effective for neuropathic pain. Accordingly, the pharmaceutical device according to the invention is also suitable for the treatment of fibromyalgia. Aside from diabetic neuropathy and other metabolic conditions, the common causes of painful peripheral neuropathies are herpes zoster infection, HIV-related neuropathies, nutritional deficiencies, toxins, remote manifestations of malignancies, genetic, and immune mediated disorders or physical trauma to a nerve trunk. Neuropathic pain is common in cancer as a direct result of cancer on peripheral nerves (e.g., compression by a tumor), or as a side effect of chemotherapy, radiation injury or surgery.

The pharmaceutical device according to the invention is also suitable for use in the treatment of nociceptive pain, preferably acute or chronic nociceptive pain. Preferably, the pain is moderate, severe, or moderate to severe.

Nociceptive pain refers to the discomfort that results when a stimulus causes tissue damage to the muscles, bones, skin or internal organs. For the purpose of specification, nociceptive pain is caused by stimulation of peripheral nerve fibers that respond only to stimuli approaching or exceeding harmful intensity (nociceptors), and may be classified according to the mode of noxious stimulation; the most common categories being "thermal" (heat or cold), "mechanical" (crushing, tearing, etc.) and "chemical" (iodine in a cut, chili powder in the eyes). Nociceptive pain may also be divided into "visceral," "deep somatic" and "superficial somatic" pain.

Visceral pain describes a type of nociceptive pain originating in the body's internal organs or their surrounding tissues. This form of pain usually results from the infiltration of harmful cells, as well as the compression or extension of healthy cells. Patients suffering from visceral pain tend to feel generally achy, as this pain tends to not be localized to a specific area. Cancer is a common source of visceral pain.

Somatic pain is nociceptive pain that results from some injury to the body. It's generally localized to the affected area and abates when the body repairs the damage to that area. Deep somatic pain is initiated by stimulation of nociceptors in ligaments, tendons, bones, blood vessels, fasciae and muscles, and is dull, aching, poorly-localized pain. Examples include sprains and broken bones. Superficial pain is initiated by activation of nociceptors in the skin or superficial tissues, and is sharp, well-defined and clearly located.

According to the invention, nociceptive pain is preferably classified chronic if it has occurred for at least 3 months. Preferably, the chronic nociceptive pain is selected from chronic visceral pain, chronic deep somatic pain and chronic superficial somatic pain.

Preferred causes of nociceptive pain according to the invention include broken or fractured bones, bruises, burns, cuts, inflammation (from infection or arthritis), and sprains. Thus, nociceptive pain includes post-operative pain, cancer pain, low back pain, and inflammatory pain.

In preferred embodiments, the pain to be treated is selected from the group consisting of pain being or being associated with panic disorder [episodic paroxysmal anxiety] [F41.0]; dissociative [conversion] disorders [F44]; persistent somatoform pain disorder [F45.4]; pain disorders exclusively related to psychological factors [F45.41]; non-organic dyspareunia [F52.6]; other enduring personality changes [F62.8]; sadomasochism [F65.5]; elaboration of physical symptoms for psychological reasons [F68.0]; migraine [G43]; other headache syndromes [G44]; trigeminal neuralgia [G50.0]; atypical facial pain [G50.1]; phantom limb syndrome with pain [G54.6]; phantom limb syndrome without pain [G54.7]; acute and chronic pain, not elsewhere classified [G89]; ocular pain [H57.1]; otalgia [H92.0]; angina pectoris, unspecified [120.9]; other specified disorders of nose and nasal sinuses [J34.8]; other diseases of pharynx [J39.2]; temporomandibular joint disorders [K07.6]; other specified disorders of teeth and supporting structures [K08.8]; other specified diseases of jaws [K10.8]; other and unspecified lesions of oral mucosa [K13.7]; glossodynia [K14.6]; other specified diseases of anus and rectum [K62.8]; pain in joint [M25.5]; shoulder pain [M25.51]; sacrococcygeal disorders, not elsewhere classified [M53.3]; spine pain [M54.]; radiculopathy [M54.1]; cervicalgia [M54.2]; sciatica [M54.3]; low back pain [M54.5]; pain in thoracic spine [M54.6]; other dorsalgia [M54.8]; dorsalgia, unspecified [M54.9]; other shoulder lesions [M75.8]; other soft tissue disorders, not elsewhere classified [M79]; myalgia [M79.1]; neuralgia and neuritis, unspecified [M79.2]; pain in limb [M79.6]; other specified disorders of bone [M89.8]; unspecified renal colic [N23]; other specified disorders of penis [N48.8]; other specified disorders of male genital organs [N50.8]; mastodynia [N64.4]; pain and other conditions associated with female genital organs and menstrual cycle [N94]; mittelschmerz [N94.0]; other specified conditions associated with female genital organs and menstrual cycle [N94.8]; pain in throat and chest [R07]; pain in throat [R07.0]; chest pain on breathing [R07.1]; precordial pain [R07.2]; other chest pain [R07.3]; chest pain, unspecified [R07.4]; abdominal and pelvic pain [R10]; acute abdomen pain [R10.0]; pain localized to upper abdomen [R10.1]; pelvic and perineal pain [R10.2]; pain localized to other parts of lower abdomen [R10.3]; other and unspecified abdominal pain [R10.4]; flatulence and related conditions [R14]; abdominal rigidity [R19.3]; other and unspecified disturbances of skin sensation [R20.8]; pain associated with micturition [R30]; other and unspecified symptoms and signs involving the urinary system [R39.8]; headache [R51]; pain, not elsewhere classified [R52]; acute pain [R52.0]; chronic intractable pain [R52.1]; other chronic pain [R52.2]; pain, unspecified [R52.9]; other complications of cardiac and vascular prosthetic devices, implants and grafts [T82.8]; other complications of genitourinary prosthetic devices, implants and grafts [T83.8]; other complications of internal orthopaedic prosthetic devices, implants and grafts [T84.8]; other complications of internal prosthetic devices, implants and grafts, not elsewhere classified [T85.8]; wherein the information in brackets refers to the classification according to ICD-10.

In another preferred embodiment, the pharmaceutical device is designed for application to the skin for a period of least 1 day, more preferably at least 2 days, most preferably at least 3 days or at least 3.5 days, and in particular 3 days, 3.5 days, 4 days or 7 days. Thus, according to this embodiment, continuous administration of the pharmacologically active ingredient can be achieved by removing a used pharmaceutical device after said period has expired and replacing it by a fresh pharmaceutical device.

The locations of the skin to which the pharmaceutical device according to the invention is to be applied are not particularly limited. Preferably, the pharmaceutical device according to the invention is applied to the skin of the breast or the skin of the back or the skin of the arms or the skin of the legs.

In a preferred embodiment, the pharmaceutical devices according to the invention are repeatedly applied to the same location on the skin, i.e. after a first pharmaceutical device has been used and needs to be replaced by a second pharmaceutical device in order to maintain the desired pharmacological effect, said second pharmaceutical device is preferably applied to the same location on the skin to which said first pharmaceutical device was applied before.

In another preferred embodiment, particularly when the patient has a sensitive skin, the pharmaceutical devices according to the invention are applied to the different locations on the skin, i.e. after a first pharmaceutical device has been used and needs to be replaced by a second pharmaceutical device in order to maintain the desired pharmacological effect, said second pharmaceutical device is preferably applied to a location on the skin differing from the location on the skin to which said first pharmaceutical device was applied before.

The pharmaceutical device according to the invention is for administration to the skin of a mammal, preferably of a human (pediatrics or adults).

Another aspect of the present invention is Tapentadol and/or a physiologically acceptable salt thereof for use in the treatment of pain, wherein the Tapentadol and/or the physiologically acceptable salt thereof is administered by means of the pharmaceutical device according to the present invention.

In a preferred embodiment of the present invention Tapentadol and/or a physiologically acceptable salt thereof for use in the treatment of pain, is administered by means of the pharmaceutical device according to the present invention, wherein an electrical potential difference ($V_a$ and/or $V_b$) is applied to the at least one pair of electrodes consisting of an active electrode and a counter electrode (1a and 2a and/or 1b and 2b), and/or the optionally present at least one additional electrode, preferably an electrical potential difference ($V_a$ and/or $V_b$) which is within the range of from 0.5 to 12.5 V, preferably within the range of from 0.5 to 11.5 V, more preferably within the range of from 0.5 to 11.0 V, even more preferably within the range of from 0.5 to 10.5 V, still more preferably within the range of from 0.5 to 10.0 V.

In another preferred embodiment of the present invention Tapentadol and/or a physiologically acceptable salt thereof for use in the treatment of pain, is administered by means of the pharmaceutical device according to the present invention, wherein an electrical potential difference ($V_a$ and/or $V_b$) is applied to the at least one pair of electrodes consisting of an active electrode and a counter electrode (1a and 2a and/or 1b and 2b), and/or the optionally present at least one additional electrode, which is within the range of from 0.50 to 7.50 V, more preferably within the range of from 0.75 to 7.25 V, even more preferably within the range of from 1.00 to 7.00 V, still more preferably within the range of from 1.25 to 6.75 V, even still more preferably within the range of from 1.50 to 6.50 V, yet more preferably within the range of from 1.75 to 6.25 V, in particular within the range of from 2.00 to 6.00 V, most preferred within the range of from 2.50 to 6.50 V. In another preferred embodiment of the present invention, said electrical potential difference ($V_a$ and/or $V_b$) is within the range of from 2.75 to 6.25 V, more preferably within the range of from 3.00 to 6.00 V, even more preferably within the range of from 3.25 to 5.75 V, still more preferably within the range of from 3.50 to 5.50 V. In yet another preferred embodiment of the present invention, said electrical potential difference ($V_a$ and/or $V_b$) is within the range of from 0.50±0.25 to 7.50±0.25 V, more preferably within the range of from 0.75±0.25 to 7.25±0.25 V, even more preferably within the range of from 1.00±0.25 to 7.00±0.25 V, still more preferably within the range of from 1.25±0.25 to 6.75±0.25 V, even still more preferably within the range of from 1.50±0.25 to 6.50±0.25 V, yet more preferably within the range of from 1.75±0.25 to 6.25±0.25 V, in particular within the range of from 2.00±0.25 to 6.00±0.25 V, most preferred within the range of from 2.50±0.25 to 6.50±0.25 V. In yet another preferred embodiment of the present invention said electrical potential difference ($V_a$ and/or $V_b$) is within the range of from 2.75±0.25 to 6.25±0.25 V, more preferably within the range of from 3.00±0.25 to 6.00±0.25 V, even more preferably within the range of from 3.25±0.25 to 5.75±0.25 V, still more preferably within the range of from 3.50±0.25 to 5.50±0.25 V. In yet another preferred embodiment of the present invention said electrical potential difference ($V_a$ and/or $V_b$) is at least 0.50±0.25 V, more preferably at least 0.75±0.25 V, even more preferably at least 1.00±0.25 V, still more preferably at least 1.25±0.25 V, even still more preferably at least 1.50±0.25 V, yet even more preferably at least 1.75±0.25 V, in particular at least 2.00±0.25 V, most preferred at least 2.50±0.50 V.

In a further preferred embodiment of the present invention Tapentadol and/or a physiologically acceptable salt thereof for use in the treatment of pain, is administered by means of the pharmaceutical device according to the present invention, wherein an electrical potential difference ($V_a$ and/or $V_b$) is repeatedly applied to the at least one pair of electrodes consisting of an active electrode and a counter electrode (1a and 2a and/or 1b and 2b), and/or the optionally present at least one additional electrode as an auxiliary electrode in predetermined repetition intervals in each case independently of one another for a predetermined period of time within the total period of time, during which the device is applied to the skin (5).

In yet a further preferred embodiment of the present invention Tapentadol and/or a physiologically acceptable salt thereof for use in the treatment of pain, is administered by means of the pharmaceutical device according to the present invention, wherein the total period of time during which an electrical potential difference ($V_a$ and/or $V_b$) is applied to the pair of electrodes (1a and 2a and/or 1b and 2b) and optionally to the additional auxiliary electrode is at most 20%, preferably at most 18%, more preferably at most 16%, even more preferably at most 14%, still more preferably at most 12%, even more preferably at most 10% of the total period of time during which the device is applied to the skin (5). In another preferred embodiment of the present invention, said total time period is at most 9%, preferably at most 8%, more preferably at most 7%, even more preferably at most 6%, still more preferably at most 5%, even further more preferably at most 4% of the total period of time during which the device is applied to the skin (5). In another preferred embodiment of the present invention, said total time period is at most 12±2%, preferably at most 11±2%, more preferably at most 10±2%, even more preferably at most 9±2%, still more preferably at most 8±2%, even still more preferably at most 7±2%, yet more preferably at most 6±2%, in particular at most 5±2% of the total period of time during which the device is applied to the skin (5).

In yet another further preferred embodiment of the present invention Tapentadol and/or a physiologically acceptable salt thereof for use in the treatment of pain, is administered by means of the pharmaceutical device according to the present invention, wherein the total period of time during which an electrical potential difference (Va and/or Vb) is applied to the pair of electrodes (1a and 2a and/or 1b and 2b) and optionally to the additional auxiliary electrode is at most 75%, preferably at most 65%, more preferably at most 55%, even more preferably at most 45%, still more preferably at most 35%, even more preferably at most 25% of the total period of time during which the device is applied to the skin (5). In another preferred embodiment of the present invention, said total time period is at most 60%, preferably at most 50%, more preferably at most 40%, even more preferably at most 30%, still more preferably at most 20%, even further more preferably at most 10% of the total period of time during which the device is applied to the skin (5). In another preferred embodiment of the present invention, said total time period is at most 50±5%, preferably at most 40±5%, more preferably at most 30±5%, even more preferably at most 20±5%, still more preferably at most 10±5%, even still more preferably at most 8±2%, yet more preferably at most 6±2%, in particular at most 4±2% of the total period of time during which the device is applied to the skin (5).

In yet a further preferred embodiment of the present invention Tapentadol and/or a physiologically acceptable salt thereof for use in the treatment of pain, is administered by means of the pharmaceutical device according to the present invention, wherein the total period of time during which an electrical potential difference (Va and/or Vb) is applied to the pair of electrodes (1a and 2a and/or 1b and 2b) and/or optionally to the additional auxiliary electrode is at most 4.0 hours, preferably at most 3.5 hours, more preferably at most 3.0 hours, even preferably at most 2.5 hours, yet more preferably at most 2.0 hours, further more preferably at most 1.5 hours, in particular at most 1.0 hours, most preferred at most 0.5 hours. In another preferred embodiment of the present invention, said total time period is at most 4.0±0.5 hours, preferably at most 3.5±0.5 hours, more preferably at most 3.0±0.5 hours, even preferably at most 2.5±0.5 hours, yet more preferably at most 2.0±0.5 hours, further more preferably at most 1.5±0.5 hours, in particular at most 1.0±0.5 hours, most preferred at most 0.5±0.25 hours.

In yet a further preferred embodiment of the present invention Tapentadol and/or a physiologically acceptable salt thereof for use in the treatment of pain, is administered by means of the pharmaceutical device according to the present invention, wherein the total period of time, during which the inventive device is applied to the skin (5) is at least 1 hour, preferably at least 2 hours, more preferably at least 3 hours, even more preferably at least 4 hours, yet more preferably at least 5 hours, further more preferably at least 6 hours, in particular at least 7 hours, most preferred at least 8 hours. In another preferred embodiment of the present invention the total period of time, during which the inventive device is applied to the skin (5), is within the range of from 1 hour to 72 h, preferably within the range of from 3 hours to 66 hours, more preferably within the range of from 6 hours to 60 hours, even more preferably within the range of from 9 hours to 54 hours, still more preferably within the range of from 12 hours to 48 hours, yet more preferably within the range of from 15 hours to 42 hours, in particular within the range of from 18 hours to 36 hours, most preferred within the range of from 21 hours to 30 hours.

Preferred exemplary embodiments of the present invention are depicted in FIG. 1 to FIG. 3:

FIG. 1 is a schematic view of a pharmaceutical device according to the present invention, wherein one pair of electrodes consisting of an active electrode (1a) and a counter electrode (2a) create an electrical field (Fa) by applying an electrical potential difference (Va) by use of an electric power source (6a) and are arranged such that the electric field (Fa) is substantially perpendicular to the skin (5) in order to induce electrophoretic movement of the Tapentadol and/or of the physiologically acceptable salt thereof within the device from the drug reservoir (3) towards the skin (5), when the device is applied thereto. The device is applied to the skin (5) by means of an adhesive layer (4a), in which the counter electrode (2a) is integrated. The device further comprises a surface layer (7) which is connected to the inventive device via a second adhesive layer (8), in which the active electrode (1a) is integrated. The device further comprises a foam ring (9) in which the drug reservoir (3) including a barrier material (10) is integrated to form a drug layer (14).

FIG. 2 is a schematic view of a pharmaceutical device according to the present invention, wherein one pair of electrodes consisting of an active electrode (1b) and a counter electrode (2b) create an electrical field (Fb) by applying an electrical potential difference (Vb) by use of an electric power source (6b) and are arranged such that the electric field (Fb) is substantially parallel to the skin (5) in order to induce iontophoretic movement of the Tapentadol and/or of the physiologically acceptable salt thereof out of the device from the drug reservoir (3) into the skin (5), when the device is applied thereto. The device is applied to the skin (5) by means of an adhesive layer (4a). The device further comprises a surface layer (7) which is connected to the inventive device via a second adhesive layer (8), in which the active electrode (1b) and the counter electrode (2b) is integrated The device further comprises a foam ring (9) in which the drug reservoir (3) including a barrier material (10) is integrated to form a drug layer (14). Further, an insulating material (11) is provided within the inventive device in order to avoid the occurrence of any short circuits.

FIG. 3 is a schematic view of a pharmaceutical device according to the present invention with one first pair of electrodes consisting of an active electrode and a counter electrode (1a and 2a), which are provided to create an electric field (Fa) by applying an electrical potential difference (Va), and are arranged such that the electric field (Fa) is substantially perpendicular to the skin (5) when the device is applied thereto, and one additional electrode as an auxiliary electrode, which functions as a counter electrode (2b) in such a way that the counter electrode (2a) of the first pair of electrodes (1a and 2a) is used as an active electrode (1b) for creating an electric field (Fb) by applying an electrical potential difference (Vb), these two electrodes forming a second pair of electrodes consisting of an active electrode and a counter electrode (1b and 2b) and are arranged such that the electric field (Fb) is substantially parallel to the skin (5) when the device is applied thereto. Said schematic view also shows a pharmaceutical device according to the present invention with one first pair of electrodes consisting of an active electrode and a counter electrode (1b and 2b), which are provided to create an electric field (Fb) by applying an electrical potential difference (Vb), and are arranged such that the electric field (Fb) is substantially parallel to the skin (5) when the device is applied thereto, and one additional electrode as an auxiliary electrode, which functions as an active electrode (1a) for creating an electric field (Fa) by applying an electrical potential difference (Va) using the active electrode (1b) of the first pair of electrodes (1b and 2b) as a counter electrode (2a), these two electrodes forming a second pair of electrodes consisting of an active electrode and a counter electrode (1a and 2a) and are arranged such that the electric field (Fa) is substantially perpendicular to the skin (5) when the device is applied thereto. The device is applied to the skin (5) by means of an adhesive layer (4a), in which the counter electrode (2a), the active electrode (1b) and the counter electrode (2b) is integrated. The device further comprises a surface layer (7) which is connected to the inventive device via a second adhesive layer (8), in which the active electrode (1a) is integrated. The device further comprises a foam ring (9) in which the drug reservoir (3) including a barrier material (10) is integrated to form a drug layer (14). Further, an insulating material (11) is provided within the inventive device in order to avoid the occurrence of any short circuits.

EXAMPLES

The following examples further illustrate the invention but are not to be construed as limiting its scope.

Examples 1A, 1B and Comparative Example 1B

The rate of iontophoretic transdermal delivery of Tapentadol hydrochloride (Tapentadol HCl) has been investigated in examples 1a and 1b. Further, the passive transdermal delivery of Tapentadol HCl without any means of electric-field-assistance has been investigated in comparative example 1b.

Example 1a

Determination of the rate of iontophoretic transdermal delivery of Tapentadol hydrochloride for a period of 8 hours of iontophoresis

Example 1b

Determination of the rate of iontophoretic transdermal delivery of Tapentadol hydrochloride for a period of 24 hours of iontophoresis

Comparative Example 1b

For comparison, the rate of transdermal delivery of Tapentadol hydrochloride for a period of 24 hours has been determined without any means of electric-field-assisted administration (passive control).

Method employed in examples 1a and 1b:
Tapentadol hydrochloride (batch no. A0012) was employed. The components of the phosphate buffered saline (PBS) and the mobile phase used were from Sigma, UK. The pig skin was obtained from a local farm, washed with water, excess hair was carefully trimmed with scissors, and the skin was dermatomed using a Zimmer dermatome set at a nominal thickness of 750 μm. The skin was then stored at −20° C.

The drug was delivered from the anode, using side-bi-side (horizontal) glass diffusion cells (n=6) supplied by Permegear, USA. The porcine skin membrane was excised from the dorsal surface.

Electrodes were prepared in-house and were made of silver/silver chloride. To pass current for 24 hours in this set-up, it was necessary for the donor compartment to contain 76 mM chloride ions.

The anode was placed in the donor chamber; the donor solution was 3 ml of Tapentadol hydrochloride (100 mM, i.e. 25.78 mg/ml of Tapentadol hydrochloride, 22.13 mg/ml of base) in water. The cathode was placed in the receptor chamber, which contained 3 ml of phosphate-buffered saline, pH 7.4. Both chambers were stirred by magnets.

The applied constant current, electrode areas and current density are given in the table below. Current was applied for a total of 8 or 24 hours, respectively.

| | |
|---|---|
| Area (cm2) | 0.64 |
| Current (mA) | 0.25 |
| Density (mA/cm2) | 0.4 |

The receptor solution was sampled and assayed at 0.5, 1, 2, 3, 4, 5, 6, 7, 8 (example 1a) and optionally 24 hours (example 1b) post-initiation of the current. During the 8 hour experiment (example 1a), at 0.5, 1, 2, and 3 hours, 1 ml of receptor solution was removed and replaced with fresh PBS. As it was clear that the amount of Tapentadol in the receptor solution was sufficient for quantitation by HPLC, at the subsequent sampling times of 4, 5, 6, 7 and 8 hours, the entire receptor solution (3 ml) was removed and replaced with fresh PBS, to ensure sink conditions in the receptor. During the 24 hour experiment (example 1b), the entire receptor solution (3 ml) was removed and replaced with fresh PBS at every sampling point.

The concentrations of Tapentadol hydrochloride in the receptor chamber samples were determined by HPLC. A mobile phase consisting of 300:700:1 methanol:water:phosphoric acid was pumped (1 ml/min) through a Acclaim RP-18 (4×150 mm) reverse-phase column (Dionex, UK) at 35° C. Tapentadol concentrations were quantified via their UV absorbance at 215 nm using a calibration curve diluted in PBS at pH 7.4. Injection volume was 20 μl and the retention time for Tapentadol hydrochloride was 12 minutes and the total run time was 16 minutes.

A Tapentadol-free "blank" diffusion cell (donor was saline only) was also prepared and the receptor solution was analysed after 8 hours to confirm no peaks from any component of the skin co-eluted with the Tapentadol hydrochloride.

Voltages were as expected for 6 cells in series (range was 6 to 28 volts). The pH of the donor solution was measured after termination of 24 hours of iontophoresis, and ranged from 6.47 to 6.99. The pH of drug in the donor prior to commencing the experiment was 5.07 (5.34 for the 8 hour iontophoresis).

Method Employed in Comparative Example 1b (Passive Control)

The flux of Tapentadol hydrochloride from passive diffusion alone was measured (n=2). The experimental set-up was exactly as previously described, except that no electrodes were placed in the diffusion cell and no current was applied. The temperature was held at 37° C. The receptor solution was sampled and assayed at 0.5, 1, 1.5, 2, 3, 4, 5, 6, 7, 8 and 24 hours. 1 ml of receptor solution was removed and replaced with fresh PBS at each sampling point.

Results of Example 1a

TABLE 1a-1 cumulative, iontophoretic delivery (in µg) of Tapentadol hydrochloride across the skin (patch area: 0.64 cm$^2$).

| Hours | Cell 1 | Cell 2 | Cell 3 | Cell 4 | Cell 5 | Cell 6 | Mean ± SD | As tapentadol base Mean ± SD |
|---|---|---|---|---|---|---|---|---|
| 0.5 | 3 | 10 | 8 | 1 | 1 | 2 | 4 ± 4 | 3 ± 3 |
| 1 | 27 | 54 | 55 | 16 | 15 | 25 | 32 ± 18 | 28 ± 15 |
| 2 | 131 | 216 | 173 | 128 | 105 | 127 | 147 ± 40 | 126 ± 35 |
| 3 | 321 | 417 | 396 | 312 | 244 | 347 | 340 ± 62 | 291 ± 54 |
| 4 | 550 | 674 | 624 | 522 | 494 | 543 | 568 ± 68 | 487 ± 58 |
| 5 | 792 | 979 | 859 | 759 | 734 | 760 | 814 ± 92 | 699 ± 79 |
| 6 | 1040 | 1253 | 1104 | 984 | 976 | 988 | 1057 ± 107 | 908 ± 92 |
| 7 | 1304 | 1548 | 1375 | 1244 | 1237 | 1203 | 1319 ± 128 | 1132 ± 110 |
| 8 | 1564 | 1901 | 1616 | 1479 | 1479 | 1435 | 1579 ± 171 | 1356 ± 147 |

TABLE 1a-2 drug flux (given in µg/h) of Tapentadol hydrochloride across the skin (patch area: 0.64 cm$^2$).

| Hours | Cell 1 | Cell 2 | Cell 3 | Cell 4 | Cell 5 | Cell 6 | Mean ± SD | As tapentadol base Mean ± SD |
|---|---|---|---|---|---|---|---|---|
| 0.5 | 6 | 19 | 16 | 2 | 1 | 4 | 8 ± 8 | 7 ± 6 |
| 1 | 48 | 89 | 93 | 30 | 29 | 47 | 56 ± 28 | 48 ± 24 |
| 2 | 104 | 162 | 119 | 112 | 90 | 102 | 115 ± 25 | 98 ± 21 |
| 3 | 190 | 201 | 222 | 184 | 139 | 220 | 193 ± 31 | 166 ± 26 |
| 4 | 229 | 257 | 229 | 209 | 250 | 196 | 228 ± 23 | 196 ± 20 |
| 5 | 242 | 305 | 234 | 238 | 240 | 217 | 246 ± 30 | 211 ± 26 |
| 6 | 247 | 275 | 245 | 225 | 242 | 228 | 244 ± 18 | 209 ± 15 |
| 7 | 264 | 295 | 271 | 260 | 261 | 215 | 261 ± 26 | 224 ± 22 |
| 8 | 260 | 353 | 241 | 234 | 242 | 232 | 260 ± 46 | 224 ± 40 |

Results of Example 1b

TABLE 1b-1 cumulative, iontophoretic delivery (in µg) of Tapentadol HCl across the skin (patch area: 0.64 cm$^2$).

| Hours | Cell 1 | Cell 2 | Cell 3 | Cell 4 | Cell 5 | Cell 6 | Mean ± SD | As tapentadol base Mean ± SD |
|---|---|---|---|---|---|---|---|---|
| 0.5 | 1 | 1 | 2 | 4 | 1 | 1 | 2 ± 1 | 1 ± 1 |
| 1 | 16 | 15 | 29 | 47 | 19 | 28 | 26 ± 12 | 22 ± 10 |
| 1.5 | 47 | 60 | 80 | 112 | 64 | 79 | 74 ± 22 | 63 ± 19 |
| 2 | 96 | 113 | 162 | 212 | 134 | 158 | 146 ± 41 | 125 ± 35 |
| 3 | 224 | 259 | 364 | 419 | 315 | 348 | 322 ± 72 | 276 ± 61 |
| 4 | 408 | 476 | 602 | 676 | 563 | 596 | 554 ± 96 | 475 ± 83 |
| 5 | 635 | 747 | 885 | 962 | 847 | 867 | 824 ± 116 | 707 ± 99 |
| 6 | 878 | 1029 | 1183 | 1239 | 1133 | 1142 | 1101 ± 129 | 945 ± 111 |
| 7 | 1125 | 1322 | 1465 | 1534 | 1425 | 1424 | 1382 ± 144 | 1187 ± 123 |
| 8 | 1380 | 1653 | 1721 | 1836 | 1727 | 1706 | 1671 ± 155 | 1434 ± 133 |
| 24 | 6185 | 7120 | 7001 | 7000 | 6247 | 6145 | 6616 ± 468 | 5680 ± 402 |

TABLE 1b-2 drug flux (given in µg/h) of Tapentadol hydrochloride across the skin (patch area: 0.64 cm$^2$).

| Hours | Cell 1 | Cell 2 | Cell 3 | Cell 4 | Cell 5 | Cell 6 | Mean ± SD | As tapentadol base Mean ± SD |
|---|---|---|---|---|---|---|---|---|
| 0.5 | 3 | 2 | 4 | 7 | 1 | 3 | 3 ± 2 | 3 ± 2 |
| 1 | 29 | 28 | 54 | 86 | 38 | 53 | 48 ± 22 | 41 ± 19 |
| 1.5 | 62 | 91 | 101 | 130 | 90 | 101 | 96 ± 22 | 82 ± 19 |
| 2 | 99 | 104 | 164 | 200 | 140 | 159 | 144 ± 38 | 124 ± 33 |
| 3 | 128 | 147 | 203 | 208 | 181 | 190 | 176 ± 32 | 151 ± 28 |
| 4 | 184 | 217 | 238 | 257 | 248 | 248 | 232 ± 27 | 199 ± 23 |
| 5 | 227 | 271 | 283 | 285 | 284 | 272 | 270 ± 22 | 232 ± 19 |
| 6 | 243 | 282 | 298 | 277 | 286 | 274 | 277 ± 18 | 238 ± 16 |
| 7 | 248 | 292 | 282 | 295 | 292 | 282 | 282 ± 18 | 242 ± 15 |
| 8 | 254 | 331 | 256 | 302 | 302 | 282 | 288 ± 30 | 247 ± 26 |
| 24 | 300 | 342 | 330 | 323 | 282 | 277 | 309 ± 26 | 265 ± 23 |

Results of Comparative Example 1b (Passive Control)

TABLE C1b-1 cumulative, passive delivery (in µg) of Tapentadol HCl across the skin (patch area: 0.64 cm$^2$).

| Hours | Cell 1 | Cell 2 | Mean | As tapentadol base Mean |
|---|---|---|---|---|
| 0.5 | 0 | 0 | 0 | 0 |
| 1 | 0 | 0 | 0 | 0 |
| 1.5 | 0 | 0 | 0 | 0 |
| 2 | 0 | 0 | 0 | 0 |
| 3 | 2 | 1 | 2 | 1 |
| 4 | 4 | 3 | 4 | 3 |
| 5 | 7 | 5 | 6 | 5 |
| 6 | 11 | 8 | 9 | 8 |
| 7 | 14 | 11 | 13 | 11 |
| 8 | 20 | 15 | 18 | 15 |
| 24 | 192 | 179 | 186 | 159 |

TABLE C1b-2 drug flux (given in µg/h) of Tapentadol hydrochloride across the skin (patch area: 0.64 cm$^2$).

| Hours | Cell 1 | Cell 2 | Mean | As tapentadol base Mean |
|---|---|---|---|---|
| 0.5 | 0 | 0 | 0 | 0 |
| 1 | 0 | 0 | 0 | 0 |
| 1.5 | 0 | 0 | 0 | 0 |
| 2 | 0 | 0 | 0 | 0 |
| 3 | 1 | 1 | 1 | 1 |
| 4 | 2 | 2 | 2 | 2 |
| 5 | 3 | 2 | 3 | 2 |
| 6 | 4 | 3 | 3 | 3 |
| 7 | 4 | 3 | 3 | 3 |
| 8 | 5 | 4 | 5 | 4 |
| 24 | 11 | 10 | 11 | 9 |

Figure 8A:
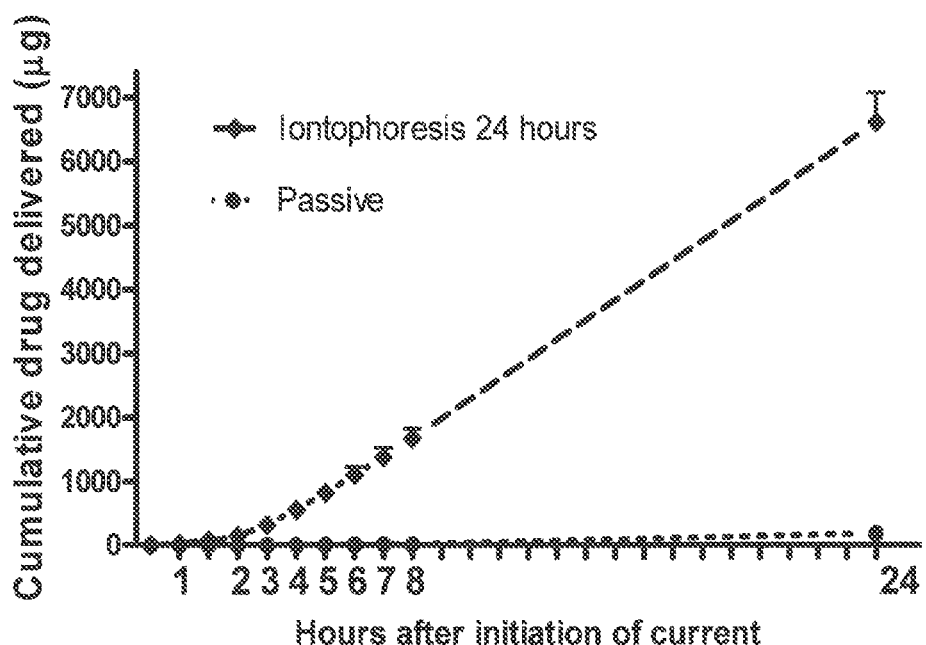
FIGS. 8A and 8B provide a graphical representation of the results of the cumulative, iontophoretic delivery (in $\mu g$) of Tapentadol hydrochloride across the skin according to examples 1a and 1b as well as of the results of the passive control experiment (comparative example 1b).
Figure 8B:
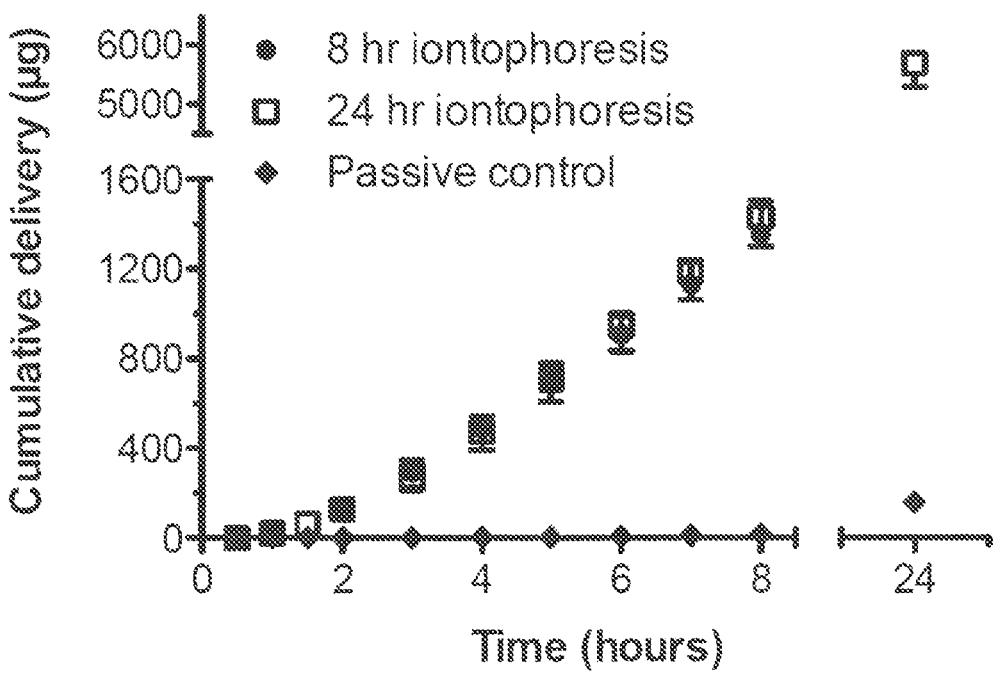

FIGS. 8A and 8B provide a graphical representation of the results of the cumulative, iontophoretic delivery (in µg) of Tapentadol hydrochloride across the skin according to examples 1a and 1b as well as of the results of the passive control experiment (comparative example 1b).

Figure 9A:
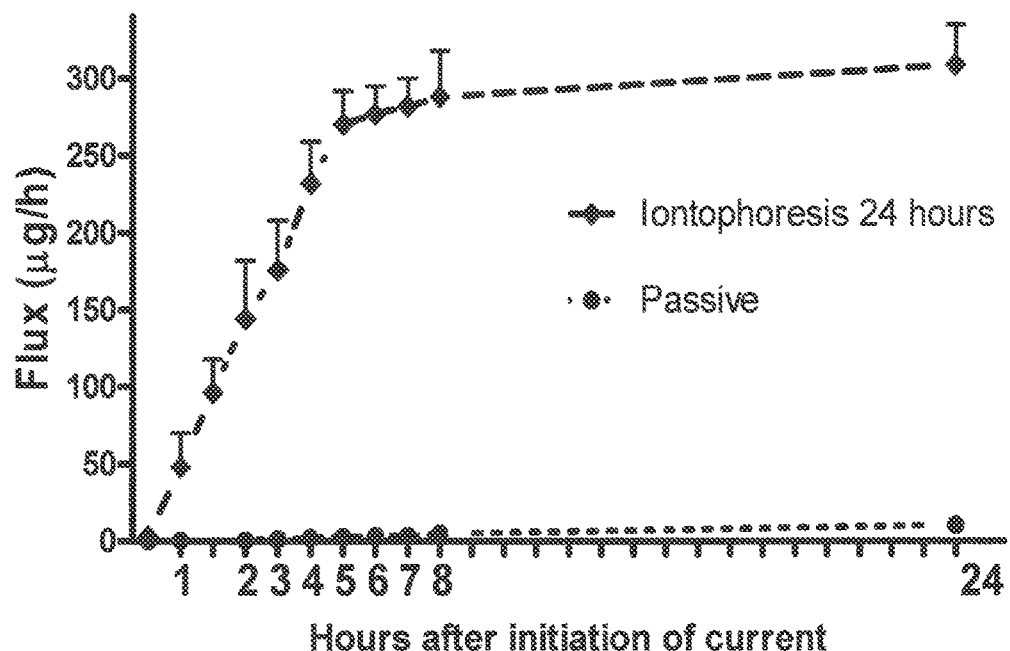
FIGS. 9A and 9B provide a graphical representation of the results of the drug flux (given in $\mu g/h$) of iontophoretic delivery of Tapentadol hydrochloride across the skin according to examples 1a and 1b as well as of the results of the passive control experiment (comparative example 1b).
Figure 9B:
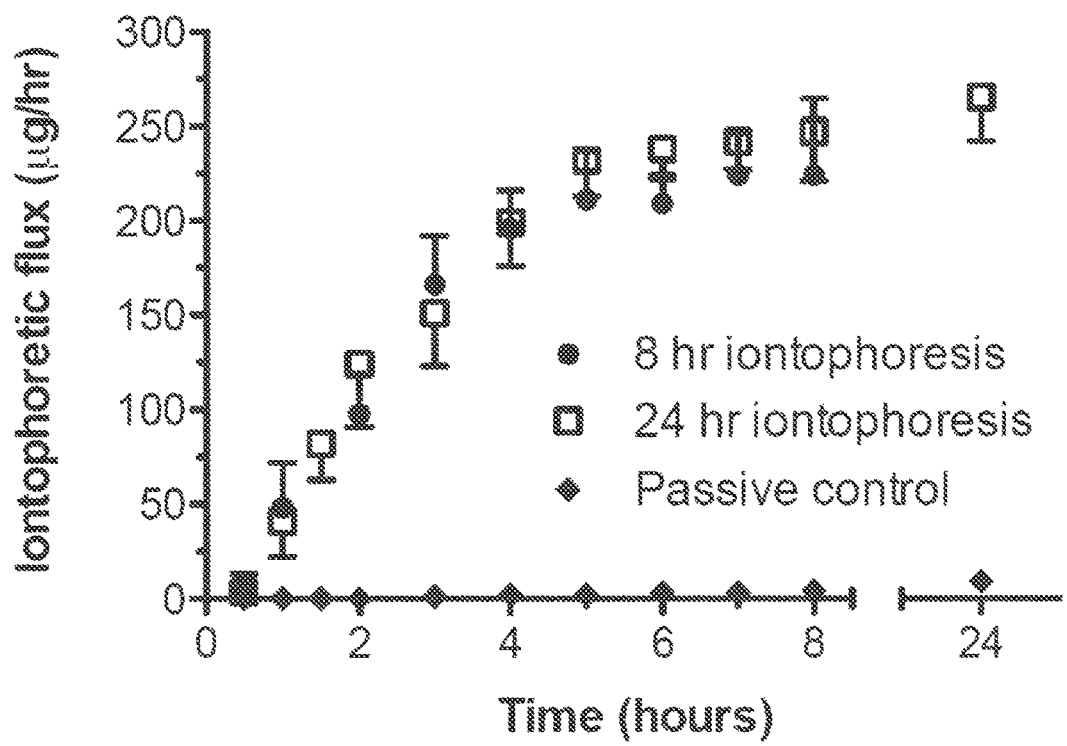

FIGS. 9A and 9B provide a graphical representation of the results of the drug flux (given in µg/h) of Tapentadol hydrochloride across the skin according to examples 1a and 1b as well as of the results of the passive control experiment (comparative example 1b). Discussion of results:

Steady-state flux appears to have been reached by 5-6 hours in each case of example 1a and 1b.

Steady state flux was not reached within 8 hours in case of comparative example 1b. It is not possible to ascertain whether it was reached within 24 hours.

The flux due to passive diffusion (comparative example 1b) alone is markedly lower than the flux observed during iontophoresis (30 fold difference).

The rate of passive diffusion had reached 16 µg/h/cm2 by 24 hours. It follows that an unfeasibly large patch area would be required to deliver daily doses of this drug by passive diffusion alone, i.e. a patch area of 390 cm².

Substantial drug delivery was achieved with iontophoresis. Passive delivery alone results in a comparatively low flux. The cumulative data indicate that 6.6 mg of tapentadol hydrochloride (5.7 mg of tapentadol base) could be delivered across a 0.64 cm2 area of skin in 24 hours, i.e. 10.3 mg of tapentadol hydrochloride (8.9 mg of tapentadol base) per 1 cm2.

Examples 2A, 2B, 2C and Comparative Example 2A

The rate of electrophoretic transdermal delivery of three different exemplary Tapentadol hydrochloride containing hydrogel formulations A, B and C has been investigated in example 2a, 2b and 2c. Further, the rate of passive transdermal delivery of a corresponding Tapentadol hydrochloride containing hydrogel formulation has been investigated in a comparative experiment 2a.

The amounts of Tapentadol delivered have been measured by HPLC (HPLC column: Merck Select B, 125×3.0 m; column temperature 40° C., flow rate 0.65 mL/min, eluent: methanol (32%) and 20 mM phosphate buffer and 1 mL/L triethylamine (68%), retention time of Tapentadol 4.2 min; UV detection, 215 nm wavelength). The linearity of the method was verified by calibration with an aqueous solution of Tapentadol hydrochloride.

Three different hydrogel formulations A-C containing Tapentadol hydrochloride having the following compositions have been prepared:

| Components | Formulation A | Formulation B | Formulation C |
|---|---|---|---|
| Tapentadol [%-wt.], with respect to the free base | 1.4 | 1.59 | 5.22 |
| NaCl [%-wt.] | 0.1 | 0.1 | 0.1 |
| Klucel ® HF [%-wt.] | — | 4.6 | 2.5 |
| Lutrol ® F127 [%-wt.] | 16.2 | — | — |
| Water [%-wt.] | 82.3 | 93.71 | 92.18 |

%-wt. = percent by weight

Klucel® HF is a commercially available product (Ashland, Inc.) based on hydroxypropyl cellulose. Lutrol® F127 is a commercially available copolymer (BASF) of polypropylene glycol and polyethylene glycol.

Formulations A and B each have a pH value of 3, whereas formulation C has a pH value of 7.28.

Example 2a and Comparative Example 2a

The hydrogel formulation B has been placed in an electrophoretic transdermal delivery system according to FIG. 1. The following components were used for preparing the electrophoretic device according to FIG. 1:

silver electrodes as pair of electrodes consisting of an active electrode (1a) and a counter electrode (2a) (silver gauze, 1024 mesh/cm², 0.12 wire diameter, 99.9% Ag, 18 mm diameter), a foam ring (9) (Alveolit TA 1001 005 White, 95 kg/m³, 22 mm outer diameter, 16 mm inner diameter), hydrogel formulation B as drug reservoir (3), a teflon ring as barrier material (10) (thickness 1 mm, outer diameter 16 mm, inner diameter 11 mm), silicone adhesive Bio PSA-7 4502 as adhesive layer (4a), which has been in contact with a removable protective layer prior to use (transparent PETP foil manufactured by 3M®, 74 µm, with one-side fluorination, 22 mm diameter), acrylate adhesive DuroTAK 387-2054 as a second adhesive layer (8), a PET foil as surface layer (7) (Loparex PET foil, 75 µm, 105 g/m², 22 mm diameter).

Two wires were soldered to the electrodes and connected to a conventional current source as electric power source (6a) (Voltakraft® laboratory power supply DIGI 35).

Transdermal delivery experiments across mouse skin have been performed after two short current pulses (2 V) have been applied for 2 s after 1.5 hour and for 2 s after 16.5 hours. This experiment has been performed twice (B-1 and B-2 as example 2a) as indicated in FIG. 4 and FIG. 5.

For comparison, the hydrogel formulation B or A has been placed in an electrophoretic transdermal delivery system according to FIG. 1 and passive transdermal delivery experiments to mouse skin have been performed, i.e. no electric current has been applied to these systems (passive control experiments). This experiment has been performed twice for formulation B (compB-1 and compB-2) and once in case of formulation A (compA) (comparative example 2a) as indicated in FIG. 4 and FIG. 5.

Figure 4:
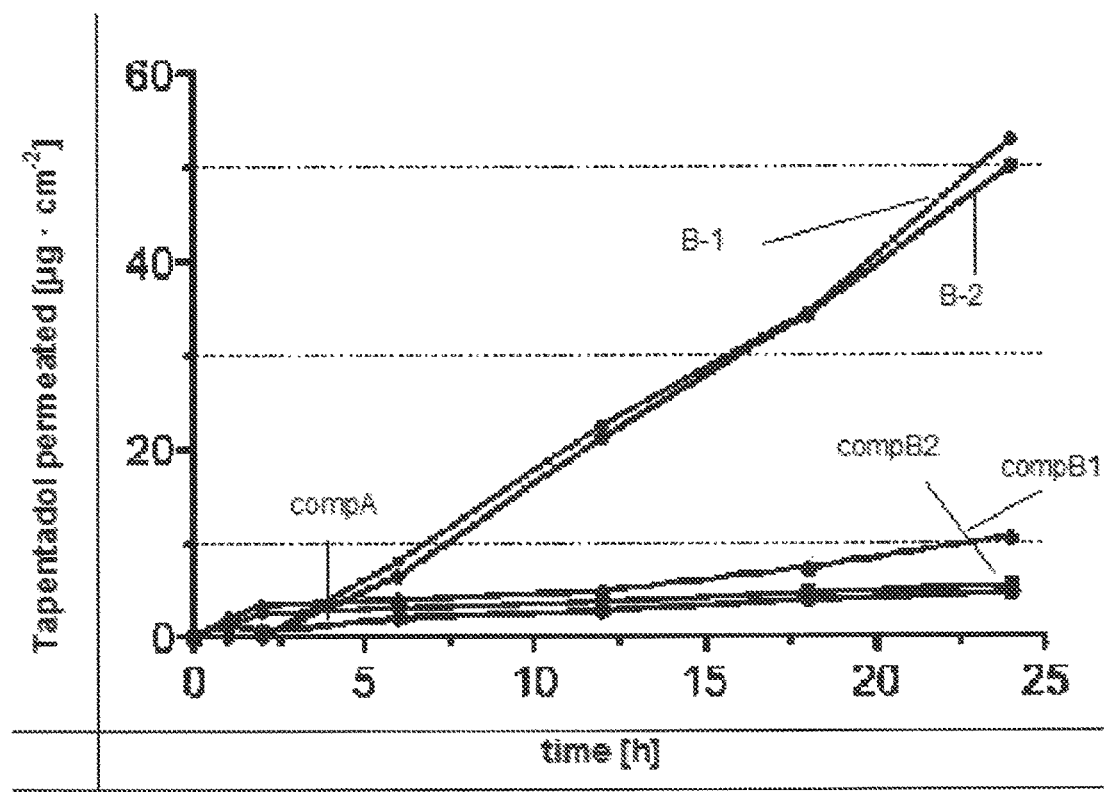
FIG. 4 provides a graphical representation of the results of the cumulative, electrophoretic delivery (in $\mu g/cm^2$) of Tapentadol across the skin according to example 2a as well as of the results of the passive control experiment (comparative example 2a).

FIG. 4 provides a graphical representation of the results of the cumulative, electrophoretic delivery (in µg/cm²) of Tapentadol across the skin according to example 2a as well as of the results of the passive control experiment (comparative example 2a).

Figure 5:
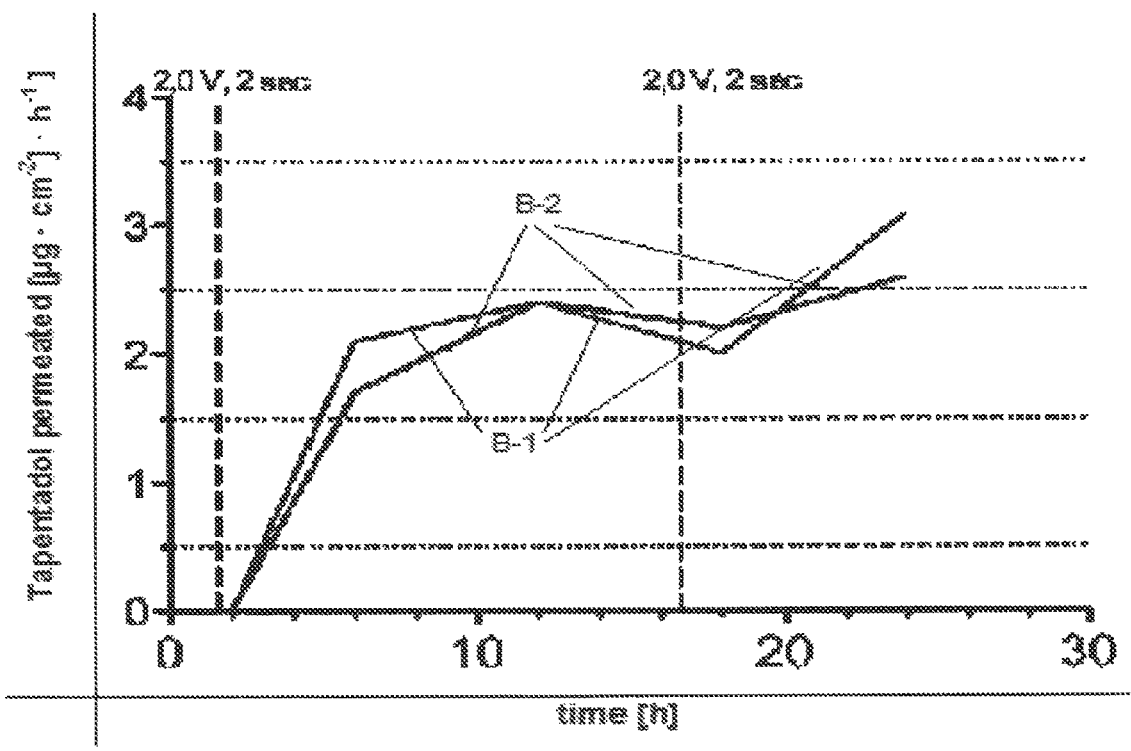

FIG. 5 provides a graphical representation of the results of the drug flux (given in µg/cm² per h) of Tapentadol across the skin according to example 2a.

As can be derived from FIG. 4, the permeated amount due to passive delivery (comparative example 2a) alone is markedly lower than the permeated amount during electrophoresis (example 2a, 5-10 fold difference), i.e. an increase of cumulative skin permeation by the factor of 5-10 can be achieved by electrophoresis.

As can be derived from FIG. 5, the increased flux observed in case of example 2a as displayed in FIG. 4 is due to the application of the electric current since the increase in flux unambiguously correlates with the time of applying the current, i.e. the chronological order of the single pulses, even though a delay time can be observed.

Thus, substantial drug delivery was achieved with electrophoresis. Passive delivery alone results in a comparatively low flux.

Examples 2b (Variation of Duration of Pulse Lengths)

The hydrogel formulation B has been placed in an electrophoretic transdermal delivery system according to FIG. 1 comprising the same components as used for example 2a and comparative example 2a.

Transdermal delivery experiments across mouse skin have been performed after two current pulses have been applied. However, in contrast to example 2a, the duration of the pulse lengths have been varied: a constant voltage of 2 V has been applied in each case for the period of 15 s after 1.5 hours and for the same period after 16.5 hours (B-3), for the period of 30 s after 1.5 hours and for the same period after 16.5 hours (B-4), and for the period of 60 s after 1.5 hours and for the same period after 16.5 hours (B-5) (example 2b) as indicated in FIG. 6.

Figure 6:
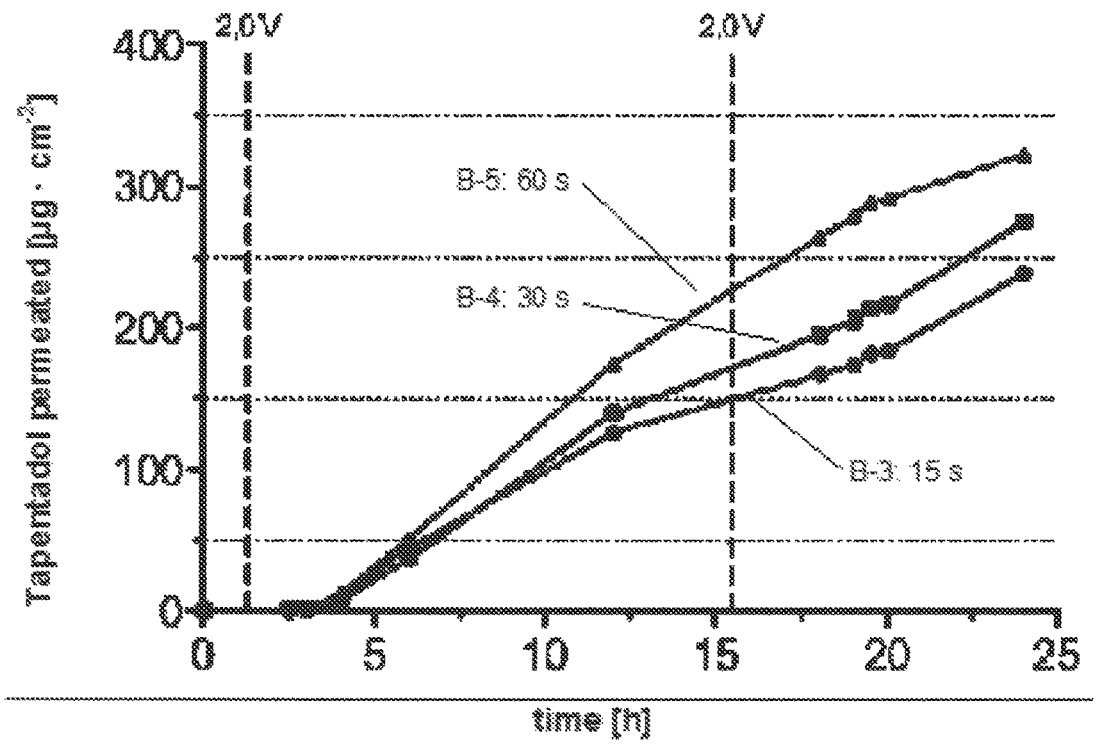
FIG. 6 provides a graphical representation of the results of the cumulative, electrophoretic delivery (in $\mu g/cm^2$) of Tapentadol across the skin according to example 2b (B-3, B-4 and B-5) at varying pulse lengths between 15 and 60 seconds and a constant voltage of 2 V applied during these pulse lengths.

FIG. 6 provides a graphical representation of the results of the cumulative, electrophoretic delivery (in $\mu g/cm^2$) of Tapentadol across the skin according to example 2b (B-3, B-4 and B-5) at varying duration of pulse lengths between 15 and 60 seconds and a constant voltage of 2 V applied during these pulse lengths.

As can be derived from FIG. 6, the cumulative data indicate that the total amount of Tapentadol permeated can be increased by increase of the application time, i.e. can be increased up to more than 300 $\mu g/cm^2$ after 24 hours by electrophoretic delivery (B-5 in FIG. 6). A longer pulse length (60 s) leads to a more sustained release profile than a shorter pulse length (15 s).

Example 2c (Variation of Voltage)

The hydrogel formulation C has been placed in an electrophoretic transdermal delivery system according to FIG. 1 comprising the same components as used for example 2a and comparative example 2a. However, hydrogel formulation C instead of B has been employed. By employing formulation C instead of formulation B, the drug load of Tapentadol hydrochloride has been additionally increased, and, further the pH value has been increased.

Transdermal delivery experiments across mouse skin have been performed. However, in contrast to example 2b, the voltage applied has been varied, while the pulse lengths have been held constant. Thus, a pulse length for the period of 60 s after 1.5 hours and for the same period after 16.5 hours has been used and a voltage of
3 V has been applied during the period of these pulse lengths (C-1),
4 V has been applied during the period of these pulse lengths (C-2), and
5 V has been applied during the period of these pulse lengths (C-3),
in each case (example 2c) as indicated in FIG. 7.

Figure 7:
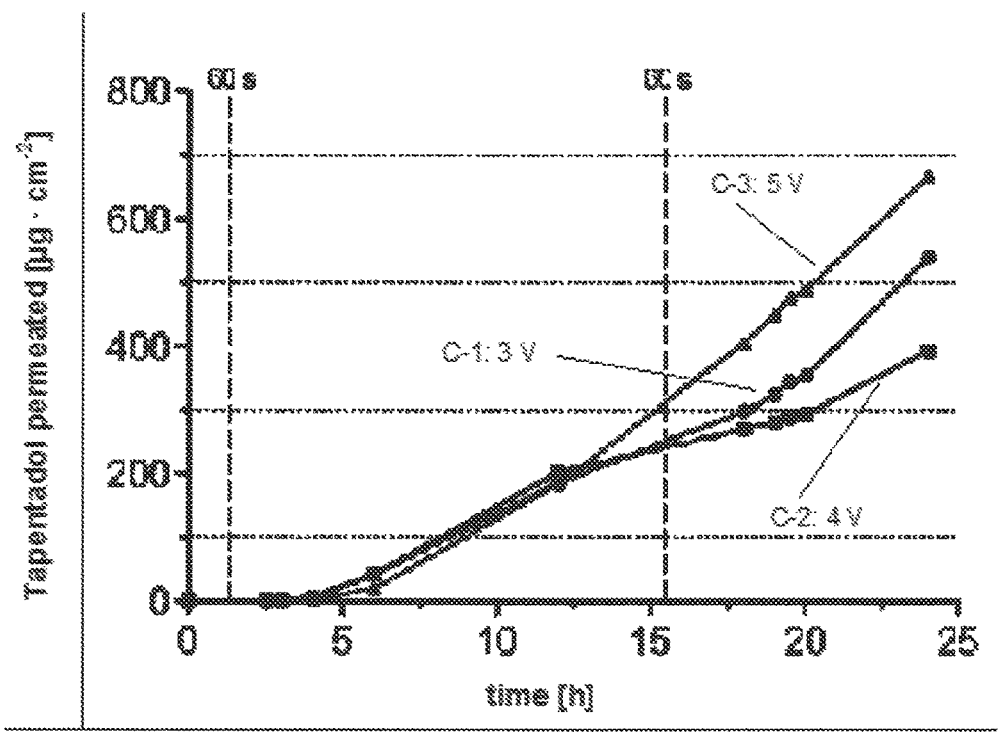
FIG. 7 provides a graphical representation of the results of the cumulative, electrophoretic delivery (in $\mu g/cm^2$) of Tapentadol across the skin according to example 2c (C-1, C-2 and C-3) at varying voltages between 3 and 5 V applied and at constant pulse lengths of 60 s after 1.5 and 16.5 hours in each case.

FIG. 7 provides a graphical representation of the results of the cumulative, electrophoretic delivery (in $\mu g/cm^2$) of Tapentadol across the skin according to example 2c (C-1, C-2 and C-3) at varying voltages applied and at constant pulse lengths of 60 s after 1.5 hours and 16.5 hours in each case.

As can be derived from FIG. 7, the cumulative data indicate that the total amount of Tapentadol permeated can be increased by increase of the voltage applied, i.e. can be increased up to 670 $\mu g/cm^2$ after 24 hours by electrophoretic delivery (C-3 in FIG. 7).

Examples 2a, 2b and 2c show that substantial drug delivery was achieved with electrophoresis, in which in particular the voltage applied and the duration of the pulse lengths, in which said voltage is applied, are important parameters. Since electrophoretic delivery of Tapentadol across the skin is not a passive permeation process, the amount of drug load of Tapentadol or a physiologically acceptable salt thereof within the drug reservoir such as a hydrogel is not a crucial parameter. Over the investigated period of 24 hours of administration about 90 wt.-% of Tapentadol remains within the transdermal delivery system according to examples 2a, 2b and 2c.

A hydrogel formulation C containing Tapentadol or a physiologically acceptable salt thereof within an electrophoretic transdermal delivery system according to FIG. 1 or within a combined a electrophoretic and iontophoretic transdermal delivery system according to FIG. 3 is of particular advantage since such a formulation has a pH of 7.2, i.e. exhibits not—in contrast to formulations A and B—acidic properties, and thus, such a transdermal delivery system may avoid any skin irritations caused by low pH values of the drug containing hydrogel formulations of these systems or pharmaceutical devices comprising these systems.

Examples 3A, 3B and 3C

The rate of combined iontophoretic and electrophoretic transdermal delivery of aTapentadol hydrochloride containing hydrogel formulation has been investigated in examples 3a, 3b and 3c.

The amounts of Tapentadol delivered have been measured by HPLC (HPLC column: Merck Select B, 125×3.0 m; column temperature 40° C., flow rate 0.65 mL/min, eluent: methanol (32%) and 20 mM phosphate buffer and 1 mL/L triethylamine (68%), retention time of Tapentadol 4.2 min; UV detection, 215 nm wavelength). The linearity of the method was verified by calibration with an aqueous solution of Tapentadol hydrochloride.

Example 3a

The hydrogel formulation C (as described in example 2a) has been placed in a combined electrophoretic and iontophoretic device according to FIG. 3. The following components were used for preparing the inventive electrophoretic and iontophoretic device according to FIG. 3:
silver electrodes as pair of electrodes consisting of an active electrode (1a) and a counter electrode (2a) (silver gauze, 1024 mesh/cm$^2$, 0.12 wire diameter, 99.9% Ag, 18 mm diameter and 14 mm diameter, respectively), an additional silver ring electrode as an auxiliary electrode (silver gauze, 1024 mesh/cm$^2$, 0.12 wire diameter, 99.9% Ag, 20 mm outer diameter and 16 mm inner diameter, respectively), a hydrogel formulation (comprising 2.5%-wt. Klucel® HF and 0.1%-wt. sodium chloride, having a pH value of 7.0) as additional reservoir (15) being in contact with the silver ring electrode, a foam ring as (9) (Alveolit TA 1001 005 White, 95 kg/m$^3$, 24 mm outer diameter, 20 mm inner diameter), hydrogel formulation C as drug reservoir (3), teflon ring as barrier material (10) (thickness 1 mm, outer diameter 16 mm, inner diameter 11 mm and, thickness 0.5 mm, outer diameter 20 mm, inner diameter 16 mm, respectively), silicone adhesive Bio PSA-7 4502 as adhesive layer (4a), which has been in contact with a removable protective layer prior to use (transparent PETP foil manufactured by 3M®, 74 μm, with one-side fluorination, 24 mm diameter), acrylate adhesive DuroTAK 387-2054 as a second adhesive layer (8), a PET foil as surface layer (7) (Loparex PET foil, 75 μm, 105 g/m$^2$, 24 mm diameter).

Three wires were soldered to the electrodes and connected to a conventional current source as electric power source (6a) (Voltakraft® laboratory power supply DIGI 35).

Figure 11:
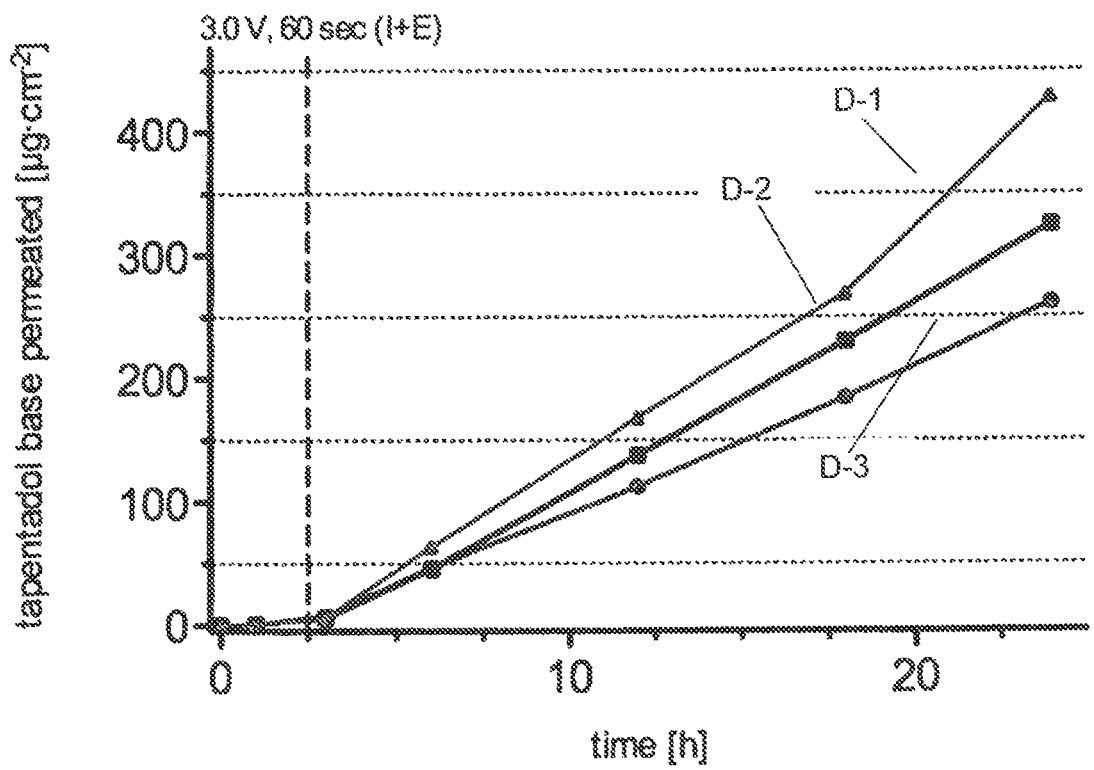
Figure 12:
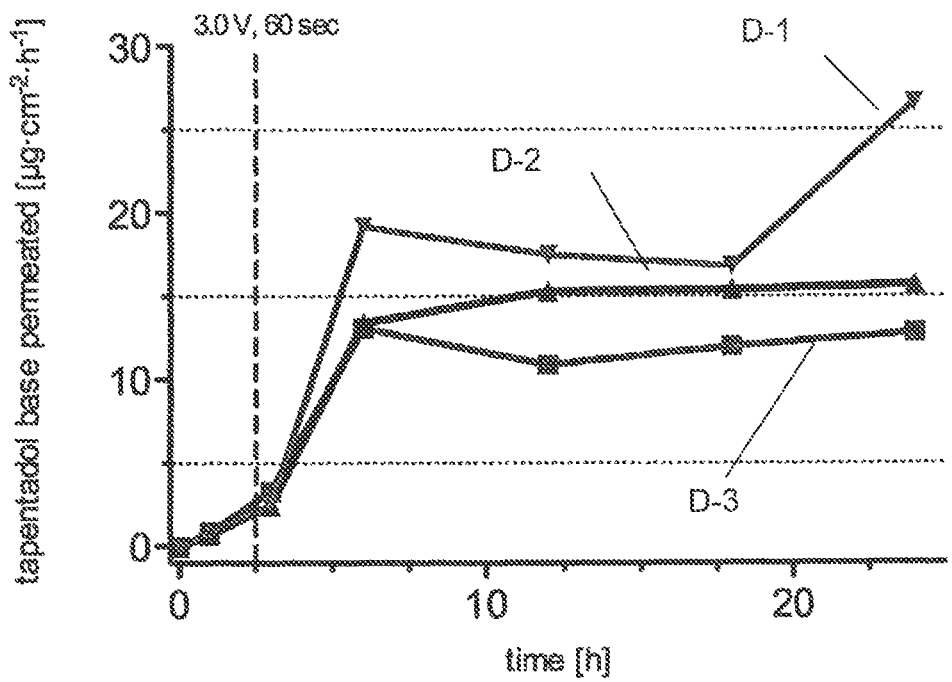

A transdermal delivery experiment across mouse skin has been performed. This experiment has been performed three times (D-1, D2 and D3 as example 3a) as indicated in FIG. 11 and FIG. 12. In the first electrophoretic phase, only the silver electrodes as pair of electrodes consisting of an active electrode (1a) and a counter electrode (2a) were connected to the current supply. After application of 2.5 hours a single pulse having a pulse length of 60 s at a constant voltage of 3 V has been applied. After application of said pulse both electrodes were disconnected from the voltage generator. In the second iontophoretic phase following the electrophoretic phase, the counter electrode (2a) of the electrophoretically used pair of silver electrodes (1a and 2a) is used as an active electrode (1b) and the additional silver ring electrode is used a counter electrode (2b). A single pulse having a pulse length of 60 s at a constant voltage of 3 V has been applied in the iontophoretic phase.

FIG. 11 provides a graphical representation of the results of the cumulative combined electrophoretic and iontophoretic delivery (in µg/cm$^2$) of Tapentadol across the skin according to example 3a (D-1, D-2 and D-3).

As can be derived from FIG. 11, the cumulative data indicate that the total amount of Tapentadol permeated can be increased up to 430 µg/cm$^2$ after 24 hours by combined electrophoretic and iontophoretic delivery (D-1 in FIG. 11).

FIG. 12 provides a graphical representation of the results of the drug flux (given in µg/cm$^2$ per h) of Tapentadol across the skin according to example 3a.

As can be derived from FIG. 12, the increased flux observed in case of example 3a as displayed in FIG. 11 is due to the application of the electric current since the increase in flux unambiguously correlates with the time of applying the current, even though a delay time can be observed. The increase in the flux diagram for D-1 is probably due to injuries in the mouse skin that led to an infiltration of the hydrogel into the acceptor medium.

Thus, substantial drug delivery was achieved with combined electrophoretic and iontophoretic delivery.

Example 3b

The hydrogel formulation C (as described in example 2a) has been placed in a combined electrophoretic and iontophoretic device according to FIG. 3. The same components were used for preparing the inventive combined electrophoretic and iontophoretic device as described in example 3a.

Figure 13:
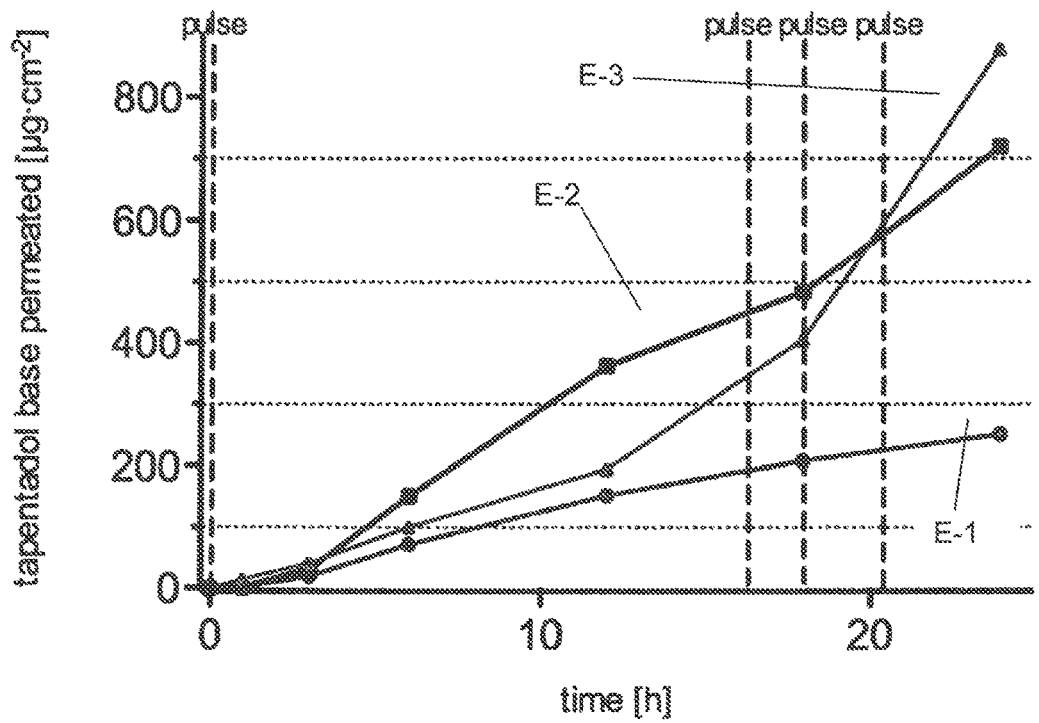
FIG. 13 provides a graphical representation of the results of the cumulative combined electrophoretic and iontophoretic delivery (in $\mu g/cm^2$) of Tapentadol across the skin in comparison with the results of cumulative electrophoretic delivery (in $\mu g/cm^2$) of Tapentadol across the skin according to example 3b.
Figure 14:
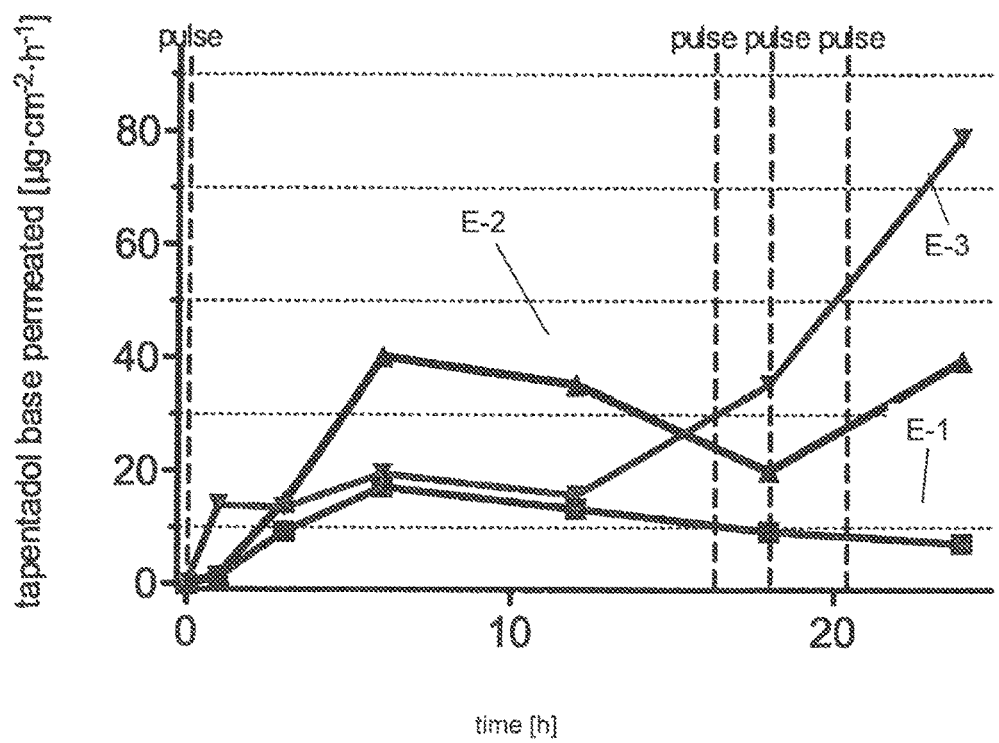
FIG. 14 provides a graphical representation of the results of the drug flux (given in $\mu g/cm^2$ per h) of Tapentadol across the skin according to example 3b.

Three transdermal delivery experiments (E-1, E2 and E3 as example 3b) to mouse skin have been performed in order to directly assess differences between a solely electrophoretic transdermal delivery and a combined electrophoretic and iontophoretic transdermal delivery as indicated in FIG. 13 and FIG. 14:
the device according to E-1 was subjected to a single electrophoretic pulse length for the period of 60 s directly after applying the patch to the skin (t=0) at a constant voltage of 3 V,
the device according to E-2 was subjected to multiple electrophoretic pulse lengths, starting with a first pulse directly after applying the patch to the skin (t=0), a second pulse after 15.75 hours, a third pulse after 18 h and a fourth pulse after 20.75 hours, wherein each pulse was applied for the period of 60 s, and wherein the voltage during pulse application was in each case held constant at 3 V,
the device according to E-3 was subjected to multiple pulse lengths of a combined electrophoretic and iontophoretic sequence, starting with a first electrophoretic pulse directly after applying the patch to the skin (t=0), directly followed by a first iontophoretic pulse having a pulse length of 1 hour, a second electrophoretic pulse after 15.75 hours, directly followed by a second iontophoretic pulse having a pulse length of 2.25 hours, a third electrophoretic pulse after 18 h, directly followed by a third iontophoretic pulse having a pulse length of 2.75 hours, and a fourth electrophoretic pulse after 20.75 hours, directly followed by a fourth iontophoretic pulse having a pulse length of 3.25 hours, wherein each electrophoretic pulse was applied for the period of 60 s, and wherein the voltage during electrophoretic pulse application was in each case held constant at 3 V, and wherein the voltage during iontophoretic pulse application was in each case held constant at 9 V.

FIG. 13 provides a graphical representation of the results of the cumulative combined electrophoretic and iontophoretic delivery (in µg/cm$^2$) of Tapentadol across the skin in comparison with the results of cumulative electrophoretic delivery (in µg/cm$^2$) of Tapentadol across the skin according to example 3b (E-1, E-2 and E-3).

As can be derived from FIG. 13, the cumulative data indicate that the total amount of Tapentadol permeated can be increased up to more than 800 µg/cm$^2$ after 24 hours by combined electrophoretic and iontophoretic delivery (E-3 in FIG. 13).

FIG. 14 provides a graphical representation of the results of the drug flux (given in µg/cm$^2$ per h) of Tapentadol across the skin according to example 3b.

As can be derived from FIG. 14, the increased flux observed in case of example 3b as displayed in FIG. 13 is due to the application of the electric current since the increase in flux unambiguously correlates with the time of applying the current, even though a delay time can be observed. In case of E-2 and E-3 the flux was—compared to E-1—intensified by applying the multiple pulse sequences.

In all three devices E-1, E-2 and E-3, the first (electrophoretic) pulse was applied directly after applying the device to the skin (t=0), however, only in E-3 a distinct increase in both the total amount of Tapentadol permeated and the flux was detected. After about 3 hours, the overall permeation rate was comparable in all devices E-1, E-2 and E-3. Subsequently, device E-2 exhibited a strong upswing, whereas E-1 and E-3 led to a moderate slope. Multiple electric pulses (multiple electrophoretic pulses for E-2 and a sequence of multiple electrophoretic and iontophoretic pulses for E-3) afforded a significantly larger amount of permeated Tapentadol than for E-1 (more than 700 µg/cm$^2$ after 24 hours for E-2) and more than 800 µg/cm$^2$ after 24 hours for E-3). However, whereas E-2 exhibited a fall-off of the drug flux (cf. FIG. 14) of about 50% after 18 hours compared to the maximum at about 6 hours, E-3 showed an increase of drug flux at this interval which continued to the end of the experiment.

Example 3c

The hydrogel formulation C (as described in example 2a) has been placed in a combined electrophoretic and iontophoretic device according to FIG. 3. The same components were used for preparing the inventive combined electrophoretic and iontophoretic device as described in example 3a.

Figure 15:
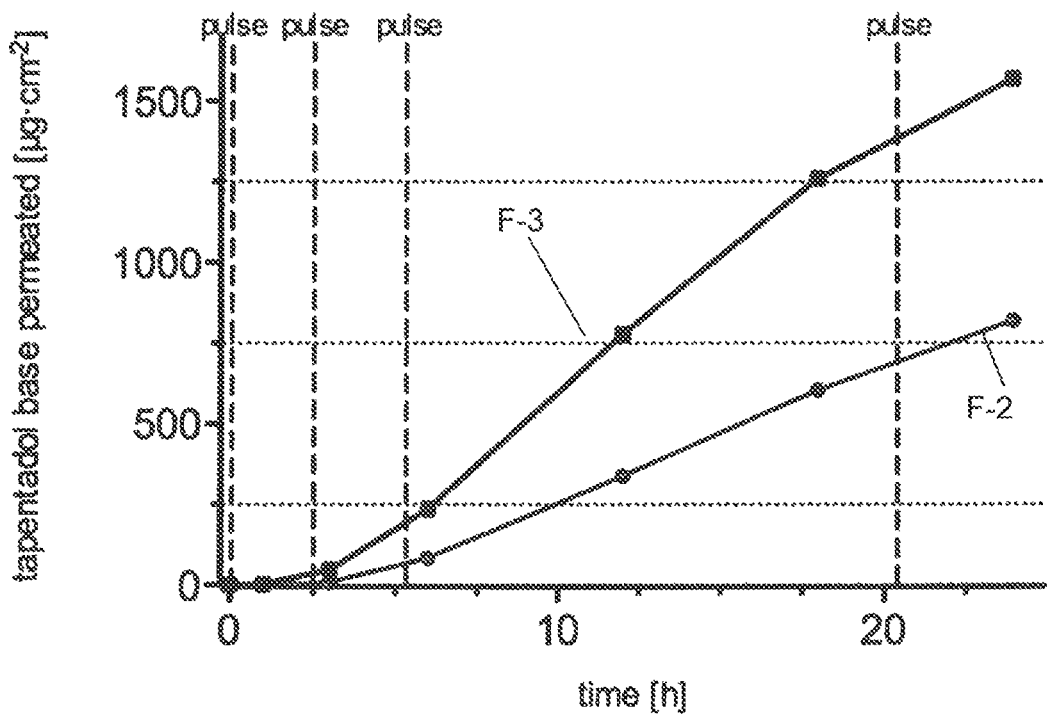
FIG. 15 provides a graphical representation of the results of the cumulative combined electrophoretic and iontophoretic delivery (in $\mu g/cm^2$) of Tapentadol across the skin in comparison with the results of cumulative electrophoretic delivery (in $\mu g/cm^2$) of Tapentadol across the skin according to example 3c.
Figure 16:
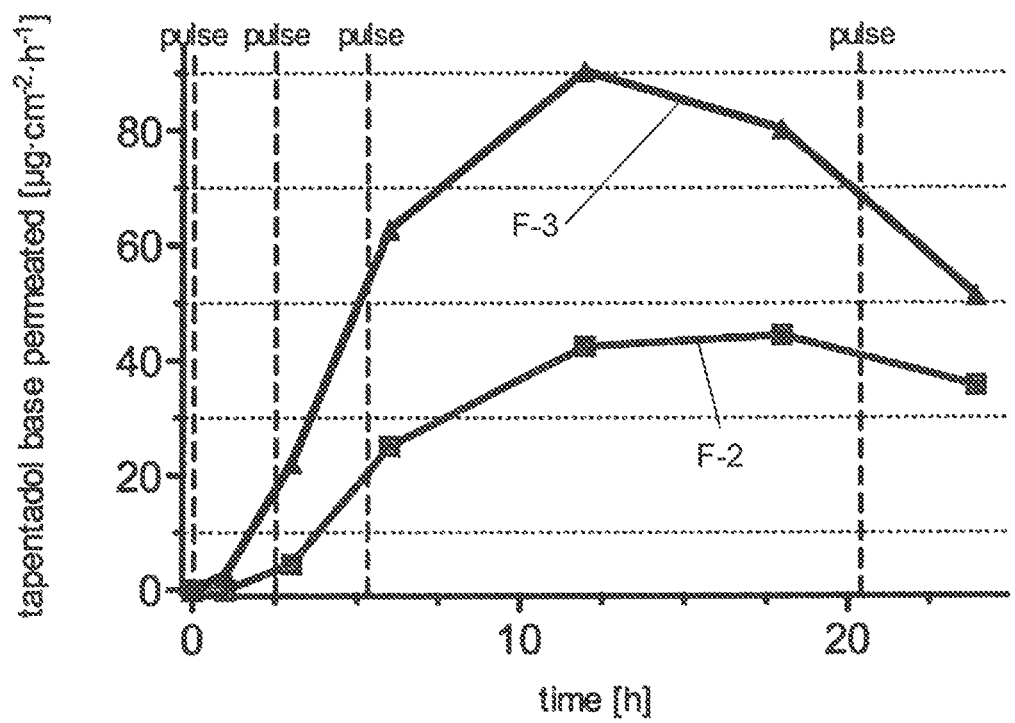
FIG. 16 provides a graphical representation of the results of the drug flux (given in $\mu g/cm^2$ per h) of Tapentadol across the skin according to example 3c.

Two transdermal delivery experiments (F-2 and F-3 as example 3c) across mouse skin have been performed in order to directly assess differences between a solely electrophoretic transdermal delivery and a combined electrophoretic and iontophoretic transdermal delivery as indicated in FIG. 15 and FIG. 16:
the device according to F-2 was subjected to multiple electrophoretic pulse lengths, starting with a first pulse directly after applying the patch to the skin (t=0), a second pulse after 2.5 hours, a third pulse after 5.5 hours and a fourth pulse after 21.5 hours, wherein each pulse was applied for the period of 60 s, and wherein the voltage during pulse application was in each case held constant at 4 V, the device according to F-3 was subjected to multiple pulse lengths of a combined electrophoretic and iontophoretic sequence, starting with a first electrophoretic pulse directly after applying the patch to the skin (t=0), directly followed by a first iontophoretic pulse having a pulse length of 2.5 hours, a second electrophoretic pulse after 2.5 hours, directly followed by a second iontophoretic pulse having a pulse length of 3 hours, a third electrophoretic pulse after 5.5 hours, directly followed by a third iontophoretic pulse having a pulse length of 16 hours, and a fourth electrophoretic pulse after 21.5 hours, directly followed by a fourth iontophoretic pulse having a pulse length of 2.5 hours, wherein each electrophoretic pulse was applied for the period of 60 s, and wherein the voltage during electrophoretic pulse application was in each case held constant at 4 V, and wherein the voltage during iontophoretic pulse application was in each case held constant at 9 V.

Compared to E-2 and E-3 of example 3b, the times for applying electric pulses in F-2 and F-3 were shifted to times closer to the start of the permeation. Further, the voltage was increased to 4 V during the application of electrophoretic pulses.

FIG. 15 provides a graphical representation of the results of the cumulative combined electrophoretic and iontophoretic delivery (in $\mu g/cm^2$) of Tapentadol across the skin in comparison with the results of cumulative electrophoretic delivery (in $\mu g/cm^2$) of Tapentadol across the skin according to example 3c (F-2 and F-3).

As can be derived from FIG. 15, the cumulative data indicate that the total amount of Tapentadol permeated can be increased up to about 1500 $\mu g/cm^2$ after 24 hours by combined electrophoretic and iontophoretic delivery (F-3 in FIG. 15).

FIG. 16 provides a graphical representation of the results of the drug flux (given in $\mu g/cm^2$ per h) of Tapentadol across the skin according to example 3c.

As can be derived from FIG. 16, the increased flux observed in case of example 3c as displayed in FIG. 15 is due to the application of the electric current since the increase in flux unambiguously correlates with the time of applying the current, even though a delay time can be observed.

Example 4

The purity of Tapentadol contained in the inventive device according to F-3 of example 3c after electric-field-assisted administration of the device has been investigated by HPLC techniques in order to find out if any electrically induced degradation of Tapentadol might occur.

As can be derived from said HPLC analysis, the sample obtained from the exhausted hydrogel of F-3 of example 3c had a Tapentadol content of 95.3%. The sum of impurities was 4.7%. Considering that the samples might include degradation products from active enzymes of the mouse skin, the sum of impurities is on a low level.

Thus, electric-field administration of the inventive device does not induce a significant degradation of Tapentadol contained therein during administration.

What is claimed is:

1. A pharmaceutical device comprising
at least one pair of electrodes (1a and 2a and/or 1b and 2b), wherein each of the at least one pair of electrodes consists of one active electrode (1a or 1b) and one counter electrode (2a or 2b),
a drug reservoir (3) containing Tapentadol and/or a physiologically acceptable salt thereof,
a means for applying the device to skin (5), and
an adhesive layer (4a),
wherein at least one electrode of the at least one pair of electrodes (1a and 2a and/or 1b and 2b) is located entirely within the adhesive layer (4a) when the device is applied to the skin,
wherein at least one electrode of the at least one pair of electrodes (1a and 2a and/or 1b and 2b) is arranged between at least a portion of the drug reservoir and skin when the device is applied to the skin, and
wherein the pharmaceutical device provides electric-field assisted administration of Tapentadol and/or of the physiologically acceptable salt thereof.

2. The device according to claim 1 additionally comprising a control unit for regulating the electrical potential difference (Va and/or Vb) applied to the at least one pair of electrodes (1a and 2a and/or 1b and 2b) and/or the at least one optionally present additional auxiliary electrode.

3. The device according to claim 1, wherein the drug reservoir (3) comprises an aqueous medium, preferably a hydrogel.

4. The device according to claim 1, wherein the drug reservoir (3) contains the physiologically acceptable salt of Tapentadol.

5. The device according to claim 1, which is a pharmaceutical patch comprising a surface layer (7) and wherein the drug reservoir (3) is preferably located between the surface layer (7) and the adhesive layer (4a) or preferably located at least partly within the adhesive layer (4a).

6. The device according to claim 1, wherein the at least one pair of electrodes (1b and 2b) is provided to create an electric field (Fb) by applying an electrical potential difference (Vb), and is arranged such that the electric field (Fb) is substantially parallel to the skin (5) when the device is applied thereto.

7. The device according to claim 6, wherein the electric field (Fb) induces iontophoretic movement of Tapentadol and/or of the physiologically acceptable salt thereof out of the device from the drug reservoir (3) into the skin (5).

8. The device according to claim 1, wherein the at least one pair of electrodes (1a and 2a) is provided to create an electric field (Fa) by applying an electrical potential difference (Va), and is arranged such that the electric field (Fa) is substantially perpendicular to the skin (5) when the device is applied thereto.

9. The device according to claim 8, wherein the electric field (Fa) induces electrophoretic movement of Tapentadol and/or of the physiologically acceptable salt thereof within the device from the drug reservoir (3) towards the skin (5).

10. A method of treating pain comprising administering Tapentadol and/or a physiologically acceptable salt thereof, wherein Tapentadol and/or the physiologically acceptable salt thereof is administered by means of a pharmaceutical device according to claim 1.

11. The method according to claim 10, wherein an electrical potential difference (Va and/or Vb) is applied to the at least one pair of electrodes (1a and 2a and/or 1b and 2b) consisting of the active electrode (1a and/or 1b) and the counter electrode (2a and/or 2b), and/or the additional electrode, which is within the range of from 0.5 to 12.5 V.

12. The method according to claim 10, wherein an electrical potential difference (Va and/or Vb) is repeatedly applied in predetermined repetition intervals in each case for a predetermined period of time within the total period of time, during which the device is applied to the skin (5).

13. The method according to claim 10, wherein a total period of time during which an electrical potential difference (Va and/or Vb) is applied to the at least one pair of electrodes (1a and 2a and/or 1b and 2b) and/or the additional auxiliary electrode is at most 75% of the total period of time during which the device is applied to the skin (5).

14. The device according to claim 1, further comprising at least one additional electrode as an auxiliary electrode (1a and/or 2b).

15. The device according to claim 14, comprising:
A) the first pair of electrodes (1a and 2a) consisting of the active electrode (1a) and the counter electrode (2a), which are provided to create an electric field (Fa) by applying an electrical potential difference (Va), and are arranged such that the electric field (Fa) is substantially perpendicular to the skin (5) when the device is applied thereto, and the auxiliary electrode, which functions as the counter electrode (2b) in such a way that the counter electrode (2a) of the first pair of electrodes (1a and 2a) is used as the active electrode (1b) for creating an electric field (Fb) by applying an electrical potential difference (Vb), these two electrodes (1b and 2b) forming a second pair of electrodes consisting of the active electrode (1b) and the counter electrode (2b) and are arranged such that the electric field (Fb) is substantially parallel to the skin (5) when the device is applied thereto, or B) the first pair of electrodes (1b and 2b) consisting of the active electrode (1b) and the counter electrode (2b), which are provided to create the electric field (Fb) by applying the electrical potential difference (Vb), and are arranged such that the electric field (Fb) is substantially parallel to the skin (5) when the device is applied thereto, and
the auxiliary electrode, which functions as the active electrode (1a) for creating an electric field (Fa) by applying the electrical potential difference (Va) using the active electrode (1b) of the first pair of electrodes (1b and 2b) as the counter electrode (2a), these two electrodes (1a and 2a) forming the second pair of electrodes consisting of the active electrode (1a) and the counter electrode (2a) and are arranged such that the electric field (Fa) is substantially perpendicular to the skin (5) when the device is applied thereto.

16. The device according to claim 15, wherein
A) the electric field (Fa) created by the at least one first pair of electrodes consisting of the active electrode (1a) and the counter electrode (2a) induces electrophoretic movement of Tapentadol and/or of the physiologically acceptable salt thereof within the device from the drug reservoir (3) towards the skin (5) and the electric field (Fb) created by the second pair of electrodes consisting of the active electrode (1b) and the counter electrode (2b) induces iontophoretic movement of Tapentadol and/or of the physiologically acceptable salt thereof out of the device from the drug reservoir (3) into the skin (5), or B) the electric field (Fb) created by the at least one first pair of electrodes consisting of the active electrode (1b) and the counter electrode (2b) induces iontophoretic movement of Tapentadol and/or of the physiologically acceptable salt thereof out of the device from the drug reservoir (3) into the skin (5) and
the electric field (Fa) created by the second pair of electrodes consisting of the active electrode (1a) and the counter electrode (2a) induces electrophoretic movement of Tapentadol and/or of the physiologically acceptable salt thereof within the device from the drug reservoir (3) towards the skin (5).

* * * * *